US006409750B1

(12) United States Patent
Hyodoh et al.

(10) Patent No.: US 6,409,750 B1
(45) Date of Patent: Jun. 25, 2002

(54) WOVEN BIFURCATED AND TRIFURCATED STENTS AND METHODS FOR MAKING THE SAME

(75) Inventors: Hideki Hyodoh, Sapporo (JP); Andras Konya; Kenneth C. Wright, both of Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/495,984

(22) Filed: Feb. 1, 2000

Related U.S. Application Data

(60) Provisional application No. 60/118,185, filed on Feb. 1, 1999, and provisional application No. 60/125,192, filed on Mar. 18, 1999.

(51) Int. Cl.[7] ................................................. A61F 2/06
(52) U.S. Cl. ........................ 623/1.1; 623/1.35; 623/1.51
(58) Field of Search ................................. 623/1.1, 1.35, 623/1.5, 1.51, 1.53, 1.22, 1.16

(56) References Cited

U.S. PATENT DOCUMENTS

| | | | |
|---|---|---|---|
| 2,836,181 A | 5/1958 | Tapp ........................... 128/334 |
| 2,936,257 A | 5/1960 | Nailler et al. ............... 154/2.22 |
| 3,463,197 A | 8/1969 | Slade .......................... 138/125 |
| 3,620,218 A | 11/1971 | Schmitt .................. 128/334 R |
| 4,503,569 A | 3/1985 | Dotter ............................. 3/1.4 |
| 4,580,568 A | 4/1986 | Gianturco .................... 128/345 |
| 4,619,246 A | 10/1986 | Molgaard-Neilsen et al. .. 128/1 |
| 4,655,771 A | 4/1987 | Wallsten ......................... 623/1 |
| 4,733,665 A | 3/1988 | Palmaz ........................ 128/343 |
| 4,739,762 A | 4/1988 | Palmaz ........................ 128/343 |
| 4,776,337 A | 10/1988 | Palmaz ........................ 128/343 |
| 4,850,999 A | 7/1989 | Planck ........................... 623/1 |
| 4,954,126 A | 9/1990 | Wallsten ....................... 600/36 |

(List continued on next page.)

FOREIGN PATENT DOCUMENTS

| | | | |
|---|---|---|---|
| EP | 0701800 A1 | 3/1996 | ............. A61F/2/06 |
| EP | 0782841 A2 | 7/1997 | |
| EP | 893108 | 1/1999 | |
| FR | 2678508 | * 1/1996 | ................ 623/1.35 |
| GB | 1183497 | 3/1970 | |

(List continued on next page.)

OTHER PUBLICATIONS

Balko et al, "Transfemoral placement of intraluminal polyurethane prosthesis for abdominal aortic aneurysm," *J. Surg. Res.*, 40:305–309, 1986.
"Conformance by Design," World Medical Manufacturing Corporation.
World Medical News, 5(5), Feb. 1997.
Zarins et al, "AneuRx stent graft versus open surgical repair of abdominal aortic aneurysms: multicenter prospective clinical trial," *J. Vasc. Surg.*, 29:292–308, 1999.

(List continued on next page.)

*Primary Examiner*—David O. Reip
*Assistant Examiner*—Julian W. Woo
(74) *Attorney, Agent, or Firm*—Fulbright & Jaworski L.L.P.

(57) ABSTRACT

Bifurcated and trifurcated woven stents for insertion and delivery into a variety of anatomical structures, including the aortic-iliac bifurcation, the superior vena cava junction, and the inferior vena cava junction. The bifurcated stents includes a first leg formed from a first plurality of wires, a second leg formed from a second plurality of wires, and a common body formed from the first and second pluralities of wires. The wires may be nitinol. Biodegradable filaments may also be utilized. The angles created between the crossed wires is preferably obtuse. A variety of delivery devices formed from differently-sized tubes, portions of which may operate co-axially with each other, are also included. The bifurcated stents may be formed from as few as two wires. The stents may be formed using plain weaving effected either by hand or by machine.

36 Claims, 32 Drawing Sheets

U.S. PATENT DOCUMENTS

| | | | |
|---|---|---|---|
| 4,969,458 A | 11/1990 | Wiktor | 606/194 |
| 4,997,440 A * | 3/1991 | Dumican | 623/1.1 |
| 5,026,377 A | 6/1991 | Burton et al. | 606/108 |
| 5,061,275 A | 10/1991 | Wallsten et al. | 623/1 |
| 5,102,417 A | 4/1992 | Palmaz | 606/195 |
| 5,104,404 A | 4/1992 | Wolff | 623/1 |
| 5,135,536 A | 8/1992 | Hillstead | 606/195 |
| 5,219,355 A | 6/1993 | Parodi et al. | 606/191 |
| B1 4,733,665 A | 1/1994 | Palmaz | 606/108 |
| 5,350,398 A | 9/1994 | Pavcnik et al. | 606/200 |
| 5,360,443 A | 11/1994 | Barone et al. | 623/1 |
| 5,389,106 A | 2/1995 | Tower | 606/198 |
| 5,395,390 A | 3/1995 | Simon et al. | 606/198 |
| 5,411,549 A | 5/1995 | Peters | 623/1 |
| 5,419,231 A | 5/1995 | Earle, III et al. | 87/1 |
| D359,802 S | 6/1995 | Fontaine | D24/155 |
| 5,425,739 A | 6/1995 | Jessen | 606/155 |
| 5,425,984 A | 6/1995 | Kennedy et al. | 428/229 |
| 5,443,458 A | 8/1995 | Eury | 604/891.1 |
| 5,478,355 A | 12/1995 | Muth et al. | 606/230 |
| 5,485,774 A | 1/1996 | Osborne | 87/6 |
| 5,507,769 A | 4/1996 | Marin et al. | 606/198 |
| B1 4,954,126 A | 5/1996 | Wallsten | 600/36 |
| 5,527,324 A | 6/1996 | Krantz et al. | 606/155 |
| 5,551,954 A | 9/1996 | Buscemi et al. | 623/1 |
| B1 4,655,771 A | 9/1996 | Wallsten | 623/1 |
| 5,575,817 A * | 11/1996 | Martin | 623/1.1 |
| 5,591,195 A | 1/1997 | Taheri et al. | 606/194 |
| 5,597,378 A | 1/1997 | Jervis | 606/78 |
| 5,632,771 A | 5/1997 | Boatman v | 623/1 |
| 5,643,339 A | 7/1997 | Kavteladze et al. | 623/1 |
| 5,669,924 A * | 9/1997 | Shaknovich | 623/1.1 |
| 5,669,936 A | 9/1997 | Lazarus | 623/1 |
| 5,670,161 A | 9/1997 | Healy et al. | 424/426 |
| 5,674,277 A | 10/1997 | Freitag | 623/1 |
| 5,679,400 A | 10/1997 | Tuch | 427/2.14 |
| 5,683,411 A | 11/1997 | Kavteladze et al. | 606/200 |
| 5,707,376 A | 1/1998 | Kavteladze et al. | 606/108 |
| 5,709,701 A | 1/1998 | Parodi | 606/194 |
| 5,713,917 A | 2/1998 | Leonhardt et al. | 606/194 |
| 5,716,396 A | 2/1998 | Williams, Jr. | 623/1 |
| 5,720,735 A | 2/1998 | Dorros | 604/284 |
| 5,733,327 A | 3/1998 | Igaki et al. | 623/1 |
| 5,741,325 A * | 4/1998 | Chaikof et al. | 623/1.1 |
| 5,766,710 A | 6/1998 | Turnlund et al. | 428/36.1 |
| 5,769,882 A | 6/1998 | Fogarty et al. | 623/1 |
| 5,772,668 A | 6/1998 | Summers et al. | 606/108 |
| 5,824,053 A | 10/1998 | Khosravi et al. | 623/1 |
| B1 4,739,762 A | 10/1998 | Palmaz | 606/108 |
| 5,830,229 A | 11/1998 | Kónya et al. | 606/198 |
| 5,851,217 A | 12/1998 | Wolff et al. | 623/1 |
| 5,860,998 A | 1/1999 | Robinson et al. | 606/194 |
| 5,876,432 A | 3/1999 | Lau et al. | 623/1 |
| 5,891,191 A | 4/1999 | Stinson | 623/1 |
| 5,902,332 A | 5/1999 | Schatz | 623/1 |
| 5,913,896 A | 6/1999 | Boyle et al. | 623/1 |
| 5,928,279 A | 7/1999 | Shannon et al. | 623/1 |
| 5,944,738 A | 8/1999 | Amplatz et al. | 606/213 |
| 5,968,088 A | 10/1999 | Hansen et al. | 623/1 |

FOREIGN PATENT DOCUMENTS

| | | |
|---|---|---|
| GB | 1205743 | 9/1970 |
| GB | 2135585 | 9/1984 |
| WO | WO 91/17789 | 5/1991 |
| WO | WO 96/01591 | 1/1996 |
| WO | WO 98/29043 | 12/1997 |
| WO | WO 99/32051 | 7/1998 |
| WO | WO 00/09059 | 8/1999 |
| WO | WO 00/44308 | 8/2000 |

OTHER PUBLICATIONS

Letter from Howard J. Leonhardt to Sidney Wallace, dated Apr. 22, 1997, with two attachments.

Document entitled "Patient: #1115", faxed from Howard J. Leonhardt to Andras Konya on Apr. 11, 1998.

JVIR Supplement, Scientific Program, SCVIR $22^{nd}$ Annual Scientific Meeting, Mar. 8–13, 1997, Sheraton Washington Hotel, 8(1) Part 2, pp. 251–252, Jan.–Feb. 1997.

World Medical News, 5(6), May 1997.

Pictures of poster presented at SCVIR $22^{nd}$ Annual Scientific Meeting, Mar. 8–13, 1997, Sheraton Washington Hotel.

Descriptions on poster presented at SCVIR $22^{nd}$ Annual Scientific Meeting, Mar. 8–13, 1997, Sheraton Washington Hotel.

International Search Report dated Jun. 24, 1999.

Didcott, "Oesophageal strictures: treatment by slow continuous dilation," *Ann. Roy. Coll. Surg. Engl.*, 53:112–126, 1973.

"Wallstent Endoprosthesis" marketing material, Boston Seietific Vascular, 1998.

Reexamination file history for B1–4,954,126.

Reexamination file history for B1–4,655,771.

Dotter, "Transluminally–placed coilspring endarterial tube grafts," *Investigative Radiology*, 4:329–332, 1969.

Fallone et al., "Elastic characteristics of the self–expanding metallic stents," *Invest. Radiol.*, 23:370–376, 1988.

Gillams et al., "Self–expandable stainless steel braided endoprosthesis for biliary strictures," *Radiology*, 174:137–140, 1990.

Günther et al., "Venous stenoses in dialysis shunts: Treatment with self–expanding metallic stents," *Radiology*, 170:401405, 1989.

Milroy et al., "A new stent for the treatment of urethral strictures," *Br. J. Urol.*, 63:392–396, 1989.

Murayama et al., "Nonadhesive liquid embolic agent for cerebral arteriovenous malformations: Preliminary histopathological studies in swine rete mirabile," *Neurosurgery*, 43:1164–1175, 1998.

Nashef et al., "Expanding wire stents in benign tracheobronchial disease: Indications and complications," *Ann. Thorac. Surg.*, 54:937–940, 1992.

Palmaz, "Balloon–expandable intravascular stent," *AJR*, 150:1263–1269, 1988.

Peterson et al., "Gianturco–Rosch Z stents in tracheobronchial stenoses," *JVIR*, 6:925–931, 1995.

Schampaert, "The V–stent: a novel technique for coronary bifurcation stenting," *Cathet. Cardiovasc. Diagn.*, 39(3):320–326, 1996.

Shürmann et al., "Neointimal hyperplasia in low–profile nitinol stents, Palmaz stents, and Wallstents: a comparative experimental study," *Cardiovasc. Intervent. Radiol.*, 19:248–254, 1996.

Taki et al., "A new liquid material for embolization of arteriovenous malformations," AJNR, 11:163–168, 1990.

Terada et al., "Embolization of arteriovenous malformations with peripheral aneurysms using ethylene vinyl alcohol copolymer," *J. Neurosurg.*, 75:655–660, 1991.

Wallace et al., "Tracheobronchial tree: Expandable metallic stents used in experimental and clinical applications," *Radiology*, 158:309–312, 1986.

Ben–Menachem et al., "Hemorrhage associated with pelvic fractures: causes, diagnosis, and emergent management," *AJR*, 157:1005–1014, 1991.

Bing et al. "Percutaneous ureteral occlusion with use of Gianturco coils and gelatine sponge, Part I. Swine model" *JVIR*; 3:313–317, 1992 (a).

Bing et al. "Percutaneous ureteral occlusion with use of Gianturco coils and gelatine sponge, Part II. Clinical Experience," *JVIR*; 3:319–321, 1992 (b).

Cambier et al., "Percutaneous closure of the small (<2.5 mm) patent ductus arteriosus using coil embolization," *Am. J. Cardiol.*, 69:815–816, 1992.

Crochet et al., "Vena Tech–LGM filter: long–term results of a prospective study," *Radiology*, 188:857–860, 1993.

Dorfman, "Percutaneous inferior vena cava filters," *Radiology*, 174:987–992, 1990.

Dutton et al., "Pulmonary arteriovenous malformations: results of treatment with coil embolization in 53 patients," *AJR*, 165:1119–1125, 1995.

Fischell et al., "The β–particle–emitting radiosotope stent (Isostent): animal studies and planned clinical trials," *Am. J. Cardiol.*, 78(Suppl 3A):45–50, 1996.

Furuse et al., "Hepatocellular carcinoma with portal vein tumor thrombus: embolization of arterioportal shunts," *Radiology*, 204:787–790, 1997.

Gianturco et al., "Mechanical device for arterial occlusion," *AJR*, 124:428–435, 1975.

Grassi, "Inferior vena caval filters: Analysis of five currently available devices," *AJR*, 156:813–821, 1991.

Grifka et al., "Transcatheter patent ductus arteriosus closure in an infant using the Gianturco Grifka vascular occlusion device," *Am. J. Cardiol.*, 78:721–723, 1996.

Guglielmi et al., "Highflow, small–hole arteriovenous fistulas: treatment with electrodetachable coils," *AJNR*, 16:325–328, 1995.

Hammer et al., "In vitro evaluation of vena cava filters," *JVIR*, 5:869–876, 1994.

Hendrickx et al., "Long–term survival after embolization of potentially lethal bleeding malignant pelvic turnouts," *Br. J. Radial.*, 68:1336–1343, 1995.

Hijazi and Geggel, "Results of anterograde transcatheter closure of patent ductus arteriosus using single or multiple Gianturco coils," *Am. J. Cardiol.*, 74:925–929, 1994.

Hijazi and Geggel, "Transcatheter closure of patent ductus arteriosus using coils," *Am. J. Cardiol.*, 79:1279–1280, 1997.

Hosking et al., "Transcatheter occlusion of the persistently patent ductus arteriosus," *Circulation*, 84:2313–2317, 1991.

Jaeger et al., "In vitro model for evaluation of inferior vena cava filters: effect of experimental parameters on thrombus–capturing efficacy of the Vena Tech–LGM filter," *JVIR*, 9:295–304, 1998.

Kato et al., "Use of a self–expanding vascular occluder for embolization during endovascular aortic aneurysm repair," *JVIR*, 8:27–33, 1997.

Katsamouris et al., "Inferior vena cava filters: In vitro comparison of clot trapping and flow dynamics," *Radiology*, 166:361–366, 1988.

Kónya et al., "Anchoring coil embolization in a high–flow arterial model," *JVIR*, 9:249–254, 1998.

Kónya and Wright, Preliminary results with a new vascular basket occluder in swine. *JVIR*, 10:1043–1049, 1999.

Korbin et al., "Comparison of filters in an oversized vena caval phantom: intracaval placement of a Bird's Nest filter versus biiliac placement of Greenfield, Vena–Tech–LGM, and Simon nitinol filters," *JVIR*, 3:559–564, 1992.

Krichenko et al., "Angiographic classification of the isolated, persistently patent ductus arteriosus and implications for percutaneous catheter occlusion," *Am. J. Cardiol.*, 63:877–880, 1989.

Latson, "Residual shunts after transcatheter closure of patent ductus arteriosus," *Circulation*, 84:2591 2593, 1991.

Levey et al., "Safety and efficacy of transcatheter embolization of auxiliary and shoulder arterial injuries," *JVIR*, 2:99–104, 1991.

Lipton et al., "Percutaneous Retrieval of two Wallstent endoprostheses from the heart through a single jugular sheath," *JVIR*, 6:469–472, 1995.

Lloyd et al., "Transcatheter occlusion of patent ductus arteriosus with Gianturco coils," *Circulation*, 88:1412–1420, 1993.

Magal et al., "A new device for transcatheter closure of patent ductus arteriosus: a feasibility study in dogs," *Invest. Radiol.*, 24:272–276, 1989.

Marks et al., "A mechanically detachable coil for the treatment of aneurysms and occlusion of blood vessels," *AJNR*, 15:821–827, 1994.

Masura et al., "Catheter closure of moderate to large sized patent ductus arteriosus using the new Amplatz duct occluder: immediate and short term results," *J. Am. Coll. Cardiol.*, 31:878–882, 1998.

Milward, "Temporary and Retrievable inferior vena cava filters: Current status," *JVIR*, 9:381–387, 1998.

Murayama et al., "Nonadhesive liquid embolic agent for cerebral arteriovenous malformations: Preliminary histopathological studies in swine rete mirabile," *Neurosurgery*, 43:1164–1175, 1998.

Nancarrow et al., "Stability of coil emboli: an in vitro study," *Cardiovasc. Intervent. Radiol.*, 10:226–229, 1987.

O'Halpin et al., "Therapeutic arterial embolization: report of five years' experience," *Clin. Radiol.*, 354:85–93, 1984.

Pozza et al., "Transcatheter occlusion of patent ductus arteriosus using a newly developed self–expanding device: evaluation in a canine model," *Invest. Radiol.*, 30:104–109, 1995.

Prahlow et al., "Cardiac perforation due to Wallstent embolization: a fatal complication of the transjugular intrahepatic portosystemic shunt procedure," *Radiology*, 205:170–172, 1997.

Prince et al., "Local; intravascular effects of the nitinol wire blood clot filter," *Invest. Radiol.*, 23:294–300, 1988.

Punekar et al., "Post–surgical recurrent variococele: efficacy of internal spermatic venography and steel–coil embolization," *Br. J. Urol.*, 77:12–128, 1996.

Rashkind et al., "Nonsurgical closure of patent ductus arteriosus: clinical application of the Rushkind PDA occluder system," *Circulation*, 75:583–592, 1987.

Reidy and Qureshi, "Interlocking detachable platinum coils, a controlled embolization device: early clinical experience," *Cardiovasc. Intervent. Radiol.*, 19:85–90, 1996.

Sagara et al., "Recanalization after coil embolotherapy of pulmonary arteriovenous malformations: study of long term outcome and mechanisms for recanalization," *AJR*, 170:727–730, 1998.

Schmitz Rode et al., "Self–expandable spindle for transcatheter vascular occlusion: in vivo experiments," *Radiology*, 188:95–100, 1993.

Schürmann et al., "Neointimal hyperplasia in low–profile nitinol stents, Palmaz stents, and Wallstents: a comparative experimental study," *Cardiovasc. Intervent. Radiol.* 19:248–254, 1996.

Schild et al., "Effectiveness of platinum wire microcoils for venous occlusion: a study on patients treated for venogenic impotence," *Cardiovasc. Intervent. Radiol.*, 17:170–172, 1994.

Schwartz et al., "Effectiveness of transcatheter embolization in the control of hepatic vascular injuries," *JVIR*, 4:359–365, 1993.

Selby Jr., "Interventional radiology of trauma," *Radiol. Clin. N. Am.*, 30:427–439, 1992.

Sharaffuddin et al., "Repositionable vascular occluder: experimental comparison with standard Gianturco coils," *JVIR*, 7:695 703, 1996.

Sharafuddin et al., "Experimental evaluation of a new self expanding patent ductus arteriosus occluder in a canine model," *JVIR*, 7:877 887, 1996.

Simon et al., "Comparative evaluation of clinically available inferior vena cava filters with an in vitro physiologic simulation of the vena cava," *Radiology*, 189:769–774, 1993.

Sommer et al., "Use of preformed nitinol snare to improve transcatheter coil delivery in occlusion of patent ductus arteriosus," *Am. J. Cardiol.*, 74:836–839, 1994.

Taki et al., A new liquid material for embolization of arteriovenous malformations, *AJNR*, 11:163–168, 1990.

Teitelbaum et al., "Microcatheter embolization of non–neurologic traumatic vascular lesions," *JVIR*, 4:149–154, 1993.

Terada et al., "Embolization of arteriovenous malformations with peripheral aneurysms using ethylene vinyl alcohol copolymer," *J. Neurosurg.*, 75:655–660, 1991.

Tometzki et al., "Transcatheter occlusion of the patent ductus arteriosus with Cook detachable coils," *Heart*, 76:531–535, 1996.

Uzun et al., "Transcatheter occlusion of the arterial duct with Cook detachable coils: early experience," *Heart*, 76:269–273, 1996.

Vedantham et al., "Uterine artery embolization: an underused method of controlling pelvic hemorrhage," *Am. J. Obstet. Gynecol.*, 176:938–948, 1997.

Vesely et al., "Upper extremity central venous obstruction in hemodialysis patients: treatment with Wallstents," *Radiology*, 204:343–348, 1997.

Wallace et al., "Arterial occlusion of pelvic bone tumors," *Cancer*, 43: 322–328, 1979.

Wessel et al., "Outpatient closure of the patent ductus arteriosus," *Circulation*, 77:1068 1071, 1988.

White et al., "Pulmonary arteriovenous malformations: diagnosis and transcatheter embolotherapy," *JVIR*, 7:787–804, 1996.

Xian et al., "Multiple emboli and filter function: An in vitro comparison of three vena cava filters," *JVIR*, 6:887–893, 1995.

Yune, "Inferior vena cava filter: Search for an ideal device," *Radiology*, 172:15–16, 1989.

Zubillaga et al., "Endovascular occlusion of intracranial aneurysms with electrically detachable coils: correlation of aneurysm neck size and treatment results," *AJNR*, 15:815–820, 1994.

Seven photographs taken by Hideki Hyodoh of stents displayed during a Japanese metallic stentgraft meeting, Feb. 22, 1999.

*JVIR Supplement*, vol. 10, No. 2, Part 2: 284, 287. Feb. 1999.

Photograph taken by András Kónya of stent of SCVIR meeting in Orlando, Florida, Mar. 20–25, 1999.

Three photographs taken by András Kónya of poster authored by Hideki Hyodoh, András Kónya, and Kenneth C. Wright at SCVIR meeting in Orlando, Florida, Mar. 20–25, 1999.

* cited by examiner

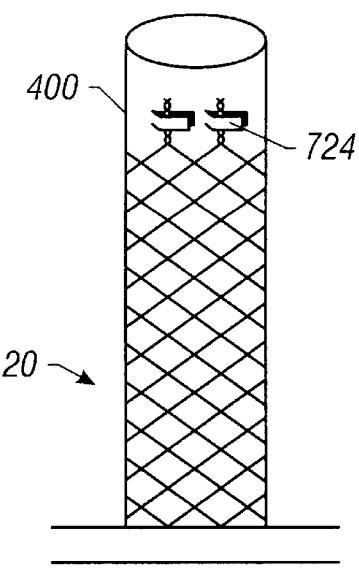 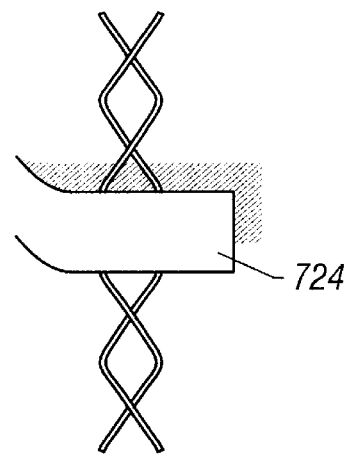
FIG. 42A  FIG. 42B
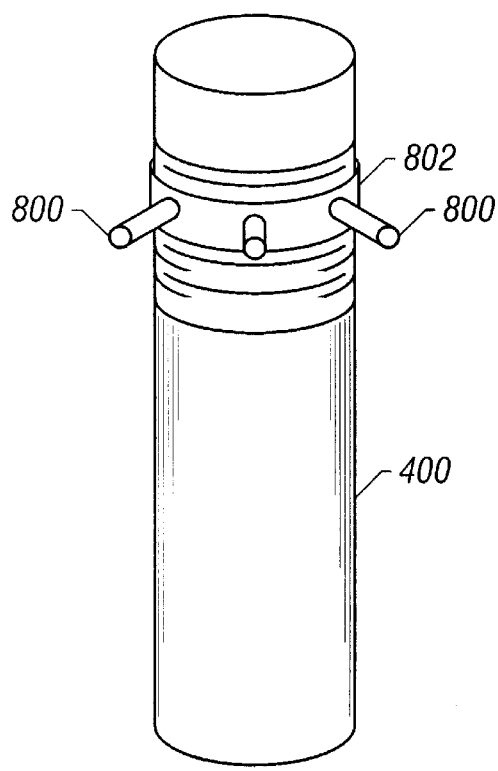 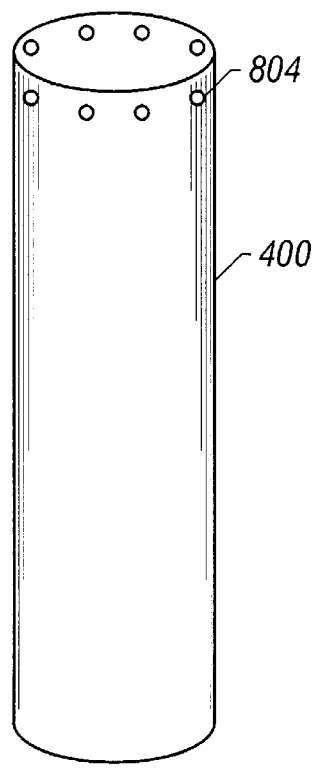
FIG. 43  FIG. 44

WOVEN BIFURCATED AND TRIFURCATED STENTS AND METHODS FOR MAKING THE SAME

BACKGROUND OF THE INVENTION

The present application claims priority to U.S. Provisional Patent Application Ser. No. 60/118,185 filed Feb. 1, 1999 and U.S. Provisional Patent Application Ser. No. 60/125,192 filed Mar. 18, 1999. The entire texts of the above-referenced disclosures are specifically incorporated by reference herein without disclaimer.

1. Field of the Invention

The present invention relates to a self-expanding bifurcated stent and apparatus and methods for inserting the same into a bifurcated anatomical structure.

2. Description of the Related Art

Numerous studies have reported the use of metallic stents for the treatment of stenotic lesions occurring in tubular anatomic structures (Wallace et al., 1986; Palmaz, 1988; Milroy et al., 1989; Günther et al., 1989; Riving et al., 1989). Placement of these stents is less invasive than surgical procedures and the stents provide more luminal space than most solid tube devices. Therefore, metallic stents have been widely used for treatment of stenotic diseases in humans. Several different types of stents have been used to treat both straight and curved lesions (Gillams et al, 1990).

The use of straight, cylindrical stents has some limitations. One major limitation is the treatment of lesions occurring at a bifurcation (Nashef et al, 1992). Many methods for stenting these lesions with straight stents have been described including side-by-side insertion (Morita, 1997), pull-through technique (Morita, 1987), creation of a T-configuration (Morita, 1987), Y-stenting (Fort, 1996), and V-stent insertion (Schampaert, 1996). However, no ideal method has been established because only straight stents with a cylindrical configuration are commercially available.

Additionally, the use of such a stent to treat disease at or near a branch of a bifurcation of a blood vessel runs the risk of compromising the degree of patency of the primary vessel and/or its branches of the bifurcation. This may occur as a result of several problems such as displacing diseased tissues, vessel spasm, dissection with or without intimal flaps, thrombosis, and embolism. For example, a bifurcated vascular or non-vascular lesion can be bridged by two straight cylindrical stents arranged in a Y-shape. One of the stents is longer forming one leg and the common trunk of the Y, while another short stent is attached to the longer one in an end-to-side fashion to form the other leg of the Y-shape. In this situation, the patency of the shorter leg is threatened by the fact that at the site of the attachment of the two stents the stent mesh of the longer stent interferes with the free flow of blood, bile, etc. Such an attachment has a high propensity for thrombosis and consequent occlusion in the vasculature, stenosis, bile congestion, inflammation, and eventually occlusion in the biliary tree. In the tracheobronchial system, mucus deposition will readily result in serious coughing, infection, and exclusion of the affected part of the lung from gas-exchange.

SUMMARY OF THE INVENTION

In one respect, the invention is a device suitable for implantation into an anatomical structure that includes, but is not limited to, a first plurality of wires that define a first leg, which has a first distal portion; a second plurality of wires that define a second leg, which has a second distal portion; and a common body that has a distal end and a proximal portion. The common body is formed from at least the first and second pluralities of wires. The proximal portion of the common body is adjacent to the distal portions of both legs, and both ends of at least one wire from one of the pluralities is located proximate (near) the distal end of the common body.

The wires in the first and second pluralities may be made from nitinol. The wires in the first and second pluralities may be made from FePt, FePd or FeNiCoTi. The wires in the first and second pluralities may also be made from FeNiC, FeMnSi or FeMnSiCrNi. The wires in the first and second pluralities may each have a diameter ranging in size from about 0.006 inches to about 0.014 inches. The first plurality of wires may include at least 6 wires. Both the legs and the common body may have tubular shapes with substantially uniform diameters. At least one of the legs of the device may be hand woven. At least one of the legs of the device may be machine woven. The device may also include a graft material attached to at least the common body. The graft material may be made from woven Dacron. The graft material may be made from polyurethane. The graft material may also be made from PTFE.

In another respect, the invention is a stent that includes, but is not limited to, a first plurality of flexible tubular strands woven to form a first leg that has a first distal portion. The flexible tubular strands in the first plurality cross each other to form a first plurality of angles. At least one of the angles in the first plurality of angles is obtuse. The stent also includes, but is not limited to, a second plurality of flexible tubular strands woven to form a second leg that has a second distal portion. The flexible tubular strands in the second plurality cross each other to form a second plurality of angles. At least one of the angles in the second plurality of angles is obtuse. The stent also includes, but is not limited to, a common body that has a common portion. The common body is formed from at least the first and second pluralities of flexible tubular strands. The common portion of the common body is adjacent to the distal portions of the first and second legs.

The flexible tubular strands in the first and second pluralities may be made from nitinol or biodegradable filaments.

In another respect, the invention is a stent that includes, but is not limited to, a first plurality of wires that define a first leg, which has a first distal portion. The stent also includes, but is not limited to, a second plurality of wires that define a second leg, which has a second distal portion. The stent also includes, but is not limited to, a third plurality of wires that define a third leg, which has a third distal portion. The stent also includes, but is not limited to, a common body that has a proximal portion and a distal end. The common body is formed from at least the first, second and third pluralities of wires. The proximal portion of the common body is adjacent to the distal portions of each of the three legs.

The wires in each of the pluralities may be made from nitinol. The first plurality of wires may include at least 5 wires. Each of the legs and the common body may have tubular shapes with substantially uniform diameters. At least one of the legs may be hand woven or machine woven. The stent may also include a graft material that is attached to at least the common body. The graft material may be made from woven Dacron. The graft material may be made from polyurethane.

In another respect, the invention is a stent that includes, but is not limited to, a first leg that has a first axis and a first end. The first leg includes, but is not limited to, a first wire that has a first segment and a second segment, which are separated by a bend in the first wire located proximate (near) the first end of the first leg. The first segment extends helically in a first direction around the first axis away from the first end of the first leg, and the second segment extends helically in a second direction around the first axis away from the first end of the first leg. The segments cross each other in a first plurality of locations. The stent also includes, but is not limited to, a second leg that has a second axis and a second end. The second leg includes, but is not limited to, a second wire that has a first segment and a second segment, which are separated by a bend in the second wire located proximate (near) the second end of the second leg. The first segment extends helically in a first direction around the second axis away from the second end of the second leg, and the second segment extends helically in a second direction around the second axis away from the second end of the second leg. The segments cross each other in a second plurality of locations. The stent also includes, but is not limited to, a common body that is formed from at least one end of each of the wires.

The first segment of the first wire may be positioned farther from the first axis than the second segment of the first wire at least one location among the first plurality of locations. The first segment of the first wire may be positioned farther from the first axis than the second segment of the first wire at each location of the first plurality of locations. The first and second wires may be made from nitinol.

In another respect, the invention is a method of creating a device suitable for implantation into an anatomical structure. The device may have a first leg, a second leg, and a common body. Each leg may have an end and a distal portion. The common body may have a proximal portion and a distal end. The method includes, but is not limited to, bending the wires in a first plurality of wires to create first bent portions in the wires. The first bent portions are arranged to define the end of the first leg. Each wire in the first plurality has two ends. The method also includes, but is not limited to, bending the wires in a second plurality of wires to create second bent portions in the wires. The second bent portions are arranged to define the end of the second leg. Each wire in the second plurality has two ends. The method also includes, but is not limited to, weaving the ends of the wires in the first plurality to create the first leg; weaving the ends of the wires in the second plurality to create the second leg; and weaving the ends of the wires in both pluralities to create the common body and the device. The proximal portion of the common body is adjacent to the distal portions of both legs.

The first bent portions may be bends or loops. The wires in the first and second pluralities may be made from nitinol. The wires in the first and second pluralities may each have a diameter ranging in size from about 0.006 inches to about 0.014 inches. The step of weaving the ends of the wires in the first plurality may be performed by hand or by machine.

In another respect, the invention is a method of creating a stent, which may have a first leg, a second leg, and a common body. Each leg may have an end and a distal portion, and the common body may have a proximal portion and a distal end. The method includes, but is not limited to, providing a weaving system that includes, but is not limited to, a first template that has first template projections, a proximal end and a distal end. The method also includes, but is not limited to, bending the wires in a first plurality of wires around the first template projections to create first bent portions in the wires. The first bent portions are arranged to define the end of the first leg. Each wire in the first plurality has two ends. The method also includes, but is not limited to, bending the wires in a second plurality of wires to create second bent portions in the wires. The second bent portions are arranged to define the end of the second leg. Each wire in the second plurality has two ends. The method also includes, but is not limited to, weaving the ends of the wires in the first plurality to create the first leg; weaving the ends of the wires in the second plurality to create the second leg; and weaving the ends of the wires in both pluralities to create the common body and the stent. The proximal portion of the common body is adjacent to the distal portions of both legs.

The weaving system may also include, but is not limited to, a second template that has second template projections, a proximal end and a distal end; and a third template that a proximal end and a distal end. The distal ends of the first and second templates may be configured to be placed within the proximal end of the third template. The step of bending the wires in the second plurality of wires may include bending the wires in the second plurality of wires around the second template projections to create second bent portions in the wires. The step of weaving the ends of the wires in both pluralities may include weaving the ends of the wires in both pluralities around the third template to create the common body and the stent.

The weaving system may also include, but is not limited to, a second template having a proximal end, a distal end, second template projections arranged around the second template proximate (near) the proximal end thereof, and an opening positioned between the proximal and distal ends of the second template. The opening is configured to accept the distal end of the first template. The step of bending the wires in the second plurality of wires may include bending the wires in the second plurality of wires around the second template projections to create second bent portions in the wires. The step of weaving the ends of the wires in the second plurality may include weaving the ends of the wires in the second plurality around the portion of the second template located proximally of the opening therein to create the second leg. The step of weaving the ends of the wires in both pluralities may include weaving the ends of the wires in both pluralities around the portion of the second template located distally of the opening therein to create the common body and the stent.

The first template projections may be pins, which may be attached to a ring engaged with the first template. The method may also include, but is not limited to, securing the wires in the first plurality of wires to the first template. The method may also include, but is not limited to, forming closed structures with the ends of the wires in both pluralities. The closed structures may be arranged to define the distal end of the common body. The method may also include, but is not limited to, heating the stent and the first template.

BRIEF DESCRIPTION OF THE DRAWINGS

The following drawings form part of the present specification and are included to further demonstrate certain aspects of the present invention. The invention may be better understood by reference to one or more of these drawings in combination with the description of illustrative embodiments presented herein.

FIG. 42A is a perspective view of a portion of the common body of a stent woven around a template having transverse tabs according to one embodiment of the present invention.

FIG. 42B is an enlarged perspective view of one of the transverse tabs and twisted wire ends depicted in FIG. 42A according to one embodiment of the present invention.

FIG. 43 is a perspective view of a template around which a ring having finish pins has been threadably engaged according to one embodiment of the present invention.

FIG. 44 is a perspective view of a template having finish holes through which finish pins may be placed according to one embodiment of the present invention.

DESCRIPTION OF ILLUSTRATIVE EMBODIMENTS

Figure 1A:
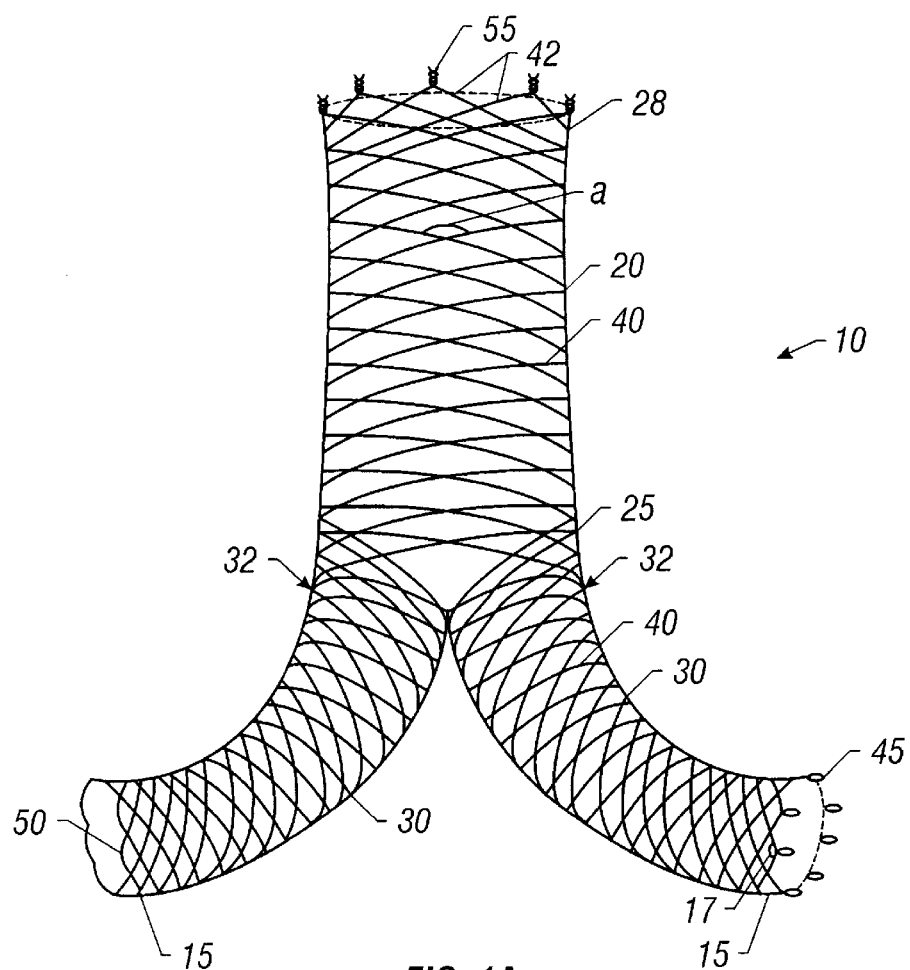
FIG. 1A is a perspective view of a bifurcated stent according to one embodiment of the present invention.
Figure 1B:
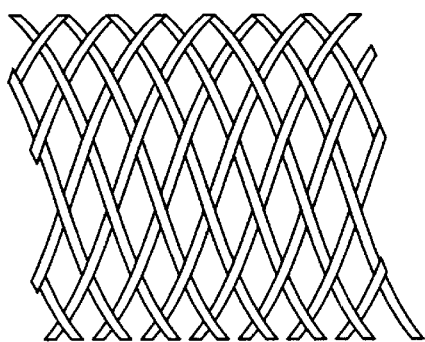
FIG. 1B is a side view of the arrangement of wires in a plain weave according to one embodiment of the present invention.

As shown in FIG. 1A, the present invention comprises a stent 10, which may include a common main body 20 and two legs 30 that comprise one coherent element. The radially expandable and flexible tubular bodies of the stent may be created by using the principle of plain weave. The arrangement of wires in a plain weave is illustrated in FIG. 1B. As will be described below in greater detail, the weave is started on two separate straight templates for making the legs 30 and is continued on a single straight template for the common body 20. The stent 10 may be made of nitinol wires and may utilize nitinol's superelastic properties. In one embodiment, the nitinol may comprise about 55–56% Nickel and about 45–44% Titanium (commercially available from Shape Memory Applications in Santa Clara, Calif.). It is to be understood that stent 10 may also be formed of any superelastic or pseudoelastic material. For example, shape memory alloys such as FePt, FePd, FeNiCoTi with thermoelastic martensitic transformation, as well as alloys such as FeNiC, FeMnSi, and FeMnSiCrNi, the shape memory effect of which relies on stress-induced martensite, may be used.

As shown in FIG. 1, ends 15 of legs 30 have a plurality of closed structures. These closed structures may be either small closed loops 45 or bends 50. Both bends 50 and small closed loops 45 may be formed by bending a wire 40 at a selected point located between the bends of the wire. For most applications, the selected point of the bend or small closed loop may be close to the mid-point of wire 40. The closed structures are advantageous, because, for example, the closed structures formed by bending are less likely to cause damage such as perforations or penetrations to the tubular structure stented than are free wire ends.

Moreover, both loops 45 and bends 50 provide many significant advantages, some of which are unexpected, over woven devices such as the stent disclosed in U.S. Pat. No. 4,655,771 to Wallsten (1987) (hereinafter, the stent therein will be referred to as the "WALLSTENT"), which is hereby expressly incorporated herein by reference, which have free wire ends. For instance, the Wallsten patent recognizes that the free wire ends of the WALLSTENT should be protected, implicitly acknowledging the potential tissue-damaging dangers such free, sharp wire ends pose. The Wallsten patent suggests methods by which one can attempt to lessen these dangers, such as connecting the free wire ends to each other by attaching U-shaped members to them through heat welding, gluing or the like. These suggested methods are likely time-consuming and, as a result, expensive. No such steps need to be taken in creating either loops 45 or bends 50 of the present woven bifurcated stents as will be discussed below in greater detail.

Further, the connections resulting from the methods disclosed in the Wallsten patent are likely more prone to mechanical failure than are loops 45 or bends 50 of the present woven bifurcated stents. For example, welding can introduce anomalies such as cracks (which may result from the non-uniform solidification, uneven boundaries, etc.); voids or other irregularities resulting from porosity; inclusions (which include slag, oxides, etc.); etc., into the welded metal that create stress concentrations and dramatically increases the propensity for the welded connection to fail at those locations. In contrast, the gentle curves and bends resulting in loops 45 and bends 50 are virtually free of any such induced stresses and, as a result, are much less likely to fail.

The Wallsten patent also suggests gluing the free wire ends, a method that provides even less structural integrity than can welding, because the resulting bond between the joined wire ends is only as strong as the surface tension between the glue and the metal used. Consequently, the joint created is more prone to failure than a welded joint suffering from the anomalies just discussed.

Similarly, the Wallsten patent discloses first utilizing electric resistance heating to weld together the points of crossing of the free wire ends in a ring around the stent and then folding the free wire ends extending beyond the welded ring inwardly with light plastic deformation through controlled heating. This method involves not only the likely introduction of the anomalies discussed above that can result from welding, it also involves an additional stress on the joints created as the free wire ends are folded inwardly while being heated. Thus, this preferred joint is similar to the glued joint in that it is likely even more prone to failure than one involving only welding.

In sum, the gentle curves and bends that may be used to create loops 45 and bends 50 of the present woven bifurcated stents provide devices with safer ends: no free wire ends exist that may unintentionally penetrate and damage the wall of the structure into which they are delivered; bends 45 or loops 50 are much less likely to mechanically fail than are the free wire ends that are connected together using welding or glue; and the likely time-consuming task of creating multiple welded or glued joints does not exist. Further, while the closed structures 55 (discussed below in greater detail) may be reinforced using methods similar to those suggested by the Wallsten patent (i.e., such as by welding), the present woven bifurcated stents have fewer potential locations for using such methods as either bends or loops exist at the ends of the legs of the present stents (this is especially true considering fewer wires are generally needed for making the legs of the present stents than are needed for making comparably-sized WALLSTENTS, even equating one of the present wires to two wires as those are used in the WALLSTENT). As a result, the potential for mechanical failure of the present woven devices is reduced accordingly.

In addition to the foregoing benefits, loops 45 and bends 50 also provide advantages over the modified free wire ends disclosed in the Wallsten patent discussed above that are unexpected. For example, the inventors have found that the mesh of one of the legs of present woven bifurcated stents may be formed from fewer wires than can the mesh of a comparably-sized WALLSTENT (even equating one of the present wires to two wires as those are used in the WALLSTENT). Accordingly, the expansile force of one of the legs of present woven bifurcated stents of a given size may be maintained with fewer wires than would be needed to maintain the same expansile force of a WALLSTENT of the same size by simply increasing the mesh tightness (i.e., by increasing angle a in FIG. 1, discussed below in greater detail). Similarly, the inventors have found that the same result may be achieved by increasing the diameter of the present wires with or without adjusting the mesh tightness. As a result, the amount of metal needed for the legs of present woven bifurcated stents may be less than what is needed in another comparably-sized woven stent, such as the WALLSTENT. This reduction in necessary metal translates to a cost savings, and also means that patients are less likely to experience thrombosis and/or restenosis. As a further result, the variety of sizes that may be created for legs of the present woven bifurcated stents and the variety in the tightness of the weave of each is virtually unlimited, thereby facilitating virtually all potential applications.

Further, the inventors also discovered that virtually no shortening occurs while bending the present woven bifurcated stents, nor do the diameters of the legs or the common body of the present woven bifurcated stents increase during bending. Thus, it is easier to accurately and predictably position the present woven bifurcated stents in a tortuous anatomy than it is to position other woven stents that shorten more or suffer larger increases in diameter when bent, such as the WALLSTENT. For example, a tightly-woven leg of the present bifurcated stent, 2.5 cm long measured from the end of the leg to the start of the common body (see FIG. 1A), 10 mm in diameter, formed from 10 0.006-inch wires may be maximally bent by bringing end 15 of the leg toward the location at which it meets common body 20, and no shortening or diameter increase occurs during maximal bending. In contrast, for a WALLSTENT formed from 24 0.005-inch wires to behave similarly, the inventors found that it should be 6 cm long and 9 mm in diameter; although, when manipulated in a similar manner, the WALLSTENT experienced a 10% increase in diameter and some shortening. Thus, the length-to-diameter ratios of the foregoing stents were 2.5 and 6.6, respectively.

At least 5 wires (the number of wires used being designated by n) may be used in the plurality of wires that form each leg 30 of the stent 10. The number of wires that form each leg 30 may vary. As shown in FIG. 1A, the wires 40 used to form the legs and common body of stent 10 cross each other in a multiple locations at multiple angles. The angles between the crossing wires are preferably obtuse, i.e. more than 90° (see angle a in FIG. 1A). However, it will be understood that acute angles may be utilized. In an exemplary embodiment, the angle may typically be about 150° for applications such as the aorto iliac. In another exemplary embodiment, the angle may typically be about 160° for applications such as the biliary tree (e.g., for tumorous lesions). In another exemplary embodiment, the angle may be typically about 170° for applications such as the superior vena cava (e.g., for space occupying lesions). Angle a should be increased as the desired radial (i.e., expansile) force of the legs and common body of the bifurcated stent increases. Further, the radial force of the legs and common body of the bifurcated stent may generally be increased by increasing the diameter of the wires used. Thus, angle a may be held constant while the diameters of the wires used are increased and, as a result, the radial force of the legs and common body of the bifurcated stent increase. The weave is contiguous, meaning that the weave of the common body is formed from the weaves of the two legs, and from the level of the proximal end 25 of the common body 20 (the bifurcation), 2n wires (assuming the same number of wires are used to form each leg) are used to form the common body 20 of the stent 10. As shown, the distal portions 32 of the legs 30 are positioned adjacent to the proximal end 25 (and hence the proximal portion) of common body 20. At the distal or top end 28 (stent crown) of the common body 20, adjacent wire ends 42 may be coupled together (as described below) to form closed structures 55. Because common body 20 is formed from at least the wires making up legs 30, both ends of at least one wire from each of the legs is located proximate distal end 28 of common body 20. Wires 40 may range in diameter from about 0.005 inches to about 0.015 inches, depending on the application.

As used herein, the terms "distal" and "proximal" are relative terms only. The inventors do not intend to impart any limitations of any kind through their use. For example, as discussed above with respect to FIG. 1A, end 25 of common body 20 is described as "proximal" while end 28 of common body 20 is described as "distal." In this context, as in all other contexts herein, these terms only indicate relative proximity to either the viewer of the figure, the operator of the delivery device on which the stent is mounted, or the like. Accordingly, because end 25 is closer to the viewer of FIG. 1A than is end 28, end 25 is described as being "proximal" and end 28 is described as being "distal." Similarly, with respect to the discussion below pertaining to FIG. 5, the orientation of stent 10 has been reversed in FIG. 5 from its orientation with respect to the viewer depicted in FIG. 1A. Accordingly, as stated below with regard to FIG. 5, sheath 190 may be oriented over the "proximal" end of the stent—the same end that is described as "distal" end 28 with respect to FIG. 1A.

Figure 1C:
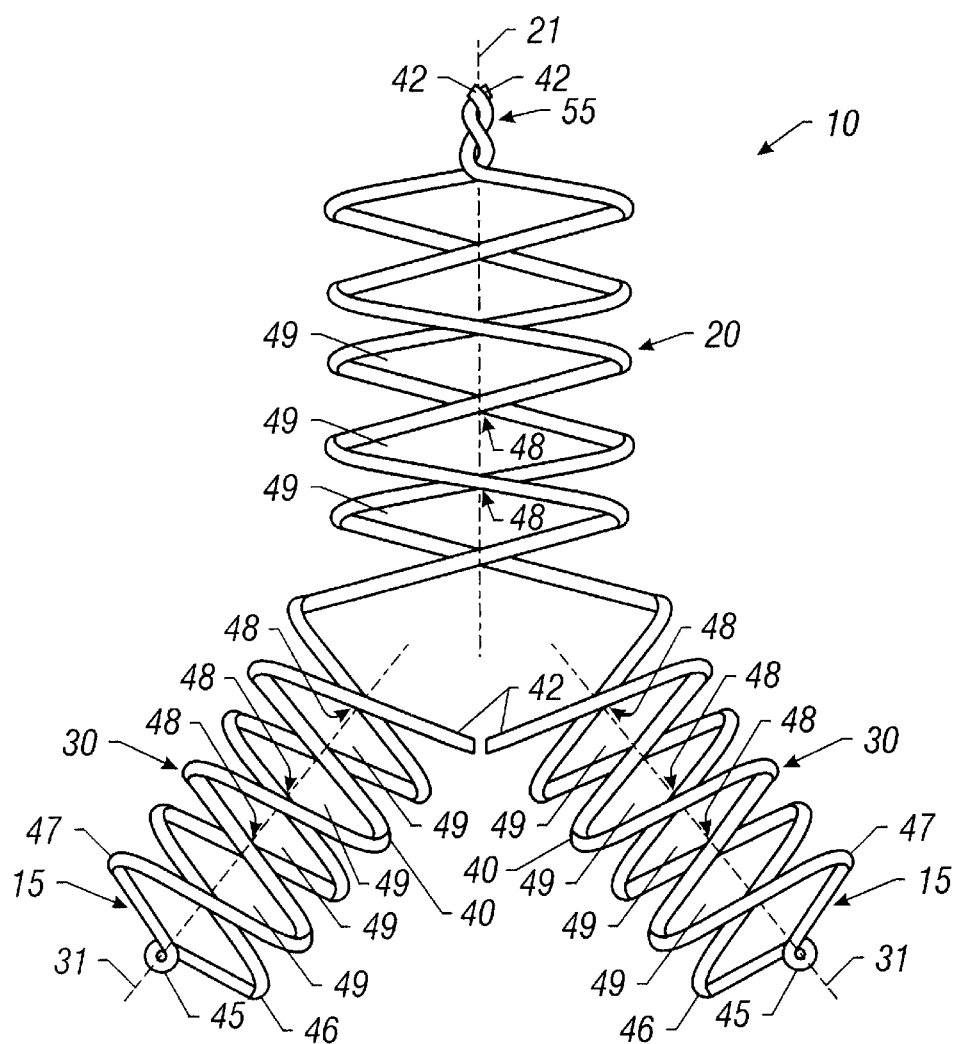
FIG. 1C is a front view of a bifurcated stent formed from two wires according to one embodiment of the present invention.

Bifurcated stent 10 may also be formed from two wires. As illustrated in FIG. 1C, legs 30 have axes 31, and ends 15 (which may be termed proximal ends). Each leg is shown as being formed from a single wire 40. First segments 46 of wires 40 are separated from second segments 47 of wires 40 by bends in the wires (in the shape of loops 45, but which may also be bends 50), which are located proximate ends 15 of legs 30. As shown in FIG. 1C, first segments 46 extend helically in a first direction around axes 31 away from ends 15 of the legs. Similarly, second segments 47 extend helically in a second direction around axes 31 away from ends 15 of the legs. First segments 46 cross second segments 47 in a plurality of locations 48. As shown in FIG. 1C, locations 48 define loops 49, which touch each other such that the loops are contiguous. Loops 49 are " contiguous" because, with the exception of the first and last loops, each loop shares a point—location 48—with two other loops.

In further reference to FIG. 1C, ends 42 of second segments 47 are shown as being located proximate the distal portions of legs 30 and proximate the proximal portion of common body 20. These ends 42 may be left free (as shown) or may be may be coupled together (as described below but not shown) to form closed structures. Ends 42 of first segments 46 are shown in FIG. 1C as forming common body 20. First segments 46 may be arranged about axis 21 of common body 20 in the same manner that the first and second segments of the wires forming legs 30 may be arranged around axes 31. In this regard, first segments 46 cross each other in a plurality of locations 48. As with legs 30, locations 48 define loops 49, which touch each other such that the loops are contiguous. Ends 42 of first segments 46 may be coupled together to form closed structure 55.

First and second segments 46 and 47 may be arranged in different ways with respect to each other about axes 31. As shown in FIG. 1C, first segments 46 are positioned farther from axes 31 than second segments 47 at alternate locations 48. Although not shown, it will be understood to those of skill in the art, with the benefit of this disclosure, that first segments 46 may be positioned farther from axes 31 at each location 48. The same is true of first segments 46 with respect to axis 21.

In the embodiment of stent 10 depicted in FIG. 1C, loops 49 reside in a series of planes that includes two groups of planes (not shown) for each leg 30 and for common body 20, one of which includes the planes passing through the first, third, fifth, etc. loops 49, and the other of which includes the planes passing through the second, fourth, sixth, etc. loops 49. The planes in each group are roughly parallel to each other. Additionally, when body 10 is in its unconstrained state, the planes in one of the groups intersect the planes in the other group (whether it is a leg or a common body in question) at acute angles that fall within the range of slightly greater than 0° to about 45°. Moreover, axes 31 and 21 pass generally through the center of each of loops 49 for either the legs or the common body of stent 10.

Figure 11:
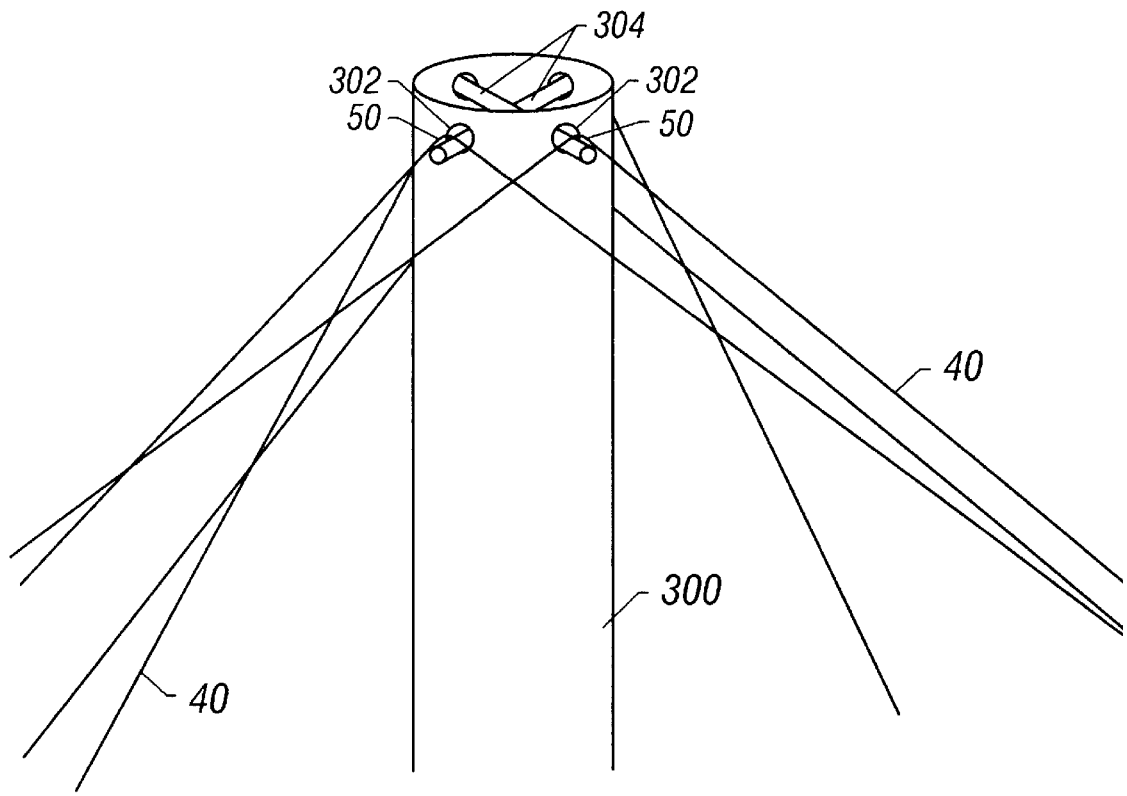
FIGS. 11–19 show stages in a hand weaving method according to one embodiment of the present invention.

In an exemplary embodiment, legs 30 of stent 10 may be formed by various methods of plain weave including hand weaving and machine weaving. The following process is an exemplary embodiment of plain weaving according to the present invention. As shown in FIG. 11, a template 300 having a diameter corresponding to the chosen diameter of the leg of the stent is provided. The top of the template is equipped with holes 302 around its circumference. Pins 304 are placed through the holes such that they extend beyond the outer surface of the template on opposing sides. As shown in FIG. 11, wires 40 are bent at about their midpoint around the pins. The bend may result in the formation of bends 50 as shown, or the wires may be wrapped around the pins to form small closed loops 45 (not shown). In one embodiment of leg 30, angle 17 of small closed loop 45 or bend 50 (FIG. 1A) may be less than 90°. In a more typical embodiment of leg 30, angle 17 may be equal to or greater than 90°, and may approach, but not include, 180°.

Although only two pins are shown in FIG. 11, it is to be understood that this is done for illustrative purposes only, and not to indicate the appropriate number of wires to use in any given application. In an exemplary embodiment, template 300 is typically formed of brass or copper, but may be formed of any suitable material capable of withstanding the cure temperature discussed below, such as stainless steel. Similarly, in an exemplary embodiment, pins 304 are typically formed of stainless steel, but may be formed of any similarly suitable material. It is to be understood that the pins may be supported by the template by any suitable means capable of withstanding the cure temperature, including preforming, attachment by welding, threading, or the like.

Figure 12:
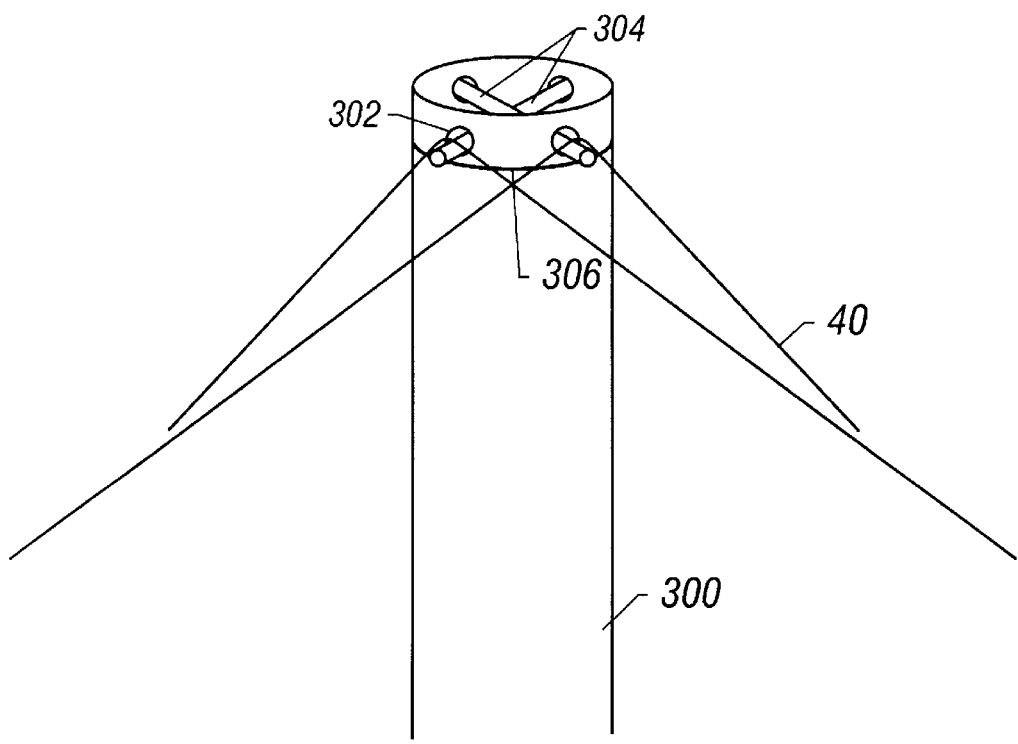

As shown in FIG. 12, after the wires have been bent around the pins, the wires are secured to the template to prevent them from returning to their original, straight, unbent position. This may be necessary given the superelastic nature of wires such as nitinol and the like (discussed below). As shown in FIG. 12, wires 40 are secured by securing wire 306 around the outside of wires 40 so as to secure wires 40 against the outside of the template. In an exemplary embodiment, copper is typically used for securing wire 306, but it is to be understood that any suitable wire capable of withstanding the curing temperature of about 500° C. discussed below may be used. After the wires are secured, small weights 360 (shown in FIG. 15) are attached to the free ends of the wires using any suitable means such as tying, or the like. In an exemplary embodiment, weights with masses of approximately 50–100 grams may typically be used with wires having diameters of between about 0.005 inches and about 0.011 inches. However, it is to be understood that weights of different masses may chosen so long as the wires are kept under tension (i.e. straight) during plain weaving (as described below), and properly balance the central weight (described below).

Figure 13:
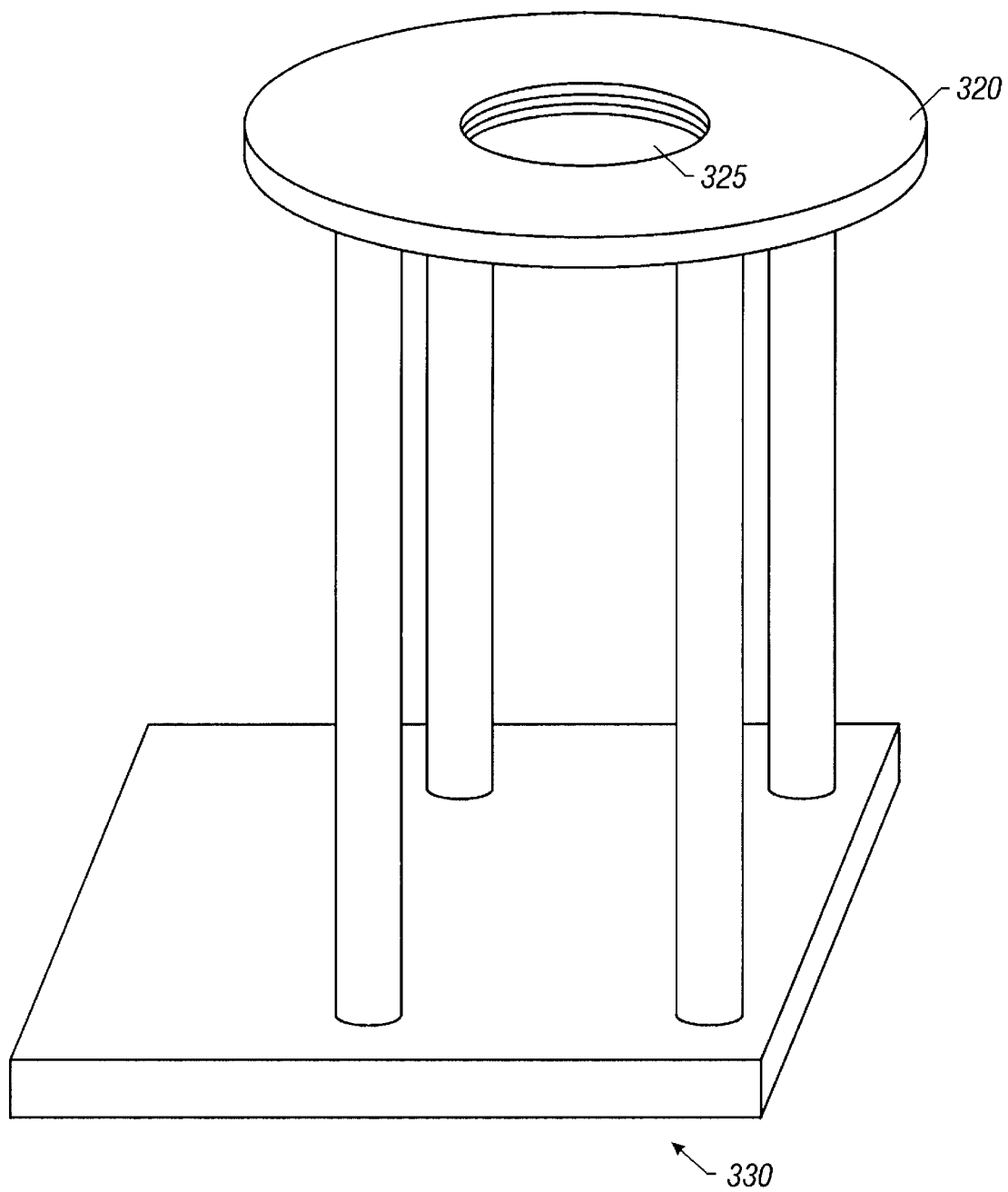
Figure 23:
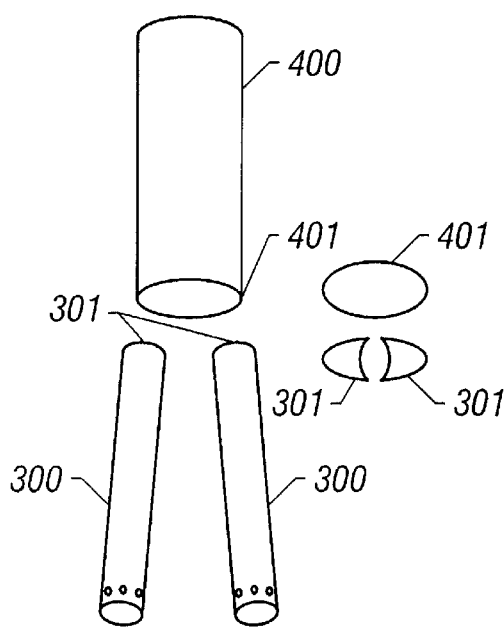
FIG. 23 is a perspective view of the templates for a bifurcated stent according to one embodiment of the present invention.
Figure 24:
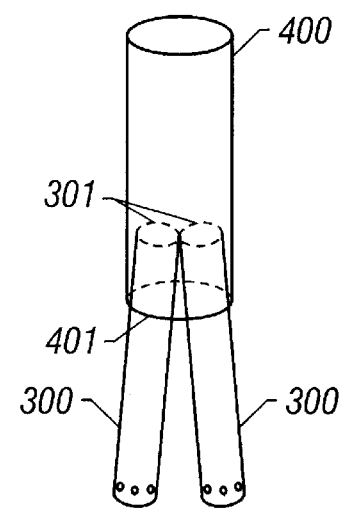
FIG. 24 is a perspective view of the templates for a bifurcated stent in an assembled position according to one embodiment of the present invention.
Figure 25A:
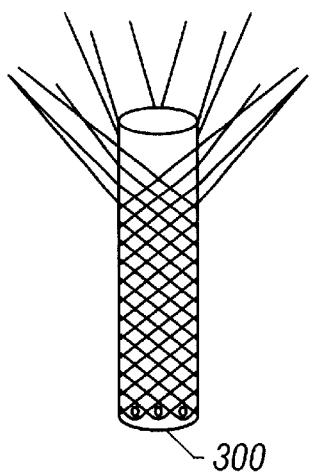
FIGS. 25A–C is a perspective view of wires woven on leg templates that are then attached to a common body template on which the weaving continues according to one embodiment of the present invention.
Figure 25B:
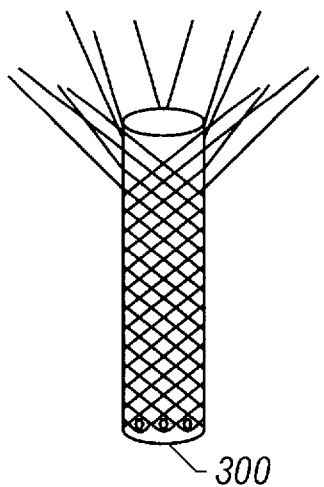
Figure 25C:
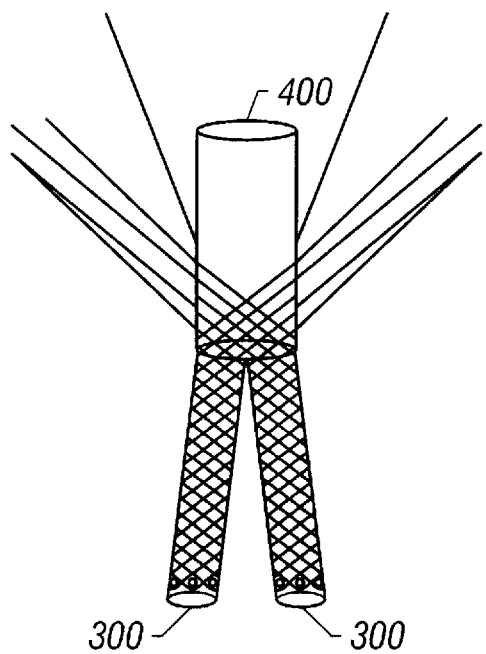

As shown in FIG. 13, a stand 330 with a circular plate 320 is provided with an opening 325. The diameter of the opening may depend on the diameter of the template. In an exemplary embodiment, an opening with a diameter of about 4.5 cm may be typically utilized in conjunction with a template having a diameter of about 1.0 cm. It is to be understood, however, that an opening with a diameter more closely corresponding to the diameter of the template may be utilized. It is also to be understood that templates 300 may have slightly "D-shaped" ends 301 in order to facilitate placement within the template 400 for the common body as shown in FIG. 23.

Figure 14:
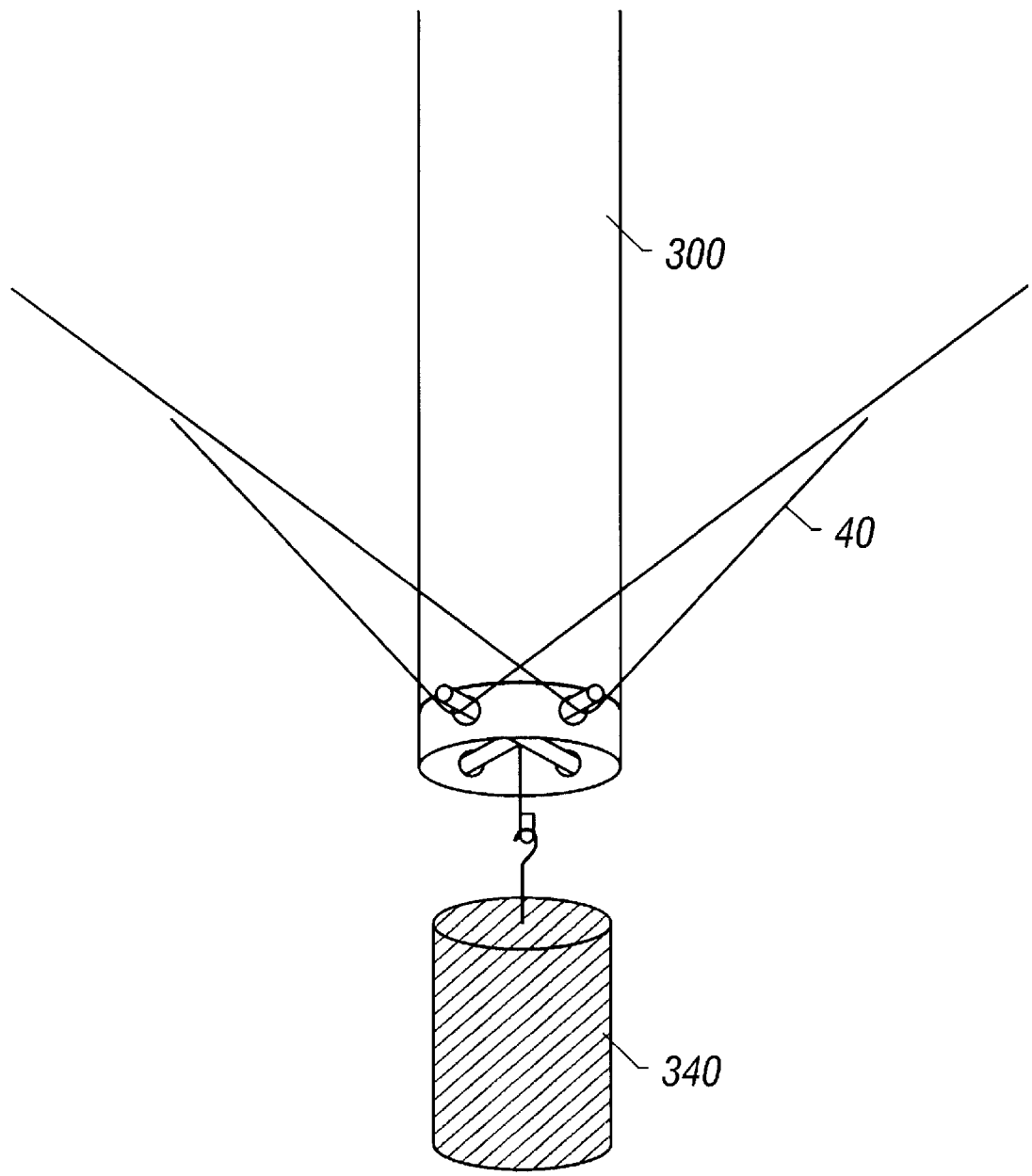

As shown in FIG. 14, before or after the weights are attached to the ends of wires 40, the template is inverted. In an exemplary embodiment, the weights may be typically attached to the free ends of the wires prior to inversion of the template such that the wires are kept under tension and may be prevented from returning to their unbent, nominal state. A central weight 340 may then be attached to the end of the template. In an exemplary embodiment, the central weight may have a mass of approximately 600 grams, and may typically be hung from the pins. However, it is to be understood that a central weight weights of a different mass may chosen so long as the wires are kept under tension (i.e. straight) during plain weaving (as described below), and properly balance the smaller weights (described above). The central weight may be attached to the template's end in any suitable manner, such as hanging from holes in the template itself, etc.

Figure 15:
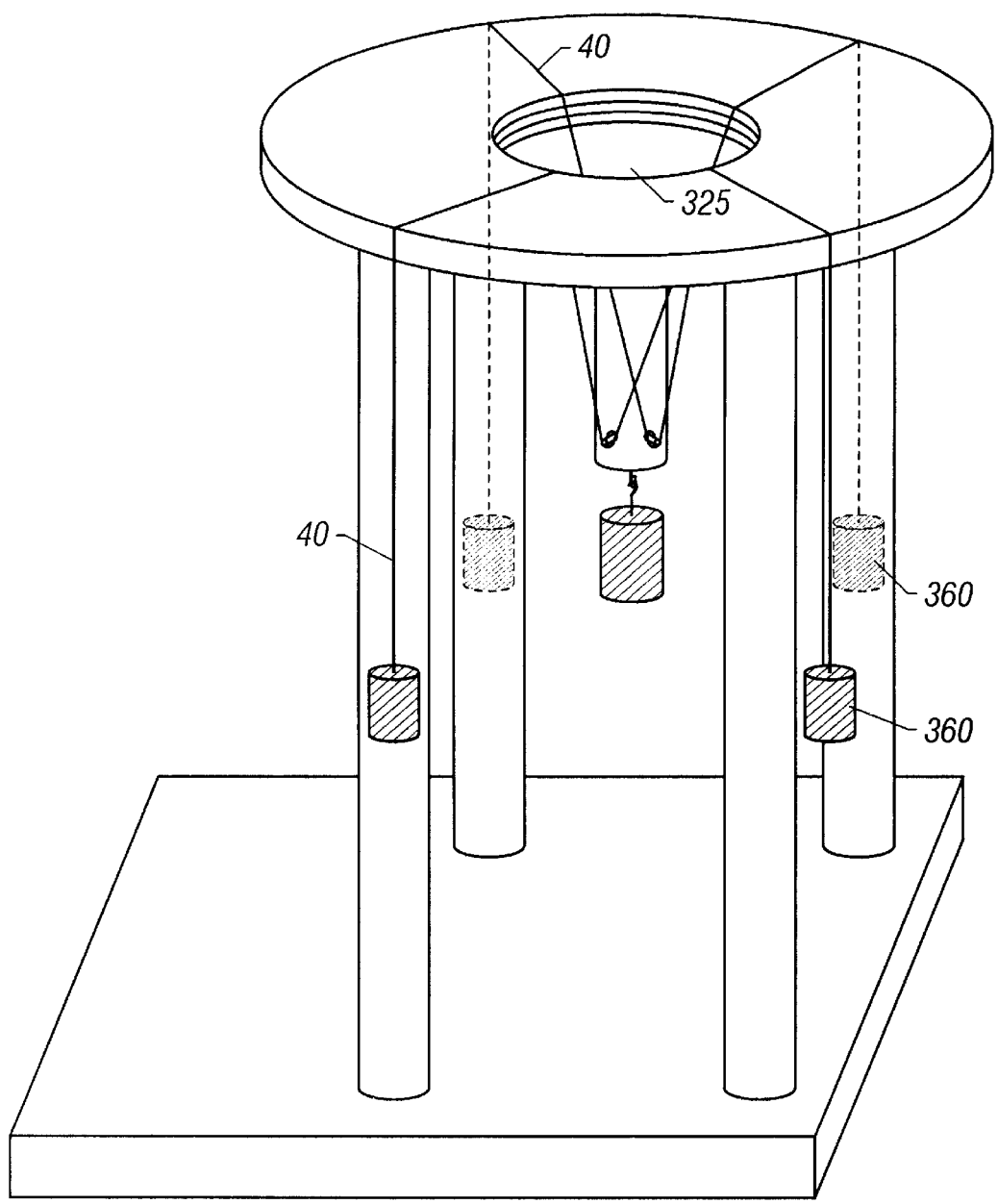
Figure 16:
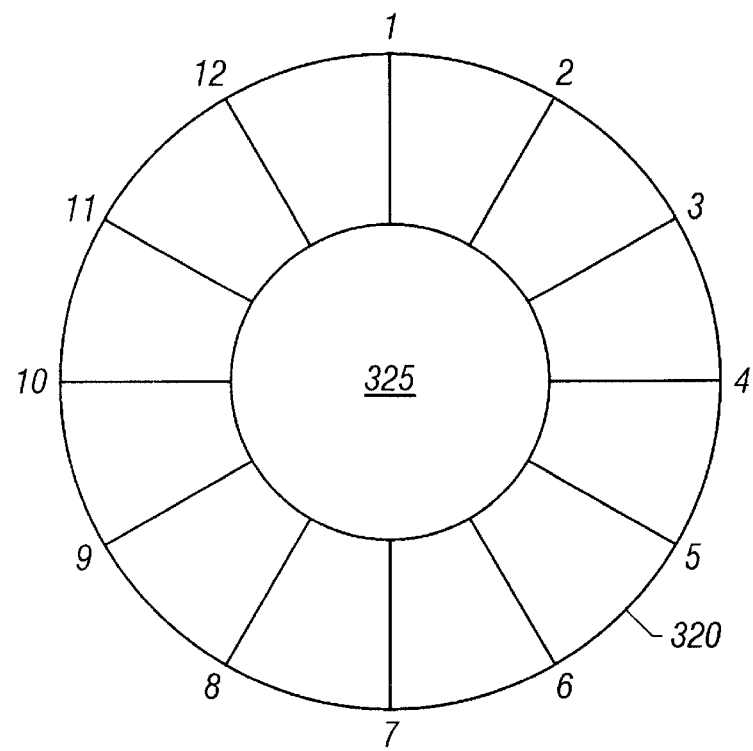

Before or after central weight 340 is attached to the end of the template, the inverted template is placed through opening 325, as shown in FIG. 15. In an exemplary embodiment, the central weight may typically be attached to the inverted template after the inverted template is placed through opening 325. As shown in FIG. 15, the wires 40 may be arranged fairly evenly around the circumference of the circular plate. As shown in FIG. 16, in an exemplary embodiment of the present invention, 6 wires having 12 ends numbered 1–12 (each wire having 2 ends) are shown as being arranged in a substantially symmetrical fashion around circular plate 320. The weights 340 and 360 typically serve to keep the wires under tension and in balance. Next, the plain weaving may take place.

Figure 17:
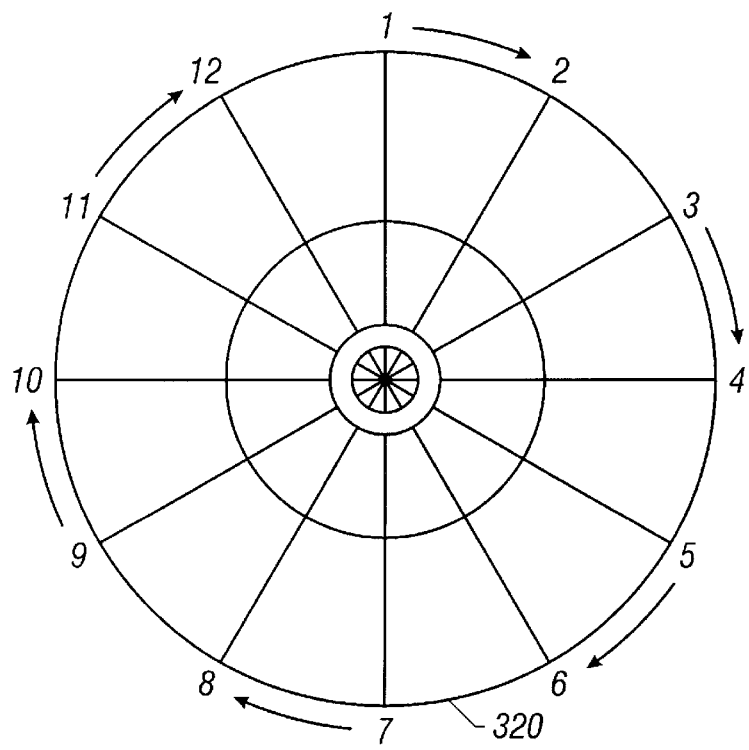
Figure 18:
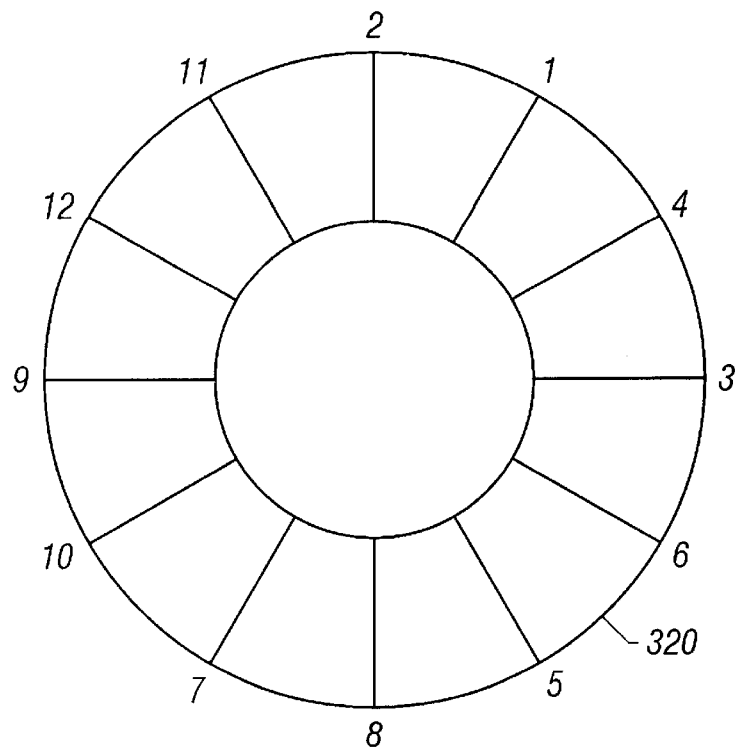
Figure 19:
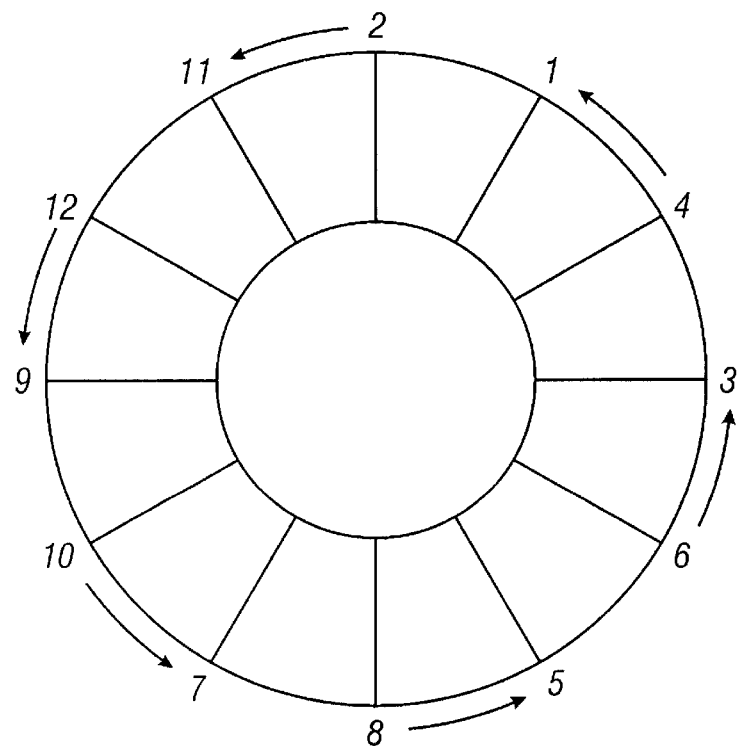

In the manner shown in FIG. 17, the weave may be started by crossing one wire end over the adjacent wire end. This crossing may be made in either a clockwise or counterclockwise fashion. This crossing may be carried out as directed by the arrows shown in FIG. 17. After a complete set of crosses (or one "turn") has been carried out, the location of the crossed wire ends is as shown in FIG. 18. In an exemplary embodiment, the resulting location of the wire ends may be achieved by crossing one wire end over another in one direction while slightly shifting the wire end not crossed in the opposite direction. In an exemplary embodiment, for example, this shifting may be about 15°. Thus, wire end 1 may be crossed in a clockwise direction over wire end 2, while shifting wire end 2 about 15° counterclockwise. Once one turn has taken place, crossing may begin in the same fashion, but in the opposite direction, as shown in FIG. 19. This process may be repeated until the plain weave is complete.

The tightness of the wire mesh (i.e., the angle a between the wires—FIG. 1A) may be adjusted by changing the central weight. An increase in the central weight results in a looser weave (decreased angle a between the wires) and vice versa.

The other leg of the stent is also woven in the same fashion.

In an exemplary embodiment of the plain weave process of legs 30 according to the present invention, a conventional braiding machine may be utilized to arrange wires 40 in a plain weave to form legs 30 of stent 10. In another embodiment, a conventional braiding machine may also be used to arrange wires in a plain weave to form the common body of a trifurcated stent (described below). Such a braiding machine may be obtained, for example, from Wardwell Braiding Machine Company in Central Falls, R.I. The manner in which a plain weave may be achieved using a conventional braiding machine is displayed in FIG. 7 of U.S. Pat. No. 5,419,231 to Earle, III et al. (1995), which is hereby expressly incorporated by reference, as well as in FIG. 1 of U.S. Pat. No. 5,485,774 to Osborne (1996), which is hereby expressly incorporated by reference.

Once the two legs have been woven, the templates 300 may be assembled with a template 400 for the common body as shown in FIGS. 24 and 25A–C. The weaving is then continued in the same manner around the common body template. The only difference being that the number of wires being woven has doubled. Or, if the number of wires in the pluralities of wires used to form the respective legs of the stent is different, the number of wires in the plurality of wires that are woven to form the common body includes the wires from both of the pluralities of wires used to form the legs. As indicated in FIGS. 23–25C, in an exemplary embodiment according to the present invention, template 400 may be generally cylindrical in shape. In such an embodiment, the shape of a short portion of template 400 near end 401 into which the two leg templates may be placed may be generally elliptical for a short portion. It is to be understood, however, that a common body having a consistently cylindrical shape may also be used.

Figure 26:
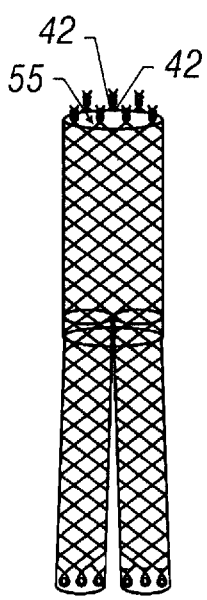
FIG. 26 is a perspective view of a bifurcated stent woven on an assembled bifurcated template according to one embodiment of the present invention.

After the weaving of the common body is complete, the adjacent wire ends 42 (FIG. 1A) may be coupled together to form closed structures 55 in any suitable fashion capable of withstanding the heating described below, and capable of restraining the wires from returning to their straight, unbent configuration as indicated in FIG. 26. In one embodiment, the wire ends may be coupled together utilizing at least two twists as shown in FIG. 26. In one embodiment, 6 twists may be used. Regardless of the number of twists used, it is preferable to keep the twisted wire ends as short as possible. The shorter the twisted wire ends are kept, the more resistant to bending the twisted wire ends are. As a result, the twisted wire ends will be less likely to be inadvertently displaced during insertion, positioning, repositioning, or retrieval, thus reducing their potential for causing tissue damage. In other embodiments, the wire ends may be coupled together by bending or crimping a metal clip around the wire ends, by tying the wire ends together with any suitable material such as stainless steel wire, by welding, etc.

Other configurations of template 400 may also be utilized consistently with the present disclosure. For example, template 400 may be provided with pins around which the wire ends may be twisted in fashioning closed structures 55. Finish pins 800 may be supplied on a ring, such as ring 802 depicted in FIG. 43, in any suitable fashion, including, for example, through removable or permanent attachment. Ring 802 may be configured to threadably engage template 400 as depicted in FIG. 43. In other embodiments, ring 802 may be configured to engage template 400 by virtue of frictional forces (not shown) or may be configured to be secured to template 400 as would a clamp (not shown). Finish pins 800 may also be engaged with template 400 in the same manner that pins 304 are engaged with template 300. As shown in FIG. 44, in such an embodiment, template 400 may be provided with finish holes 804 similar to holes 302, and finish pins 800 may be placed through finish holes 804. Ring 802 may also be utilized in place of holes 302 and pins 304.

In an embodiment in which finish pins 800 are engaged with template 400 through the utilization of ring 802, the number of finish pins utilized may be equal to the number of wires that are used to form both legs. Template 400 may be threaded along any portion of its length so as to best accommodate a variety of common body sizes. For example, only a portion of template 400 may be threaded, as depicted in FIG. 43. Threads need not be utilized with a ring that engages template 400 by virtue of frictional forces.

An advantage afforded by the use of ring 802 is the ease with which the precise length of common body 20 may be achieved through the adjustment of the position of ring 802. Further, the use of ring 802 also facilitates the symmetrical alignment of finish pins 800 with the longitudinal lines formed by the points at which the wire segments cross each other within the weave such that the symmetry of the weave may be maintained and any structural benefits stemming from that symmetry may be realized.

In an embodiment in which finish pins 800 are placed through finish holes 804, the number of finish pins utilized may be equal to one-half of the number of wires that are used to form common body 20, since both ends of the finish pins will be utilized. Template 400 may be provided with finish holes 804 along any portion of its length so as to best accommodate a variety of stent sizes. For example, only a portion of template 400 may be provided with finish holes 804, as depicted in FIG. 44. As with ring 802, the use of finish holes 804 advantageously allows the user to easily and precisely achieve a given length for common body 20.

With the finish pins in place, once the wire ends of the wires have been woven around the common body template, the wire ends may be secured around the finish pins in any suitable manner to form closed structures, including by twisting, bending, wrapping and the like. In one embodiment, the wire ends may be crossed, then bent around a finish pin and then secured together with a short piece of thin-walled metal tubing. Such a joint may then be reinforced by soldering, welding, or the like. A suitable number of additional twists may be utilized after securing the wire ends around the finish pins in forming closed structures. Securing wires (see securing wire 306 depicted in FIG. 12) may be utilized to secure the closed structures to the common body template during annealing.

As a result of securing the wire ends around the finish pins, the angle created between the crossed wire ends may be similar, if not identical to, the angle of the other crossed wires in the woven legs described above. Advantageously, by using finish pins, this angle between the crossed wire ends may be maintained, preventing the weave of the woven stent from loosening. Were loosening to occur, the expansile or radial force of the portion of the stent with the loosened weave could decrease, causing that portion of the stent to remain elongated within the structure in which it is placed. Therefore, through the use of finish pins and as a result of the correlating maintenance of the angle between the crossed wire ends that are wrapped or twisted around the finish pins, the tightness of the weave along the length of the legs and common body of the stent—from end to end—may be consistent and resistant to loosening. Further, the expansile force of the end of the stent having closed structures (i.e., the distal end of the stent) may be comparable to the expansile force of the other portions of the stent.

Figure 31:
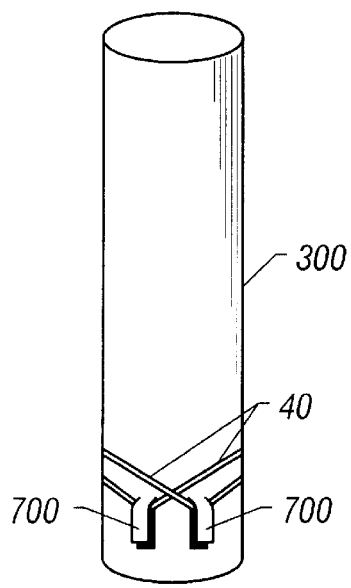
FIG. 31 is perspective view of a template with longitudinal tabs around which wires are bent according to one embodiment of the present invention.

Another method of forming legs 30 of stent 10 and ultimately stent 10, according to the present invention, is illustrated in FIGS. 31–42B. As shown in FIG. 31, the base of template 300 may be equipped with longitudinal tabs 700 formed by two longitudinal cuts connected by a transverse cut. The length of the cuts may be determined based upon the size of the template chosen. For example, a template that is about 10 mm in diameter may have longitudinal tabs with longitudinal cuts about 4 to 5 mm long, and the connecting transverse cuts may be about 2 mm long. As illustrated in FIGS. 31, tabs 700 may be slightly elevated from the surface of template 300 and may be positioned symmetrically around template 300.

Figure 32A:
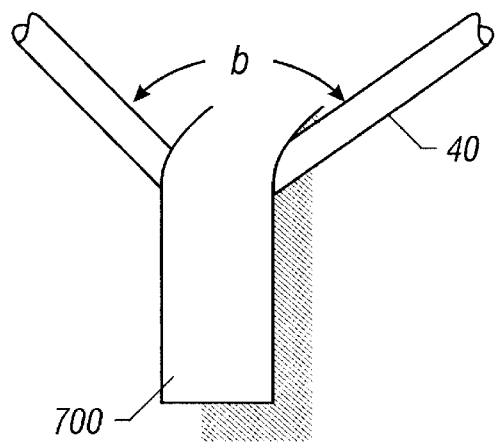
FIG. 32A is an enlarged perspective view of the longitudinal tab and bent wire depicted in FIG. 31 according to one embodiment of the present invention.
Figure 32B:
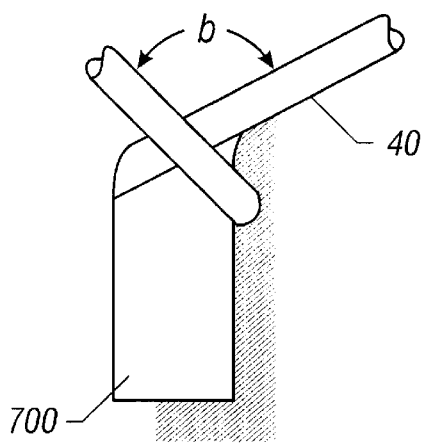
FIG. 32B is an enlarged perspective view of a longitudinal tab depicted in FIG. 31 around which a wire is bent to form a loop according to one embodiment of the present invention.

FIGS. 31 and 32A and B also illustrate that wires 40 may be bent around tabs 700 at selected points located between the ends of the wires to form bent portions along wires 40. The bent portions may take the form of bends 50, as shown in FIG. 32A, or may be further wrapped around tabs 700 to form loops 45, as shown in FIG. 32B. Angle b of bends 50 or loops 45 may be less than 90°. In a more typical embodiment of the legs of the present stents, angle b may be equal to or greater than 90°, and may approach but not include, 180°. The bent portions may be arranged to define the ends of the legs. The ends of the wires may then be weaved to create the legs using, for example, the following machine weave method.

Figure 33:
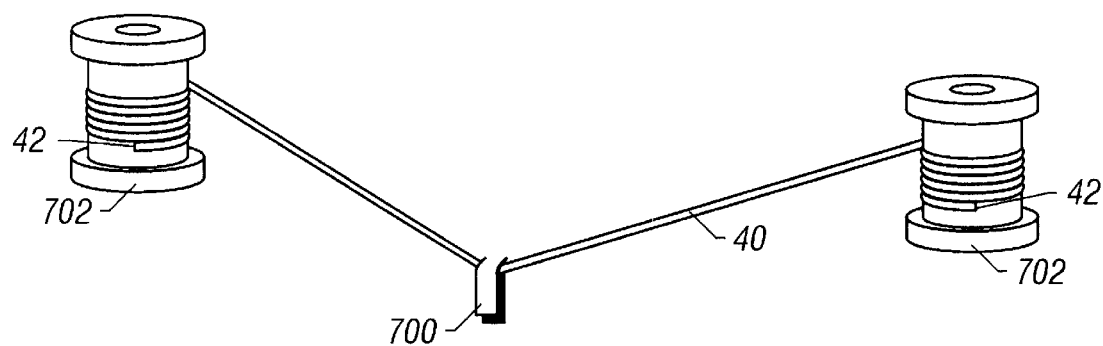
FIG. 33 is a perspective view of a wire bent around a longitudinal tab and wrapped around a pair of bobbins according to one embodiment of the present invention.

As shown in FIG. 33, the ends 42 of each wire 40 may be arranged around a pair of bobbins 702. The length of the wire wound around each bobbin may be determined by considering the total length of the wire needed to form the leg as well as the wire length needed to arrange the bobbins around the weaving plates (shown in FIG. 34), which are discussed below in greater detail.

Figure 34:
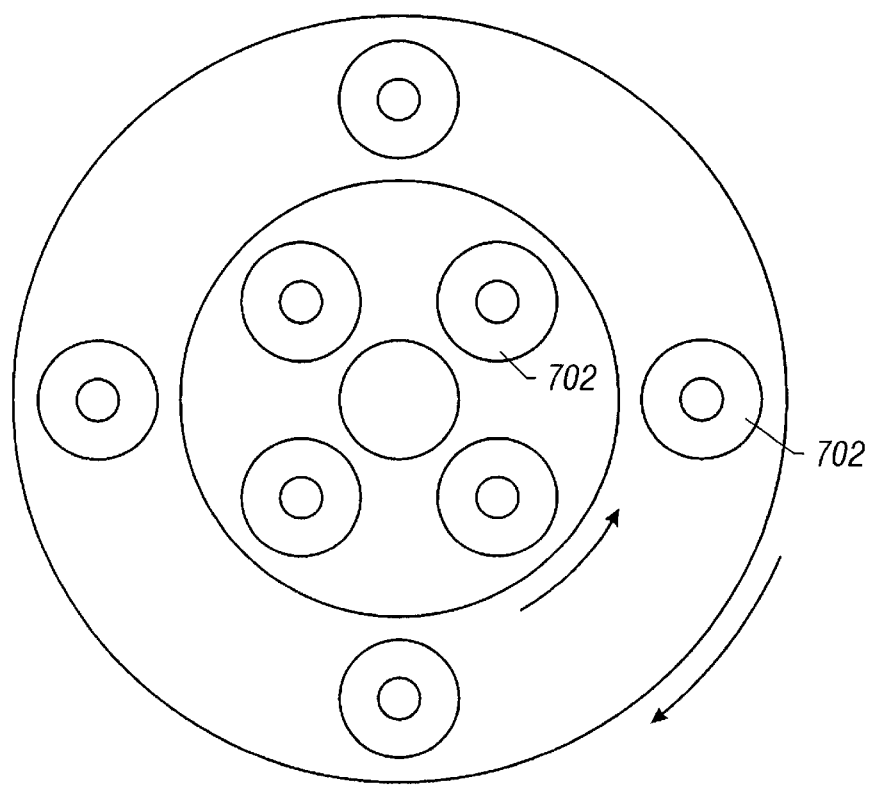
FIG. 34 is a top view of upper and lower weaving plates provided with bobbins according to one embodiment of the present invention.
Figure 35:
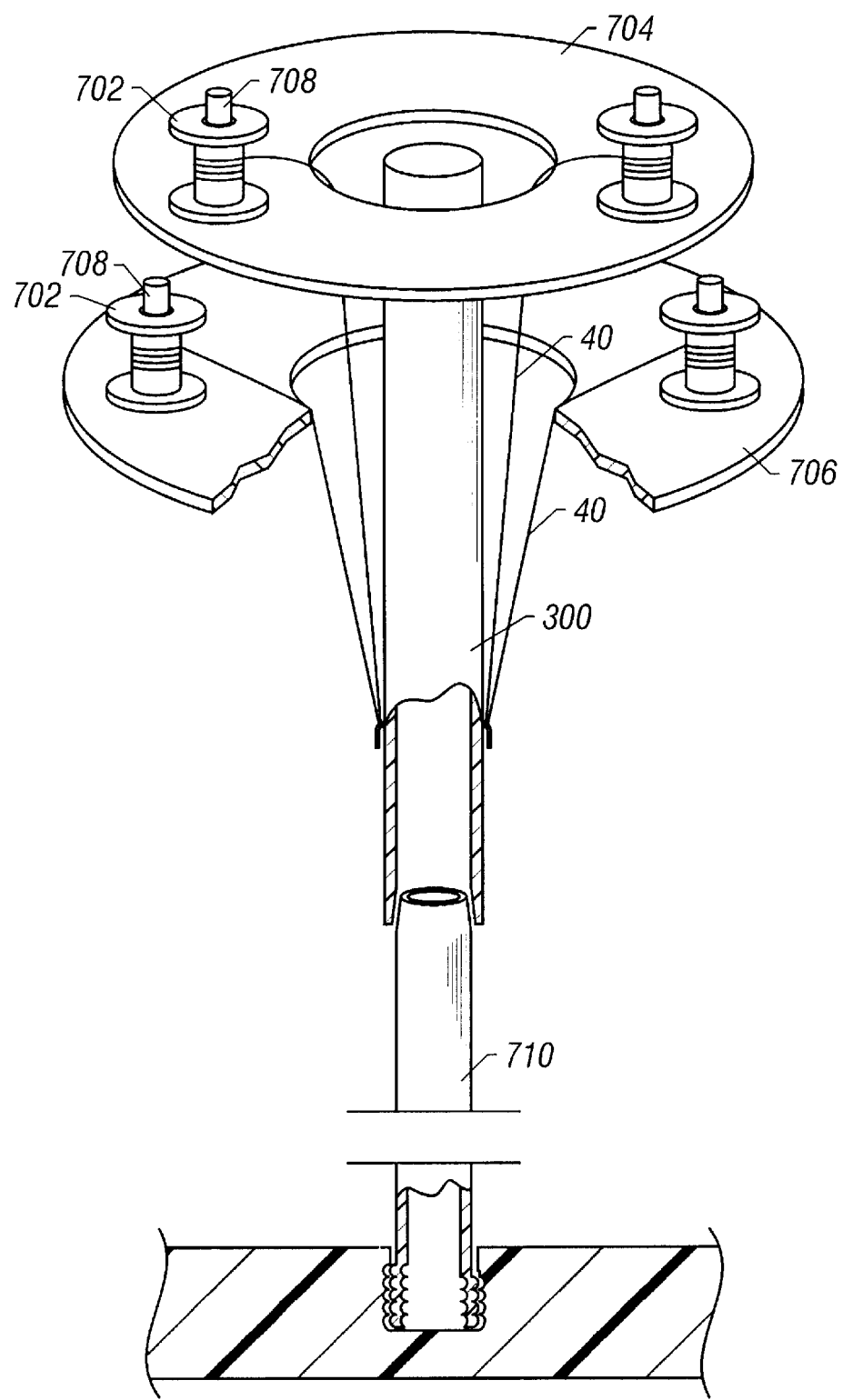
FIG. 35 is a cross-sectional front view of upper and lower weaving plates arranged on different planes around a template and provided with bobbins and wires according to one embodiment of the present invention.

As shown in FIG. 34, in one embodiment in which bobbins 702 are utilized, two coaxially arranged weaving plates may be utilized. As shown in FIG. 35, upper weaving plate 704 and lower weaving plate 706 may be positioned in different horizontal planes. FIG. 35 illustrates that the weaving plates may be equipped with multiple bobbin rods 708, the axes of which are substantially perpendicular to the weaving plates, on which bobbins 702 may be slidably secured. (FIG. 35 depicts only 4 bobbins for the sake of simplicity.) The weaving plates may be provided with holes therein through which template 300 and/or wires 40 may pass, as shown in FIG. 35. Template 300 may be secured to the base of the weaving machine chosen using any suitable means such as template rod 710, around which template 300 may be slidably placed (FIG. 35). Template rod 710 may be configured to firmly engage template 300 through frictional forces (e.g., by tapering template rod 710). Instead of template rod 710, any appropriate lock mechanism may be used to secure the base of the weaving machine to template 300.

Figure 36A:
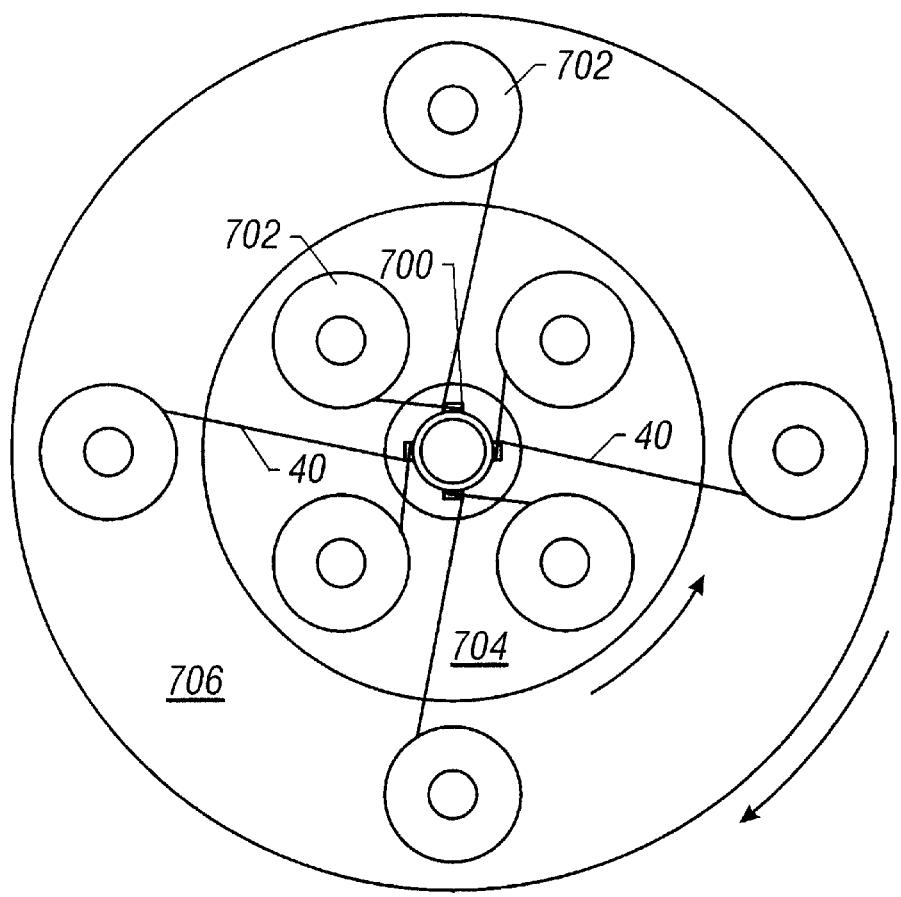
FIG. 36A is a top view of upper and lower weaving plates provided with bobbins and wires and arranged around a template, and illustrates the first crossing of the wires according to one embodiment of the present invention.
Figure 36B:
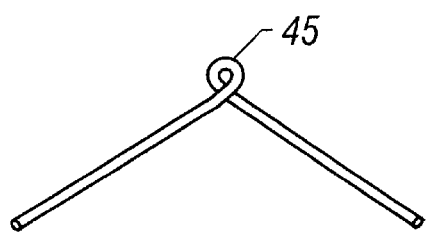
FIG. 36B is a front view of a small caliber loop formed by bending a wire according to one embodiment of the present invention.
Figure 37A:
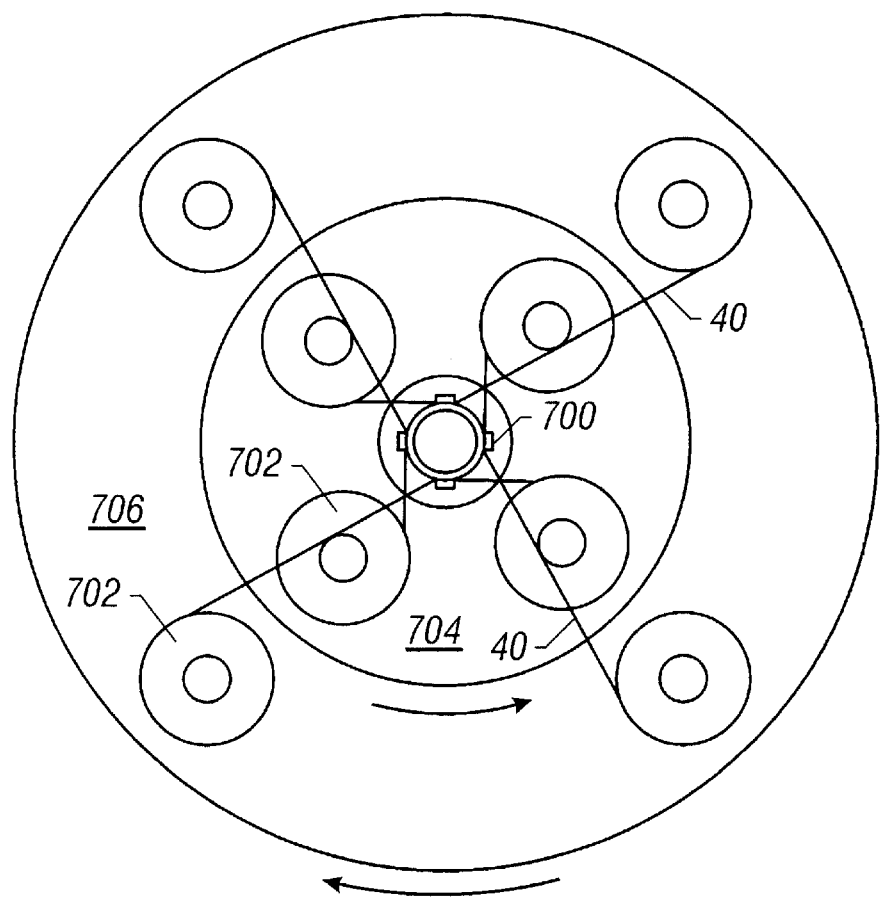
FIG. 37A is a top view of upper and lower weaving plates provided with bobbins and wires and arranged around a template, and illustrates the first crossing of the wires according to another embodiment of the present invention.

As shown in FIGS. 36A and 37A, the pairs of bobbins 702 may be prepared for weaving by arranging one bobbin on upper weaving plate 704 and the other bobbin from the pair on lower weaving plate 706. Wires 40 may then be bent around tabs 700, and the ends of the wires may be attached to bobbins 702 using any suitable means capable of holding wires 40 under tension throughout the weaving process. An example of such a mechanism is a one-way brake that allows bobbins 702 to rotate in a single direction only, such that wires 40 may wind off bobbin 702. Simultaneously, such a brake may be configured so as to continuously maintain tension in wires 40 by virtue of the brake's resistance to the winding off of wires 40.

Figure 37B:
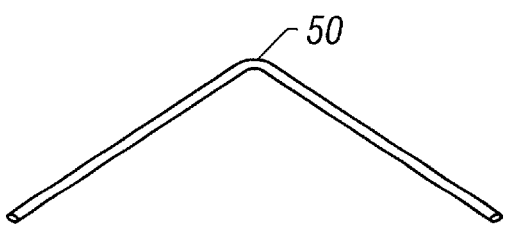
FIG. 37B is a front view of a bend formed by bending a wire according to one embodiment of the present invention.

As shown in FIG. 36A, with the ends of the wires in place, the weaving may begin by crossing the ends of the same wire, which results in the formation of a small caliber loop 45 (FIG. 36B) at the site of the bent portion. In another manner of weaving illustrated in FIG. 37A, the ends of different wires may be crossed first, resulting in bend 50 at the site of the bent portion (FIG. 37B).

Figure 38:
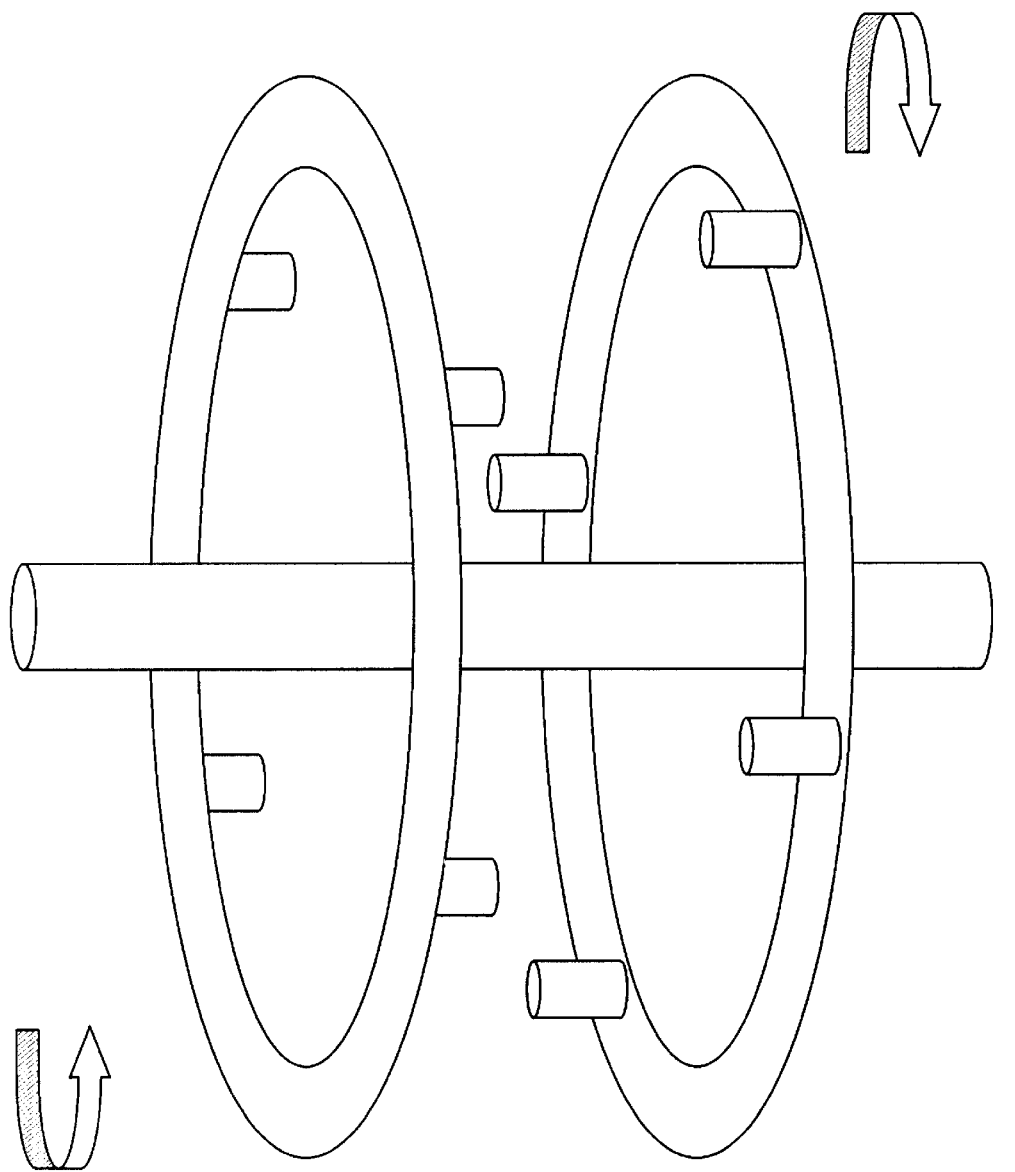
FIG. 38 is a perspective view of upper and lower weaving plates provided with bobbins and arranged around a template such that the surfaces of the weaving plates from which the bobbin rods extend face each other according to one embodiment of the present invention.
Figure 39:
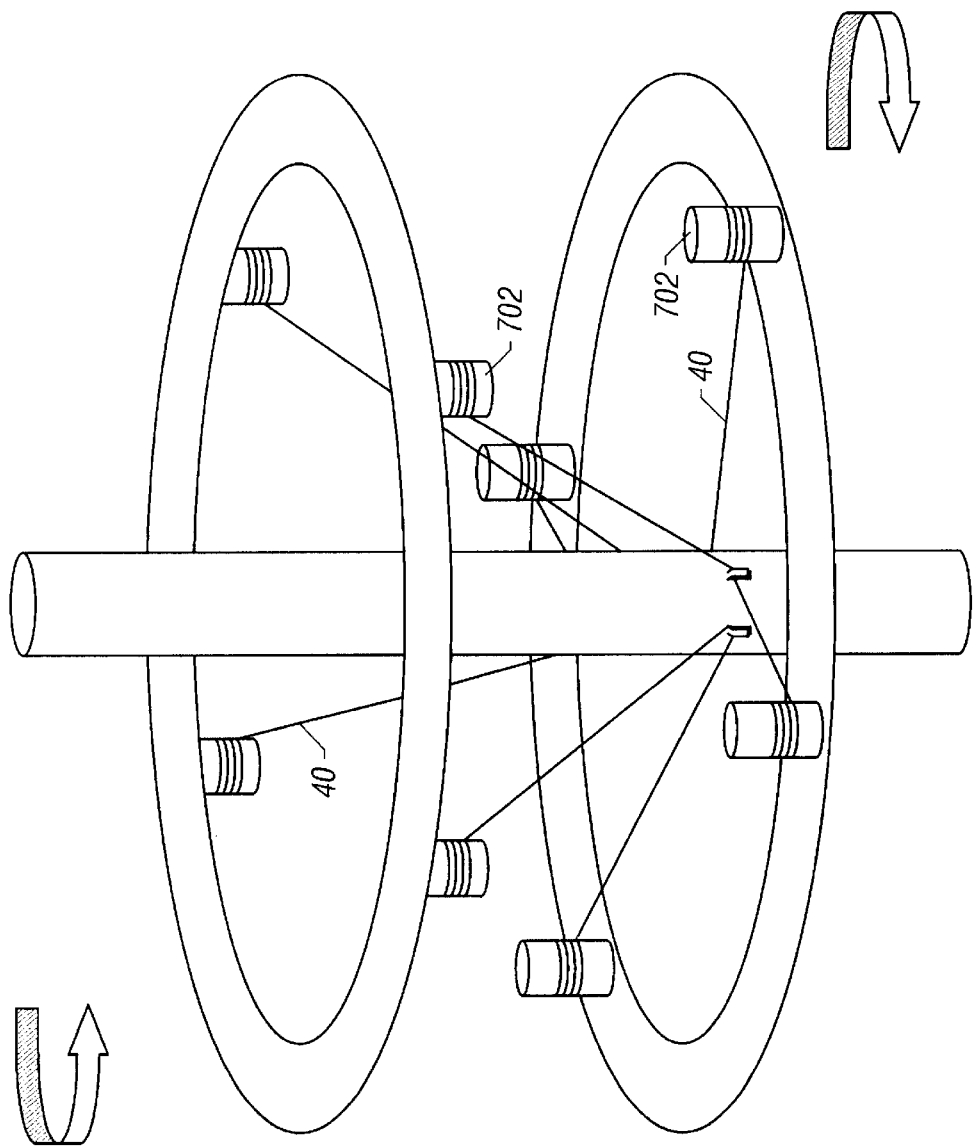
FIG. 39 is a perspective view of upper and lower weaving plates provided with bobbins and wires and arranged around a template such that the surfaces of the weaving plates from which the bobbin rods extend face each other according to one embodiment of the present invention.

As shown in FIGS. 38–39, the two weaving plates may be arranged such that the surfaces thereof from which bobbin rods extend face each other. In this alternative embodiment, the diameters of the plates may be the same or different. Wires 40 may be arranged on bobbins 702 in the same manner as described above, as shown in FIG. 39.

Despite which of the aforementioned weaving plate arrangements is utilized, the weaving plates rotate in opposite directions during the weaving process. The weaving plates may be operated at any suitable speed. In this regard, a speed as low as 1 to 10 cycles per minute is acceptable. The weaving plates may also be driven by hand.

Figure 45:
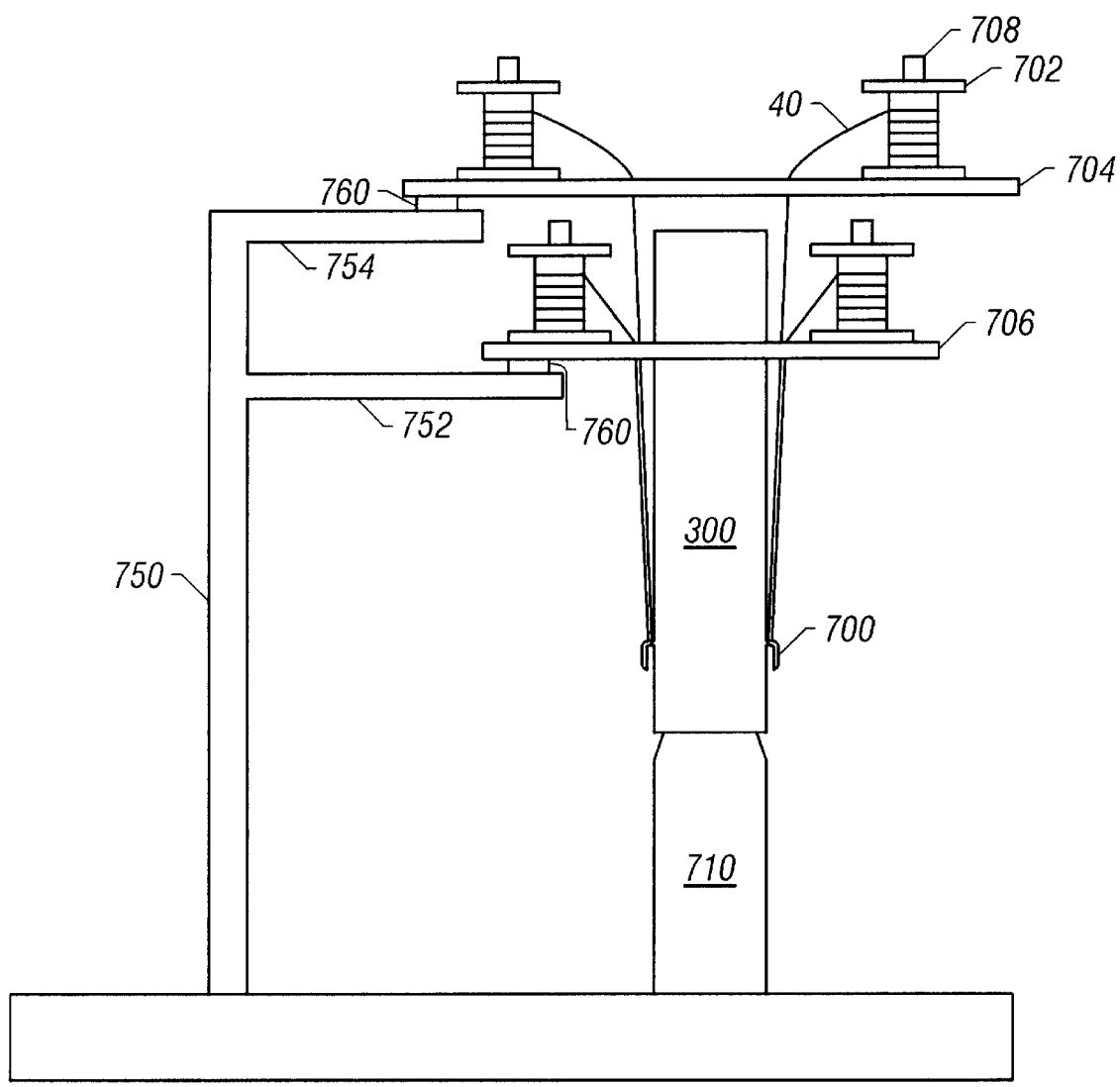
FIG. 45 is a front view of upper and lower weaving plates supported by a weaving plate supporter according to one embodiment of the present invention.

The weaving plates may supported and rotated using any suitable means. FIG. 45 illustrates one means of supporting and rotating weaving plates 704 and 706. (FIG. 45 depicts on 4 bobbins for the sake of simplicity.) As shown, weaving plate supporter 750 may be equipped with lower arm 752 and upper arm 754 for supporting lower and upper weaving plates 706 and 704, respectively. Weaving plate drivers 760 may be secured to the upper and lower arms of the weaving plate supporter and engaged with the weaving plates in order to operate them. The drivers may be configured to operate in any suitable fashion. For example, the drivers may be configured with a power source and provided with gears of any suitable configuration for causing the weaving plates to rotate. The drivers may also be configured to utilize magnetism or electromagnetism to rotate the weaving plates. The drivers may be also be configured such that the weaving plates may be rotated by hand. Further, although not shown, it will be understood to those of skill in the art, with the benefit of this disclosure, that either or both of the upper and lower arms may be provided with branches to which drivers may be attached. The drivers on the branches could then be secured to or engaged with the top surfaces of the weaving plates in the same fashion that drivers 760 are engaged with the bottom surfaces of the weaving plates as shown in FIG. 45. Thus, in such an embodiment, both the top and bottom surfaces of each weaving plate would be engaged with drivers.

Once the legs have been weaved, one of the weaving machines used to weave one of the legs may be utilized to continue weaving the common body of the stent. To do so, first, the bobbins and the corresponding wires may be rearranged around half of the weaving plates of one of the "leg" machines. The template with the other woven leg may be positioned and secured beside the first leg's template. The template configured for the common body of the stent, if one is used, may then be placed over both leg templates, or one template leg may be inserted into an opening of the common body template if such a configuration is utilized. The bobbins and corresponding wires of the second leg may then be arranged around the other half of the weaving plates, which is free of the first leg's bobbins and wires. The weave may then be continued on the common body template by rotating the weaving plates in opposite directions.

Figure 46:
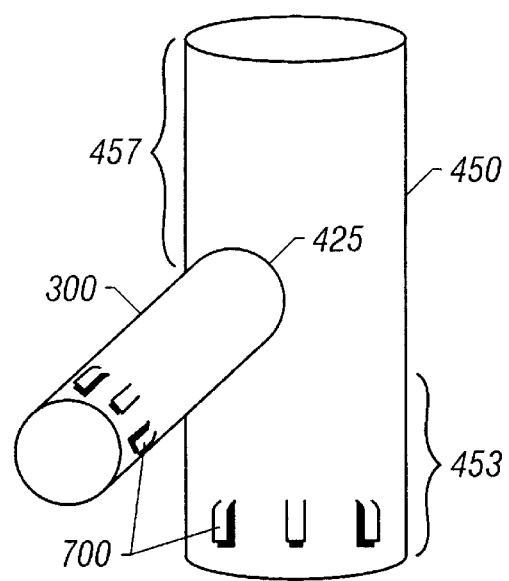
FIG. 46 is a perspective view showing a combination of two templates on which a bifurcated stent may be woven according to one embodiment of the present invention.

A bifurcated stent may also be created using only two templates consistent with the present disclosure. As shown in FIG. 46, template 300 is shown having template projections in the form of tabs 700 arranged around the template proximate the proximal end thereof. The distal end of template 300 is shown as being hidden from view because it is inserted into opening 425 of template 450. Template projections in the form of tabs 700 are also arranged around template 450 proximate the proximal end thereof. When templates 300 and 450 are utilized together, a leg may be woven around template 300 in any manner described above. Further, wires for the other leg may be bent around the tabs arranged around the proximal end of template 450, and the ends of those wires may be woven around portion 453, the portion of template 450 located proximally of opening 425. The wires from the two legs may be combined and woven around portion 457 to create the common body and the stent. As shown in FIG. 46, portion 457 is the portion of template 450 located distally of opening 425.

A braiding machine suitable for carrying the weaving process just described (i.e., utilizing the weaving plates) may be obtained, for example, from Wardwell Braiding Machine Company in Central Falls, R.I.

After the weaving process is complete, the ends of the wires may be twisted together or coupled as described above to form closed structures. To make the process of wire twisting faster and easier, the wires may be twisted with a special hand tool designed for this purpose. Tool 712 illustrated in FIG. 41A follows the principle of an automatic pencil. Jaws 714 of tool 712 are configured so that the ends of the wires may be firmly held between jaws 714. Jaws 714 may be activated by push button 716 moving against spring 718. After placing the wire ends into pre-formed gaps 720 located between jaws 714 (FIG. 41B), spring 718 expands (or returns to its unconstrained state) and retracts jaws 714, securing the wire ends firmly between jaws 714 due to the pressure of outer housing 722 acting to close jaws 714. Outer housing 722 may then be rotated to create multiple twists of the wire ends. As illustrated in FIGS. 42A and 42B, the twisted ends of common body 20 may be secured to template 400 using transverse tabs 724, which may be formed the same way as longitudinal tabs 700.

Next, the bifurcated stent may be heated at about 500° C. for 5 to 15 min, preferably about 12 to 15 min and then allowed to cool to room temperature. In one embodiment, the bifurcated stent may be heated to 500° C. for 15 minutes. As a result, the wires of the stent may exhibit superelastic properties. The initial shape of a stent programmed with superelasticity may be deformed by applying a force thereto. The shape memory of the stent may then be activated by removing the force, and the stent may substantially recover its initial shape. As used herein, "substantially recover" means that recovery need not be such that the exact original shape be regained. Rather, it is meant that some degree of plastic deformation may occur. In other words, recovery need not be total. In another embodiment, the stent may be programmed with thermal shape memory by heating it to about 500° C. for about 60 to 120 minutes, typically about 120 minutes, in an oven. In one embodiment, the bifurcated stent may be heated to 500° C. for 120 minutes. The initial shape of a stent programmed with thermal shape memory may be deformed upon application of a force at a first temperature. The force may be removed, and the stent may remain deformed. The shape memory of the stent may then be activated by heating the stent to a second temperature, at which temperature the stent may substantially recover its initial shape.

To make the final shape of the stent including the creation of slightly tapered legs and the adjustment of the angle between the common body and the legs, the stent may be remodeled on another template and reheated. The attachment to the remodeling template may be achieved in a fashion similar to the manner in which the wires are originally attached to the template, e.g., wrapped copper wires. Reheating may be done using a similar time and temperature as the initial heating. The stent crown 28 may also be flared for better fixation of the stent 10, with remodeling and reheating. After cooling down to room temperature, the stent wires may exhibit superelastic properties. It is to be understood that if the stent is remodeled a number of times and it is not intended that the stent be programmed with thermal shape memory, care should be taken not to exceed a total heating time (which includes the first heating time and the second heating time, etc.) of about 60 minutes, because at about 60 minutes, the stent may be programmed with thermal shape memory.

In an exemplary embodiment of stent 10, after heating and cooling, it is preferable to further reinforce the coupled wire ends 42 of closed structures 55 (particularly if they were coupled using twists) by any suitable means such as point welding, soldering, pressure welding, or the like, in order to better ensure that the coupled wire ends will not separate during delivery (to be discussed in detail below). Coupled wire ends 42 may be soldered by removing any oxide layer that may have formed over the relevant portions of the wires used, and applying solder to those portions. Soldering may be enhanced by first wrapping coupled wire ends 42 with thin stainless steel wires. In an exemplary embodiment, point welding is preferred to soldering, because point welding is easier to perform than soldering, and may be more suitable with regard to long-term implantation of the stent.

Biodegradable Version

The bifurcated stent of the present invention (and the trifurcated stent discussed below) may be formed with filaments made of biodegradable material so as to form a self-expanding, bioabsorbable, biodegradable stent that may, in addition to functioning as a stent, function as drug or nutrient delivery systems as a result of the material used.

Many factors may be considered in choosing materials from which to form the biodegradable bifurcated stent of the present invention. In one embodiment, the biodegradable stent of the present invention may be formed from materials of minimal thickness so as to minimize blood flow blockage and facilitate bioabsorbtion. In another embodiment, the material may be chosen so as to exhibit sufficient radial strength to allow the body formed to function as a stent. The material from which the biodegradable stent may be formed may also degrade within the bloodstream over a period of weeks or months, so as not to form emboli. However, the material may be chosen such that the stent does not degrade before an endothelial layer forms in the stented vessel or structure in cases in which vascular stenoses of arteriosclerotic origin are treated. The material chosen may be chosen to be compatible with surrounding tissue in the vessel as well as with blood.

The bifurcated biodegradable stent may be formed by plain weave using the methods above described. The size of the filaments used may vary according to the application. In some embodiments, the filaments may be reduced in size in comparison to the size of wires used in comparable applications involving non-biodegradable stents. In other embodiments, the number of filaments used may be increased in comparison to the number of wires used in comparable applications involving non-biodegradable stents. The minimum number of filaments that may be used to create the legs of the bifurcated stent may be about 5. In one embodiment, 12 filaments may be used. The minimum number of filaments that may be used to create the legs of the trifurcated stent (described below) may be about 5. In one embodiment, 8 filaments may be used. The minimum number of filaments that may be used to create the common body of the trifurcated stent (described below), prior to the legs being added thereto, may be about 10. In one embodiment, 8 filaments may be used. In creating the stent using plain weave, the angle of the crossed filaments (described above as angle a) may vary as described above, but is typically 150–160°. In one embodiment, the angle of the crossed filaments may be as large as possible to achieve the largest radial force possible and further ensure that the stent may have enough expansile force to remain in place after being delivered. The filament ends, after plain weaving is complete, may be coupled together to form closed structures using any suitable means such as by heat treatment or sealing, gluing, tying, twisting, crimping, taping, or the like.

In one embodiment, the filaments used may be made of polyglycolic acid ("PGA"), poly-L-lactic acid ("L-PLA"), polyorthoesters, polyanhydrides, polyiminocarbonates, or inorganic phosphates. These polymers are commercially available from United States Surgical Corporation, Norwalk, Conn.; Birmingham Polymers, Inc., Birmingham, Ala.; and Ethicon, Sommerville, N.J., for example. One factor to consider in choosing a material from which to make the filament will be the goal of the stent placement. For example, in an embodiment in which the stent serves mainly as a drug delivery system, PLA may be used because of its rapid degradation time. In another embodiment in which the stent serves mainly to maintain the patency of the vessel (i.e., keeping the vessel open) and as a scaffold or frame for the development of a new endothelial layer, PGA may be used considering its high strength and stiffness. In other embodiments, glycolide may be copolymerized with other monomers to reduce the stiffness of the resulting fibers that may be used.

In another embodiment, any of these filaments may be provided with about 0.05 to 0.25 percent by weight of a basic metal compound, such as calcium oxide, calcium hydroxide, calcium carbonate, calcium phosphate, magnesium oxide, magnesium hydroxide, magnesium carbonate, magnesium phosphate, sodium phosphate, potassium sulfate or the like, to increase the in vivo strength retention of the biodegradable stent by about ten to twenty percent or more, as described in U.S. Pat. No. 5,478,355 to Muth et al. (1995), which is hereby expressly incorporated by reference. As used herein, "in vivo strength retention" refers to the ability of a biodegradable body to retain its strength (i.e., the breaking load of the body) after being implanted or delivered into a living creature. In yet another embodiment, a filament obtained from a polymer containing about 15 to about 30 mole percent glycolide in a melt spinning operation, as described in U.S. Pat. No. 5,425,984 to Kennedy et al. (1995), which is hereby expressly incorporated by reference, may be used to form a biodegradable body.

The filaments of the biodegradable stent may incorporate one or more drugs that positively affect healing at the location where the stent is delivered. In one embodiment, these drugs may include anticancer drugs such as paclitaxel (which is commercially available as TAXOL, from Bristol-Myers Squibb in Princeton, N.J.) or docetaxel (which is commercially available as TAXOTERE, from Rhone-Poulenc Rorer in Collegeville, Pa.), fibroblast/smooth muscle cell proliferation-preventing agents, and antithrombogenic drugs such as heparin which is commercially available from Wyeth-Ayers in Philadelphia, Pa.

One or more drugs may be incorporated into a polymer using any suitable means. For example, in one embodiment, the drugs as a solute may be dissolved in the biodegradable polymer as a solvent to form a solution. The solution may then be hardened into a fiber from which the stent may be woven. In another embodiment, simple mixing or solubilizing with polymer solutions may be utilized. The drugs may also be dispersed into the biodegradable polymer during an extrusion or melt spinning process. In yet another embodiment, the biodegradable fibers that have already been formed may be coated with drugs.

The biodegradable filaments may be rendered radiopaque to facilitate their monitoring under fluoroscopy and/or their follow-up using radiographs, fluoroscopy, or computerized tomography. The methods described above for incorporating the drugs into the polymer may be used to mix radiopaque salts, such as tantalum, with the polymer.

As used herein, "degradation time" refers to the time during which the biodegradable stent maintains its mechanical integrity. One factor that should be considered in choosing a polymer in light of its degradation time is that the polymer will loose its mechanical integrity before it is completely absorbed into the body. For example, pure polyglycolide (PGA) sutures lose about 50% of their strength after 2 weeks, and 100% at 4 weeks, and are completely absorbed in 4–6 months. For vascular applications (i.e., applications in which the stent is placed within a vessel in a body), polymers having degradation times of about one to twenty-four months may be used, depending on the application. In a typical embodiment, a polymer having a degradation time of about one to three months may be used. In choosing a polymer for non-vascular applications such as the esophagus, colon, biliary tree, ureter, etc., one should consider the polymer's ability to withstand the chemical stimuli in the given environment.

During the degradation time of the biodegradable stent, a new endothelial layer may form on the surface of the stent. The rate of the release of the drugs which may be incorporated into the polymers may be controlled by the rate of degradation of the biodegradable material used. Thus, the rate of release of a drug may act as a control quantity for the rate of degradation. At the same time, other agents such as fibronectin from human plasma (commercially available from Sigma, St. Louis, Mo.) may be added to the polymer used (using any suitable means described above for incorporating drugs into the chosen polymer) and may affect the rate of biodegradation. For example, fibronectin may accelerate the growth of cells around the surrounding stent, which, in turn may accelerate the resorption reactions around the stent.

Figure 28:
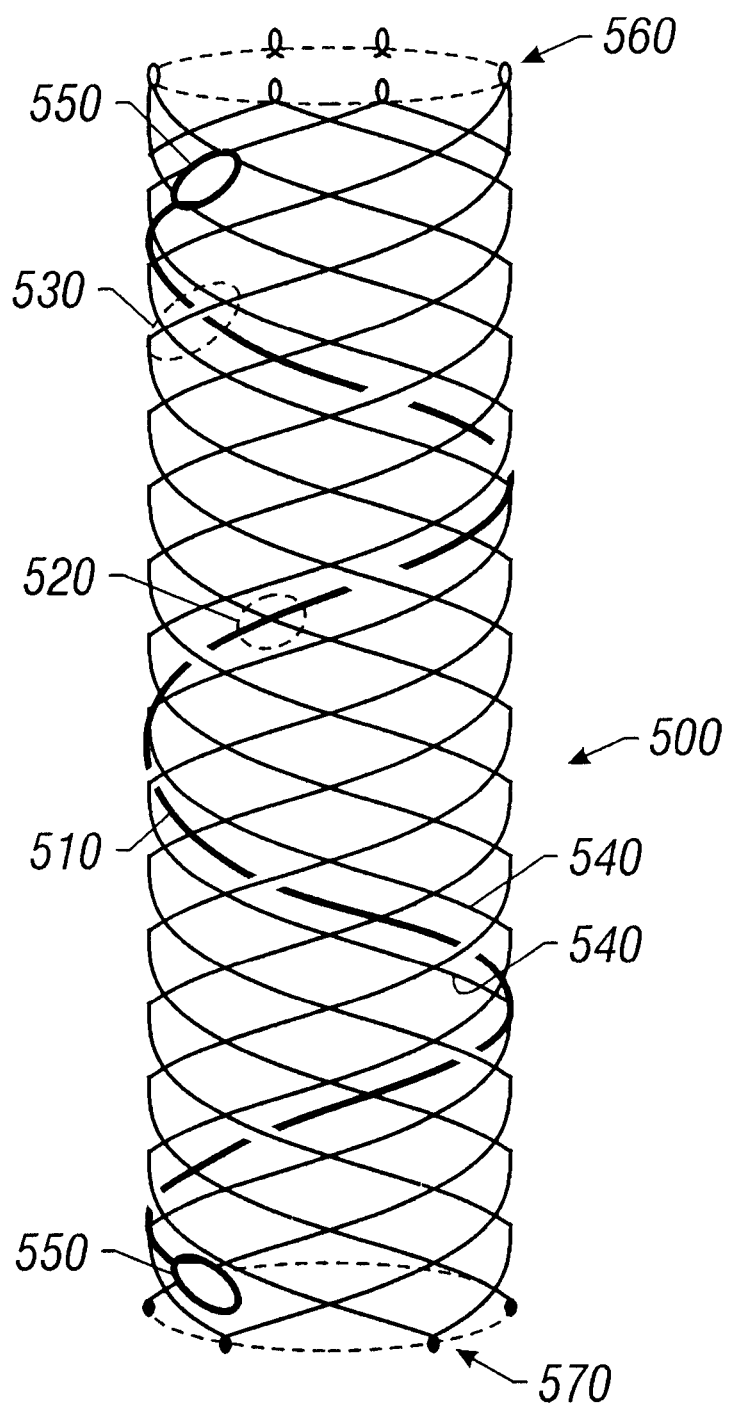
FIG. 28 is a perspective view of a biodegradable leg with a reinforcing wire according to one embodiment of the present invention.

In one embodiment of a biodegradable stent according to the present invention, one or more shape memory wires may be added to the either the legs or the common body of the bifurcated or trifurcated stents for reinforcement after forming the leg or common body using plain weave. Such wires may comprise nitinol or any other comparable material above described. In one embodiment, the wires may be formed from nitinol having about 55 to 56% Nickel and 45 to 44% Titanium (Shape Memory Applications). The wire or wires may be incorporated into the woven biodegradable structure by threading the wire in and out of openings in the leg several times. In one embodiment, the manner in which the wire is threaded in and out of openings in a leg is shown in FIG. 28. In FIG. 28, designation 520 shows reinforcement wire 510 passing outside biodegradable leg 500, and designation 530 shows reinforcement wire 510 passing inside biodegradable leg 500, thus showing how wire 510 may be threaded in and out of openings in leg 500. As shown in FIG. 28, the reinforcement wire(s) 510 may be led between (i.e., parallel to) two biodegradable filaments 540 and may follow their helical course. As shown in FIG. 28, reinforcement wire 510 may be secured to leg 500 with loops 550, or any other suitable means such as tying, twisting, or the like. Loops 550 may be placed around a filament or around the intersection of one or more filaments. As a result, the wire can move in harmony with the weave and will not interfere with the movement of the filaments in the weave. By activating the shape memory of reinforcement wire 510, ends 560 and 570 of leg 500 may be pulled together, resulting in a tighter weave. As a result, the expansile force of the stent and its resistance to outer compression may significantly increase. In one embodiment, loops 550 may also be used in securing leg 500 to a delivery system.

Figure 29:
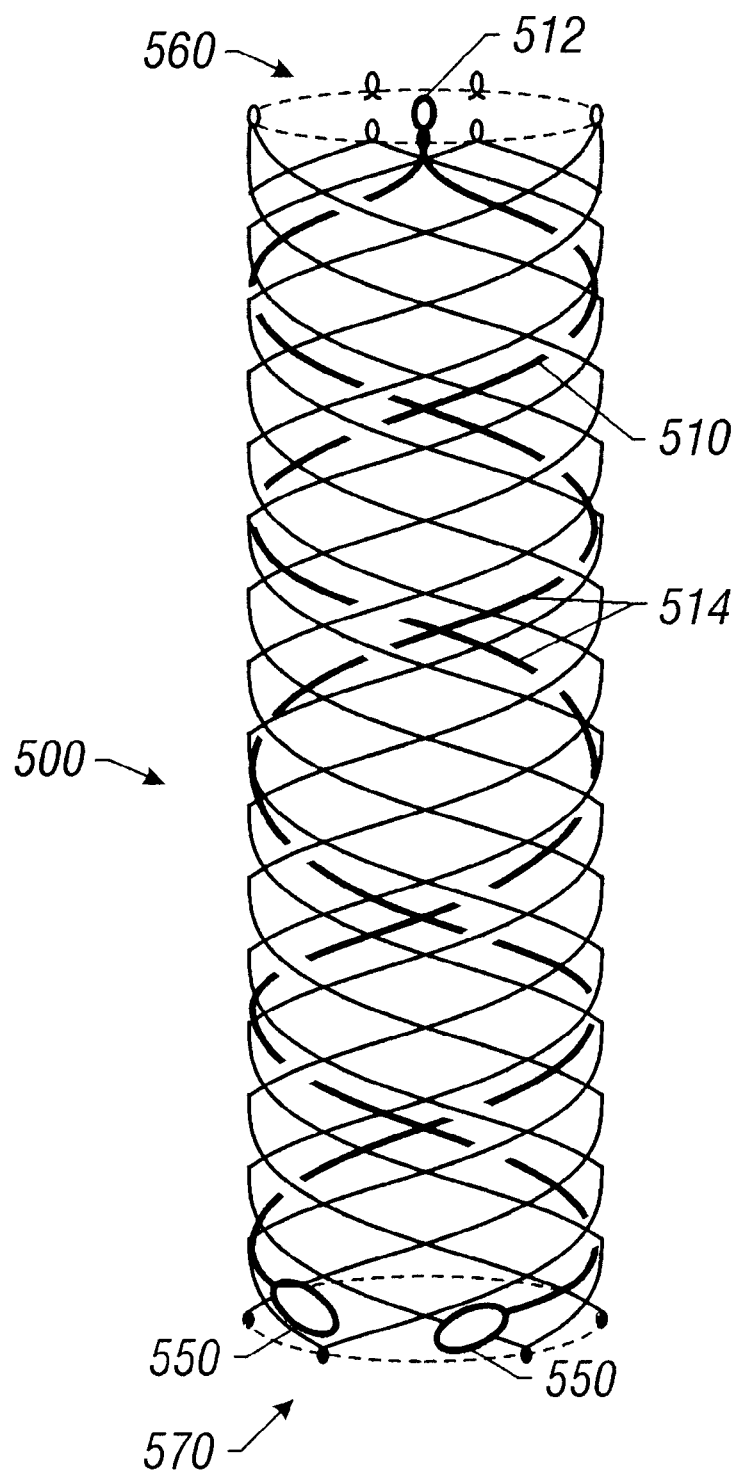
FIG. 29 is a perspective view of a biodegradable leg with a reinforcing wire according to a second embodiment of the present invention.

In another embodiment shown in FIG. 29, in which a reinforcement wire is threaded in and out of openings in a biodegradable leg according to the present invention, reinforcement wire 510 may be bent at a selected point located between its ends, typically at about the mid-point of the wire, and a small loop 512 may be created (similar to the small closed loops described above). As shown in FIG. 29, small loop 512 may be entwined around a filament or the intersection of one or more filaments, and reinforcement wire 510 may be threaded in and out of the openings in leg 500 as described above, and may be secured to leg 500 with loops 550, or any other suitable mean, as above described. Both portions 514 of reinforcement wire 510 may be symmetrically led along both sides of leg 500 following the sinuous/helical course of the biodegradable filaments. As described earlier, by activating the shape memory of reinforcement wire 510, ends 560 and 570 of leg 500 may be pulled together, resulting in a tighter weave. As a result, the expansile force of the stent and its resistance to outer compression may significantly increase. In one embodiment, loops 550 may also be used in securing leg 500 to a delivery system.

In one embodiment, the size of reinforcement wire 510 may range from about 0.005 inches to about 0.012 inches. It is to be understood that increasing the size of reinforcement wire 510 may increase the force with which ends 560 and 570 are pulled together when the shape memory of the wire is activated. It is to be understood that using more than one wire may have the same effect as increasing the size of the wire.

In one embodiment, reinforcement wire(s) 510 may be formed around a template as above described. The reinforcement wire(s) may then be programmed with superelasticity or thermal shape memory as described herein.

Bench-work

With regard to the biodegradable version of the stents according to the present invention, the inventors have used an open-ended plain woven nylon leg (that is, the filament ends were not coupled toge ther to form closed structures after weaving) for initial bench work. The leg was woven using 0.007 inch nylon filaments. The number of filaments used was 16, and the unconstrained diameter of the leg was 11 mm. In an unconstrained state, the size of the weave holes was approximately 1 mm. The expansile force of the leg was relatively good, and after maximum elongation the leg readily reverted to its unconstrained diameter. Compressing the leg from its two ends longitudinally, the expansile force could be increased considerably. At the maximal longitudinal compression, the diameter of the leg was 13 mm. Holding both ends of the leg, it became virtually incompressible.

A 0.006" nitinol wire was threaded through the holes of the unconstrained mesh in the manner described earlier. The wire was a straight nitinol wire and was not formed on a template and programmed with either thermal shape memory or superelasticity. The straight wire caused the leg to elongate and the unconstrained diameter of the leg decreased to 9.5 mm (13% lumen-loss though the other characteristics of the leg did not change. The woven tubular leg could be elongated completely as well as compressed maximally.

Possible Applications of the Stent

The present invention makes it possible to use stent 10 in several vascular and non-vascular territories where bifurcated anatomical structures are present. The range of possible vascular applications includes the aorto-iliac bifurcation, the superior vena cava (SVC) junction, and the inferior vena cava (IVC) junction . After recanalizing an extended aorto-bi-iliac obstruction (ertiche syndrome), the stent would be ideal to maintain the lumen of the aorto-iliac bifurcation. For treatment of an abdominal aortic aneurysm, the stent may be covered using some kind of elastic covering material, turning it into a stent-graft. The stent would also be an ideal solution for treatment of tracheo-bronchial obstructions. The bifurcated stent may also be used in hilar biliary stenoses (e.g., Klatskin tumors). For stenting malignant stenoses, the stent may be equipped with a special cover (e.g., of polyurethane or silicon) and/or with an anticancer coating. Another possible application may be stenting the venous side of a hemodialysis access graft after dilating the venous stenosis to maintain the lumens of both the graft and the parent vein.

The stent according to the present invention makes it possible to change the angles between the crossing wires (e.g., creating a tighter weave and/or a tapering shape), resulting in a controlled expansile force. Selecting the angles between the crossing wires so that they are close to the practical maximum of 180°, the expansile force of the stent may be increased to the point that a virtually incompressible stent may be created. As discussed in the Examples herein, the in vitro studies suggest that the same size nitinol stent with a similar mesh tightness as the WALLSTENT (Schneider, Minneapolis, Minn.; Boston Scientific Vascular) may exert much more resistance to outer compression (see Tables 2 and 3 below). This feature may be utilized in some vessel stenoses/obstructions caused by space occupying malignancies (e.g., SVC syndrome), where high outer compressive forces are present.

The angle between the main body 20 and the legs 30 may be adjusted to accommodate the patient's anatomy. Because of the flexibility of the stent, the angle between the legs 30, which may be selected according to the average sizes of the given anatomical structure, may be used in the majority of the cases. The angle for a tracheobronchial application may be about 45 to 70°. In humans, the trachea bifurcation typically has an angle of about 65°. Similarly, the cross-section of the main body 20 may also be changed from a round to somewhat elliptical shape, if necessary (e.g., tracheo-bronchial application). For better fixation of the stent, the crown 28 of the common body 20 may be flared. The length of the stent's common body 20, as well as the legs 30 may also be varied according to the particular requirements of the anatomy.

The stent may then be stretched to reduce its diameter as much as possible. Then, using a delivery system according to the present invention, which may hold the stent in a stretched state, the stent may be inserted into the bifurcated tubular structure to be stented.

Delivery Systems and Stent Deployment

The present invention also includes delivery systems for the stent, which may vary according to the applications of the stent. Two basic versions of the delivery systems are the tracheo-bronchial type and the aorto-iliac type.

A. Tracheo-Bronchial Application
a. First Embodiment

Figure 3:
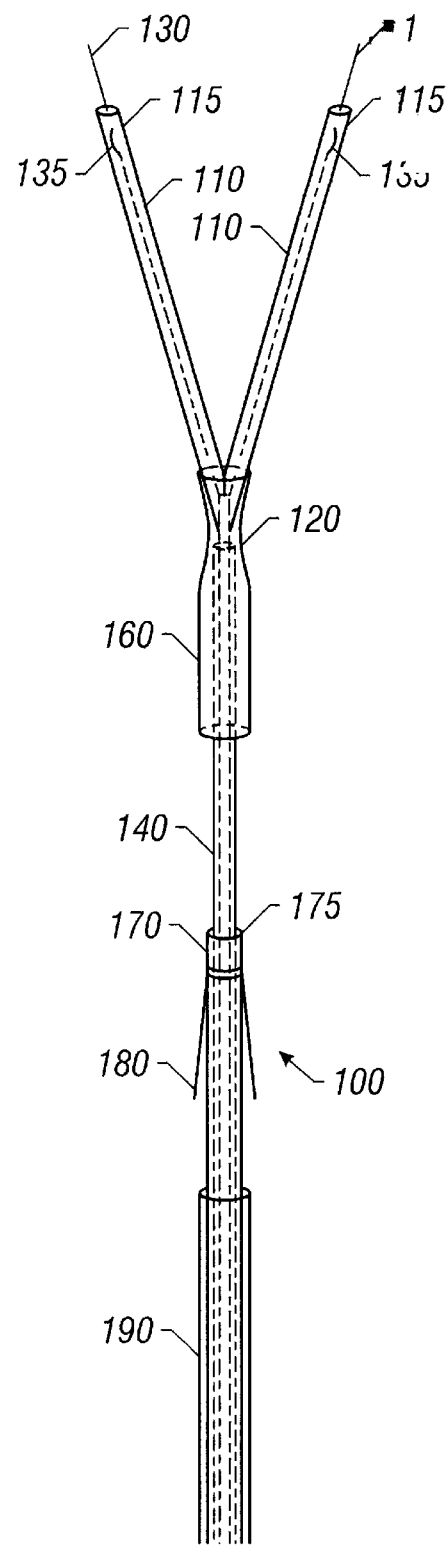
FIG. 3 is a perspective view of a delivery system for a bifurcated stent according to one embodiment of the present invention.

FIG. 3 is a diagram of an exemplary embodiment of the front part of a delivery system 100 according to the present invention, which comprises two small caliber tubes or legs 110 (which may be constructed of Teflon, PVC, Nylon, or any other suitable material) which fit within either a funnel-shaped sheath (or a Y-shaped) piece 120 (which may be constructed of a similar material to 110). A single lumen tube 140 also fits within this funnel or the common trunk of the Y-shape piece 120. Tube 140 may be made of a thin-walled, flexible, metal microtubing. In one embodiment, tube 140 may be made of nitinol (commercially available from Shape Memory Applications). The distal end 115 of each small caliber tube may be equipped with two holes positioned close to the tip. Two securing wires 130, which in an exemplary embodiment may be nitinol wires between about 0.009"–0.013")as used herein, 0.009" means 0.009 inches, and the like) thick, one in each leg 110, may be used to hold the distal end of the stent legs 30. Other materials from which securing wires 130 may be formed include any superelastic or pseudoelastic materials. In one embodiment, securing wires 130 (and all other wires described in A. and B. herein) may be nitinol wires which comprise about 55–56% Nickel and about 45–44% Titanium (commercially available from Shape Memory Applications). In an embodiment in which the securing wires of the present invention are nitinol (including wires 130 and the others discussed below), the nitinol securing wires may be heat treated as described herein or purchased from a manufacturer such that the superelastic properties of the nitinol may be utilized. These nitinol securing wires 130 come out from the lumen 140 through the proximal hole and go back through the distal hole, forming a small profile tight loop 135 between the two holes, as shown in FIG. 3. The nitinol securing wires 130 are threaded into the single lumen tube 140 after passing the funnel or the Y-shape piece 120. The distal 1.5–2.0-cm-long ends of the nitinol securing wires 130 may be equipped with a small piece of soft tip to facilitate maneuvers within the tracheo-bronchial system. The bifurcated stent 10 is placed over this Y-shaped tubing assembly with the distal legs attached to the tight nitinol wire loops between the holes. That is, wire 130 may be threaded through the proximal hole, through a closed structure (such as a bend or small closed loop or another opening in the weave), and back into the lumen of tube 110 through the distal hole.

It is to be understood that in an exemplary embodiment of delivery system 100 according to the present invention, multiple securing wires may be utilized instead of one in each leg 110 of the delivery system. In this embodiment, the distal ends of legs 110 should be equipped with a series of pairs of holes arranged substantially evenly around the circumference of the legs.

It is to be understood that in an exemplary embodiment of delivery system 100, two steerable guidewires with good torque control, preferably made of nitinol (commercially available from Microvena Co. in White Bear Lake, Minn.), may be utilized instead of flexible pieces of soft tip. The guidewires may be equipped with a soft radiopaque tip (made from platinum, tungsten, or any other suitable material) and may be placed in the lumens of the tubes 110 and in the single lumen tube 140. In a further embodiment, these tubes may be equipped with two channels; one channel may be created for the securing wires and the other for the guide wires. As a result, the movement of the guidewires during manipulations will not interfere with the firm position of the securing wires and vice versa.

To create some free covered space around tube 140 immediately behind the conflation of tubes 110, a short segment 160 of a larger caliber thin-walled sheath may cover tube 140 as well as the proximal ends of the small caliber tubes 110. If the connection between the small caliber tubes and tube 140 is created by a funnel shaped piece 120, 120 and 160 may be fabricated from the same piece (as shown in FIG. 3). If a Y-shape piece is used, segment 160 may be attached to the common trunk of the Y-shape piece 120. In such an embodiment, 120 and 160 may be fabricated from the same piece. The created space may be used to hide inverse tabs attached to the proximal part of the delivery system 100.

Coaxially, a larger tube 170 (which may be Teflon or any other material described above and two French-sizes larger than tube 140) may be positioned over tube 140. Near its distal end 175, tube 170 may be equipped with some metal hooks 180 facing proximally (FIG. 3). These inverse metal hooks 180 may be used for securing the proximal end of the common body 20 of stent 10.

Figure 5:
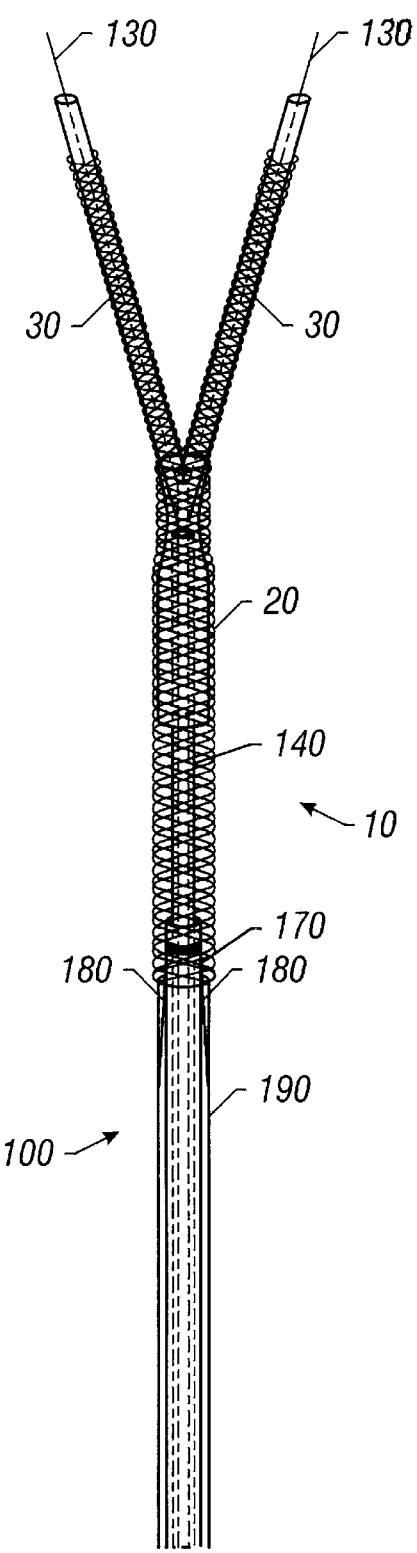
FIG. 5 is a perspective view of a stretched bifurcated stent on a delivery system according to one embodiment of the present invention.

After securing both the legs 30 and the common body 20 of stent 10 using the low profile nitinol loops and the inverse hooks 180 (which may be threaded through the closed structures or other openings near the stent's end), the stent may be maximally stretched over the tubes, as shown in FIG. 5. An outer thin-walled sheath 190 may be pulled over the proximal end of the stent. As a result, the proximal end of the stent 10 may be fixed to the delivery system 100, and simultaneously the hooks will be covered. Separate lock mechanisms attached to the proximal ends of the parts of the delivery system 100 will ensure that the stent 10 remains in the extended state during delivery. Separate lock mechanisms may also be used to secure the nitinol wires 130 and prevent the premature release of the stent 10.

Figure 2:
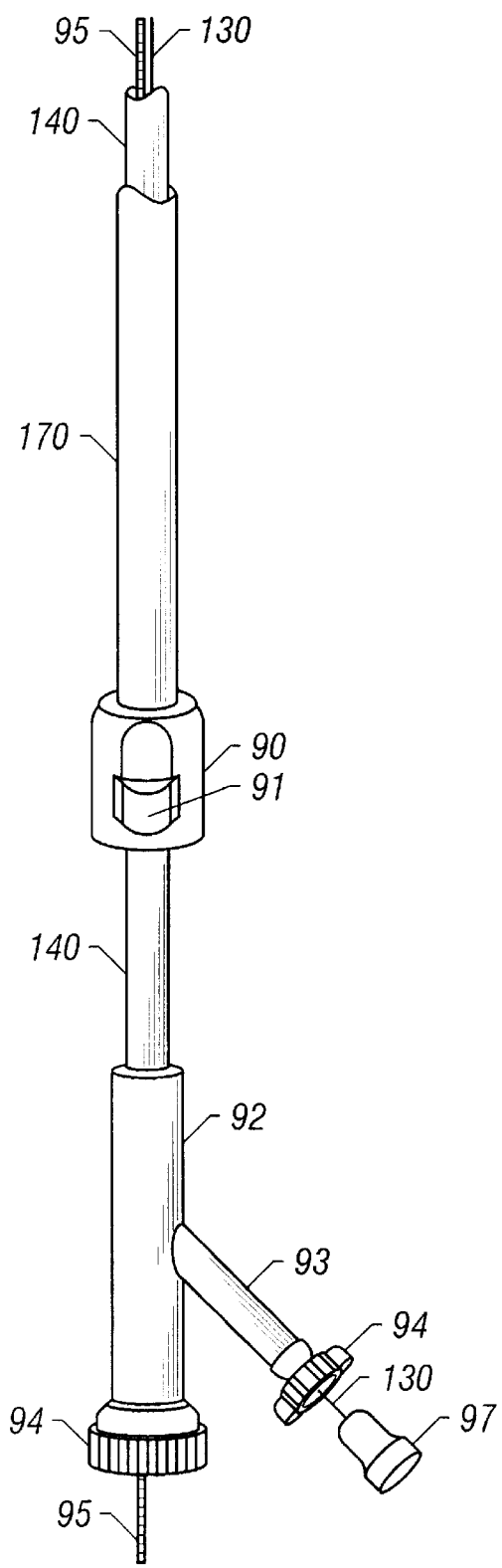
FIG. 2 is a front view of a proximal portion of a delivery system according to one embodiment of the present invention.

As shown in FIG. 2, a push-button lock/release switch mechanism 90 (such as a FloSwitch®HP device from Meditech/Boston Scientific Corp., Watertown, Mass. or a CRICKETT device from Microvena in White Bear Lake, Minn.) may be used to secure tube 140 to tube 170 when necessary. When switch 91 of push-button lock/release switch mechanism 90 is in an open or unlocked position, the two tubings are unlocked and as a result tube 170 moves freely on tube 140. This free movement allows for the stent to take on its unconstrained shape and size. When switch 91 of push-button lock/release switch mechanism 90 is in a closed or locked position, the two tubings are locked, the two tubes cannot move relative to each other, and the stent may be maintained in a completely stretched state. Tube 170 may be provided with a hub or flange for facilitating the attachment of push-button lock/release switch mechanism 90 thereto. As shown in FIG. 2, an end fitting 92 with a side-arm 93 may be attached to tube 140 using a Luer lock mechanism. The attachment between tube 140 and end fitting 92 may be facilitated by providing tube 140 with a hub or flange (not shown). End fitting 92 may be equipped with two tightening screw mechanisms 94, one for the two steerable guidewires 95 (only one of which is shown), and the other for the securing nitinol wires 130 (although one securing wire is illustrated, it is to be understood that more than one may be used in this exemplary embodiment). These tightening screws may be used to secure the guidewires and the nitinol securing wires in position during the stent delivery. The proximal ends of the securing nitinol wires 130 may be held together with a "handle" piece 97, facilitating their simultaneous movement during stent deployment. End fitting 92 may be equipped with separated lumens in a double channel system. The guidewire(s) may be placed in one lumen, and the securing wire(s) may be placed in another lumen.

With regard to the securing wires described herein, which may be used to secure the present stents to the delivery systems described herein, it will be understood to those of skill in the art, having the benefit of this disclosure, that the securing wires may be controlled by creating openings in whatever tube the securing wires are positioned within (the holes generally being made near the proximal end of the relevant tube) and threading the proximal ends of the securing wires through those holes. In this way, the relevant portion of the stent being delivered may be released by pulling the proximal ends of securing wires, which are positioned exterior of the relevant tube.

At the first stage of deployment, the delivery system 100 may be inserted through a tracheal tube. Both legs 110 of the delivery system 100 may be advanced in the main bronchi so that the junction of the legs 110 can be caught by the carina of the trachea. Holding the delivery system 100 in this position, the proximal portion of the common body 20 may be released. To do so, the outer thin-walled sheath 190 may be withdrawn to expose hooks 180. Tube 170 with hooks 180 may be moved distally to unhook the stent. Tube 170 with hooks 180 may then be moved further distally so that hooks 180 will be covered by segment 160 attached to the Y-piece. The wires 130 of each leg may be pulled back one after the other, and legs 30 of the stent will be released.

The stent may be released by starting the deployment with the release of the legs. The method of deployment which releases the common body of the stent first may be preferred to a first-legs-release, because the released common body can secure itself above the carina, and thereby significantly decrease the chance of deploying the stent higher than optimal within the trachea. No matter which order of release is used, after hiding the proximal hook mechanism in the thin-walled sheath piece 160, the delivery system can be easily withdrawn and removed.

b. Second Embodiment

Figure 4:
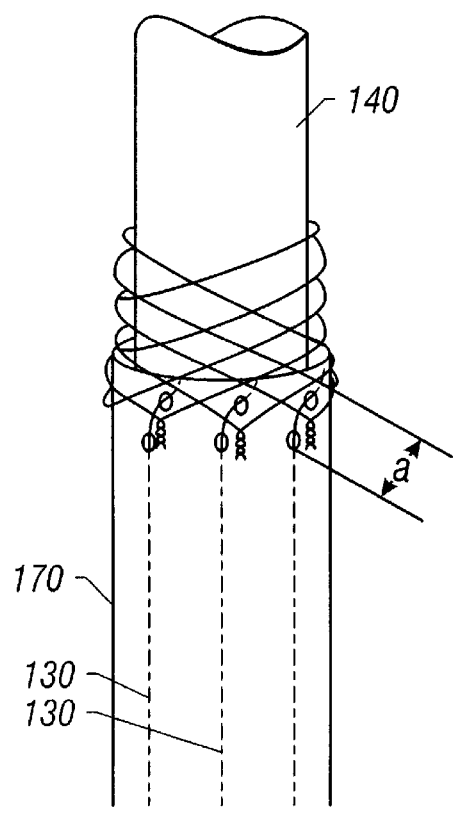
FIG. 4 is a perspective view of a portion of a delivery system according to one embodiment of the present invention.

In an alternate embodiment shown in FIG. 4, the proximal portion of the delivery system does not use the inverse hook mechanism. Instead, the proximal end of the stent may be secured to tube 170 with a tight nitinol loop as above described, similar to that used for securing the distal ends of the stent legs to tubes 110. To achieve an even arrangement of the stent's twisted wires around the tube, multiple tapered nitinol wires 130 (having tapered segment a) may be threaded through multiple pairs of holes arranged substantially evenly around the circumference of the tube, as shown in FIG. 4. In this and all exemplary embodiments utilizing securing wires, the ends of the securing wires may be tapered, making it possible to avoid a crowded arrangement of the coupled wire ends on tube 170.

In general, the strength of the small profile nitinol loops depends primarily on the size of the wire used. But the size and shape of the holes, as well as the relationship of the corresponding holes (that is, whether they are arranged parallel to the longitudinal axis of the tubing or run obliquely) may have an impact on the strength of the securing loops.

The tracheo-bronchial type versions of the delivery system described above may also be used for an SVC bifurcated stent placement from a femoral vein approach, or for an IVC bifurcated stent placement from a jugular approach.

B. Aorto-Iliac Application

Figures 6, 7:
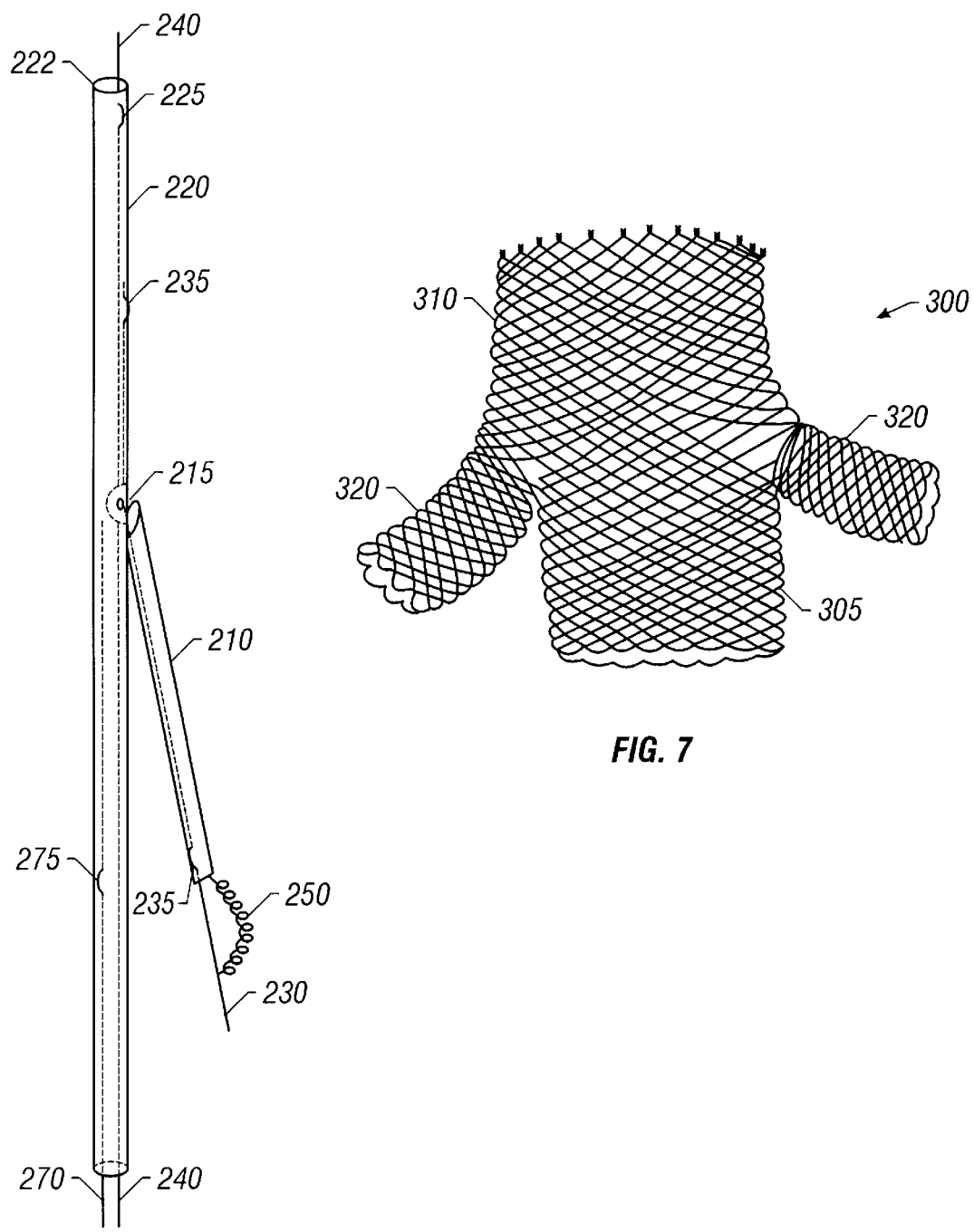
FIG. 6 is a perspective view of a delivery system according to one embodiment of the present invention.
FIG. 7 is a front view of a trifurcated stent according to one embodiment of the present invention.

As shown in FIG. 6, the delivery system 200 of this alternate embodiment may comprise two straight tubes 210 and 220 (which may be Teflon or any other material described above, and may be preferably D-shaped, although round shapes may be used) of different lengths. The shorter tube 210 is flexibly connected to the longer tube 220 (in some applications, the connection may be at about the mid-point of tube 220), thereby creating a joint. At the point of connection, a notch may be cut on the longer tube 220 facing toward the shorter tube 210. Notch 215 may facilitate movement of the shorter tube 210 at the joint, and with the two tubes in a side-to-side arrangement forming a slightly elliptical cross-section, the size of the delivery system may be minimized.

The flexible connection between the two tubes may use, in an exemplary embodiment, a wire 230, as shown in FIG. 5, such as a 0.011"–0.015" wire made of nitinol (commercially available from Shape Memory Applications) or any pseudoelastic or superelastic material. The wire 230 may be fed through two holes positioned on the shorter tube 210 close to its proximal tip. The wire 230 may form a low profile, tight loop 235 (like the loops described above) between the holes and may be used to secure the proximal end of the contralateral or left leg 30 of the Y-shape stent in the manner described above. The wire 230 may then be placed within the lumen of the shorter tubing. At the site of the attachment, the wire 230 may be contiguously led through a hole in the longer tube 220 to the lumen of the longer tube 220. The wire 230 may be led almost to the distal end of this tubing. Another low profile, tight loop 235 may be formed from the wire 230 at any suitable location along the longer tube 220, in order to strengthen the connection between the two tubes. In this regard, low profile loop 235 is shown about mid-way between notch 215 and distal end 222, but it will be understood that the loop may also be located close to distal end 222.

A small-profile, tight securing loop 225 (like those described above) may be created using wire 240 (which may be made of nitinol (Shape Memory Applications) or other suitable materials described above) close to the distal end 222 of the longer tube 220. This loop may be used to secure the common body 20 (stent crown) of the Y-shape stent 10 to tube 220 in the manner above described. Within the same lumen, another wire 270 (which may be made of nitinol (Shape Memory Applications or other suitable materials described above) may be placed, which may form another small-profile, tight loop 275 near the proximal end of the longer tube 220. This loop may be used for securing the ipsilateral or right leg of the stent.

To facilitate the positioning of the contralateral leg 30, a monofilament 250 which may be a 3.0–4.0 (metric 1.5–2.0) and made of, for example, 2-0, 3-0, or 4-0 Prolene (commercially available from Ethicon) or nylon, may be attached to the proximal end of the contralateral leg of the Y-shape stent. This monofilament may be connected firmly to the proximal portion of wire 230 that secures the contralateral leg of the stent.

In operation, both femoral arteries may be punctured and adequately-sized introducer sheaths inserted in each. From the left femoral approach, a first nitinol snare e.g., an Amplatz Gooseneck snare (commercially available from Microvena), may be inserted and manipulated into the right iliac artery. From the right femoral approach, a second nitinol snare similar to the first (e.g., Amplatz Gooseneck from Microvena) may be inserted by which the first nitinol snare may be pulled through the right femoral sheath. While the stent 10 remains still outside the body, monofilament 250 and wire 230, both of which are attached to the contralateral leg of the stent 10, may then be pulled through the left femoral sheath by the first nitinol snare.

The delivery system 200 may then be inserted through the right femoral sheath and positioned in the abdominal aorta so that the contralateral leg 30 of the stent 10 can be above the aorto-iliac bifurcation. Pulling back monofilament 250/wire 230 together with the whole delivery system, the contralateral leg 30 of the stent 10 may be positioned in the left iliac artery.

As the first step of deployment, wire 230, which secures the contralateral leg of the stent, may be pulled out so that the contralateral leg will be released first. Pulling on the monofilament 250, tube 210 may be removed through the left femoral artery sheath. The ipsilateral leg 30 of the stent 10 may be released by withdrawing the third wire 270. In the next step of delivery, the common body 20 of the stent may be released after pulling nitinol wire 240 out. In the final step, the longer tubing of the delivery system 200 may also be withdrawn and removed through the right femoral sheath. It is to be understood that the order of release of the legs and common body of stent 10 may differ from that just described.

In an exemplary embodiment of delivery system 200 according to the present invention, multiple securing wires may be used to form small profile loops instead of only one for each leg and the common body of the stent (i.e., 240, 230 and 270). In such an embodiment, the wires may be formed with tapered ends so as to reduce the possibility of a crowded arrangement of securing wires and closed structures. It is also to be understood that in an exemplary embodiment of delivery system 200 according to the present invention, a single securing wire such as 240, 230 or 270 may be threaded back-and-forth through multiple pairs of holes so as to form multiple small profile loops for secunng more than one closed structure of a given portion of the stent. In such an embodiment, the wire may be tapered for the same reason earlier given. It is to be understood that any combination of the two embodiments above may be utilized. Thus, 2 or more securing wires (which may be tapered) may each be threaded back-and-forth through multiple pairs of holes, while one securing wire may be threaded through only one pair of holes, etc.

The aorto-iliac type of delivery, which may use two access sites, may be used for placement of bifurcated stents in the biliary system or in hemodialysis grafts.

The present invention thus permits an advantage anywhere there is a bifurcated anatomical structure. This invention comprises a coherent element that can maintain all three lumens forming the Y-shape. A stent according to the present invention formed from one contiguous main body and two legs may eliminate all possible problems associated with Y-shaped stentings using separate stents. Separate stents need to be positioned in close apposition to each other to form the best possible seal and prevent tumor invasion (provided a covered stent is used) (Peterson, 1995). If any T, Y or V shape configurations are achieved with separate stents, the angled portion of the tubular structure remains the weakest.

Stents which are commonly used for the creation of a complex configuration (such as the WALLSTENT and the Gianturco Z-stent) show lower than expected expansile force when they are arranged side-by-side. According to the inventors' in vitro measurements, the expansile force of two WALLSTENTS and two Z-stent, respectively, positioned side-by-side were lower than those measured at the center of a same-size single WALLSTENT and a Z-stent, respectively (Tables 2 and 1). The stent according to the present invention showed the most expansile force, even at the level of the bifurcation (Table 3). In asymmetrical side-by-side arrangement of two WALLSTENTS, the behavior of the free ends of the partially compressed stent poses an additional concern considering the damage free ends may do.

Except for isolated tracheal and/or bronchial lesions, self-expanding metal stents have not been used to maintain the lumen of the bifurcations. Apart from stent-grafts, which are widely used for treatment of abdominal aortic aneurysms, only the Dynamic tracheo-bronchial stent has been made as a bifurcated stent (Freitag, 1994).

In selecting the proper size of the bifurcated stent, one should take into account the different diameters of the vessel at both the proximal and the distal ends of the stent. Ideally, the best possible matching between the diameters of the vessel and the stent would result in a wedge-effect. This wedge effect may be utilized to fix the stent within the vessel, preventing distal migration and possibly reducing intimal hyperplasia induced by a pressure that is higher than ideal. In a comparative experimental study, it turned out that of the Palmaz stents, WALLSTENTS and the Memotherm nitinol stents, none appeared to be preferable to the others regarding neointimal formation in the short- to mid-term follow-up period (Schurmann, 1996). At this time, the advantage of using a flexible vs. a rigid stent, or whether a balloon-assisted deployment is more advantageous over a self-expanding delivery mechanism with regard to preventing the production of intimal hyperplasia has not been established. As for a nitinol bifurcated stent, a possible flared proximal end of the stent may further improve the fixation of the stent if it is necessary.

The following general description may further provide one with guidance in selecting an appropriately sized stent. The stent may be inserted into the body in a completely elongated state. When the stent is allowed to assume its unconstrained size and shape, it may be significantly shortened. As the stent is first shortened, a small decrease in length may result in a relatively large increase in stent diameter. As the stent approaches its completely unconstrained state, however, this relationship is less pronounced, and a proportionate decrease in length may result in a much smaller increase in diameter. As a result, if a stent leg or common body with a diameter of 12 mm is deployed in a vessel with a diameter of 10 mm, that leg or common body may remain significantly elongated. This characteristic, though, may be advantageous if the tissue of the vessel is flexible. Data gained with other stents (e.g., Z-stent) have shown that the wall of a tubular structure (vessel, biliary tree, etc.) is readily, gradually, and quickly dilated and the stent is able to assume its unconstrained size within hours to days.

In the inventors' tracheobronchial study, described in the Example below, the inventors observed that both the stent legs and the common body changed in diameter and length even two weeks after stent placement.

The present invention may also be used in the treatment of aneurysms. The successful treatment of an aortic aneurysm "either abdominal (AAA) or thoracic (TAA)] depends on completely excluding it from the circulation. Therefore, incompletely fixing a stent-graft may result in persistent flow within the aneurysm sac. These perigraft leaks, also called endoleaks, can occur because of incomplete fixation at the proximal and distal ends. Endoleaks complicate between 8–44% of endovascular AAA repairs. There is experimental and clinical evidence that endoleaks can cause aneurysm rupture (Bakal, 1998).

Abdominal Aortic Aneurysm Treatment

Short infrarenal necks (<2 cm) may increase the risk of a proximal endoleak. In these cases, deploying the proximal fixation stent, typically a Z-stent, of an endovascular graft in the juxtarenal rather than in the infrarenal aorta can potentially prevent a proximal leak. The bare portion of the anchoring stent is placed across the renal arteries, with the covered portion beginning at the infrarenal level. Serious concern remains that any proximal dislodgment of the stent-graft (due to endoluminal migration and/or to shrinkage of the aneurysm) may threaten with occlusion of the renal artery(ies).

AAAs with non-short infrarenal necks may also be treated by placement of a covered bifurcated stent-graft. The covering material should be thin and stretchable enough to be able to follow the movements of the weave. The possible covering materials include woven Dacron, non-thrombogenic polyurethane, ultrathin and somewhat elastic PrTFE, polyester (commercially available from Tetko Inc. in Briarcliff Manor, N.Y.), and any other suitable materials that are biocompatible and may follow the movement of the weave of the stent. Woven Dacron may be coupled to the stent using polypropylene monofilament sutures. In one embodiment, it may be coupled to the stent using 5-0, 6-0, or 7-0 sutures (Ethicon). Ultrathin and somewhat elastic PTFE may be coupled to the stent in the same manner as the woven Dacron. Nonthrombogenic polyurethane may be coupled to the stent using glue or heat. In other embodiments, Teflon or silicon compounds may be coupled to the stent using any suitable means above described.

Figure 8:
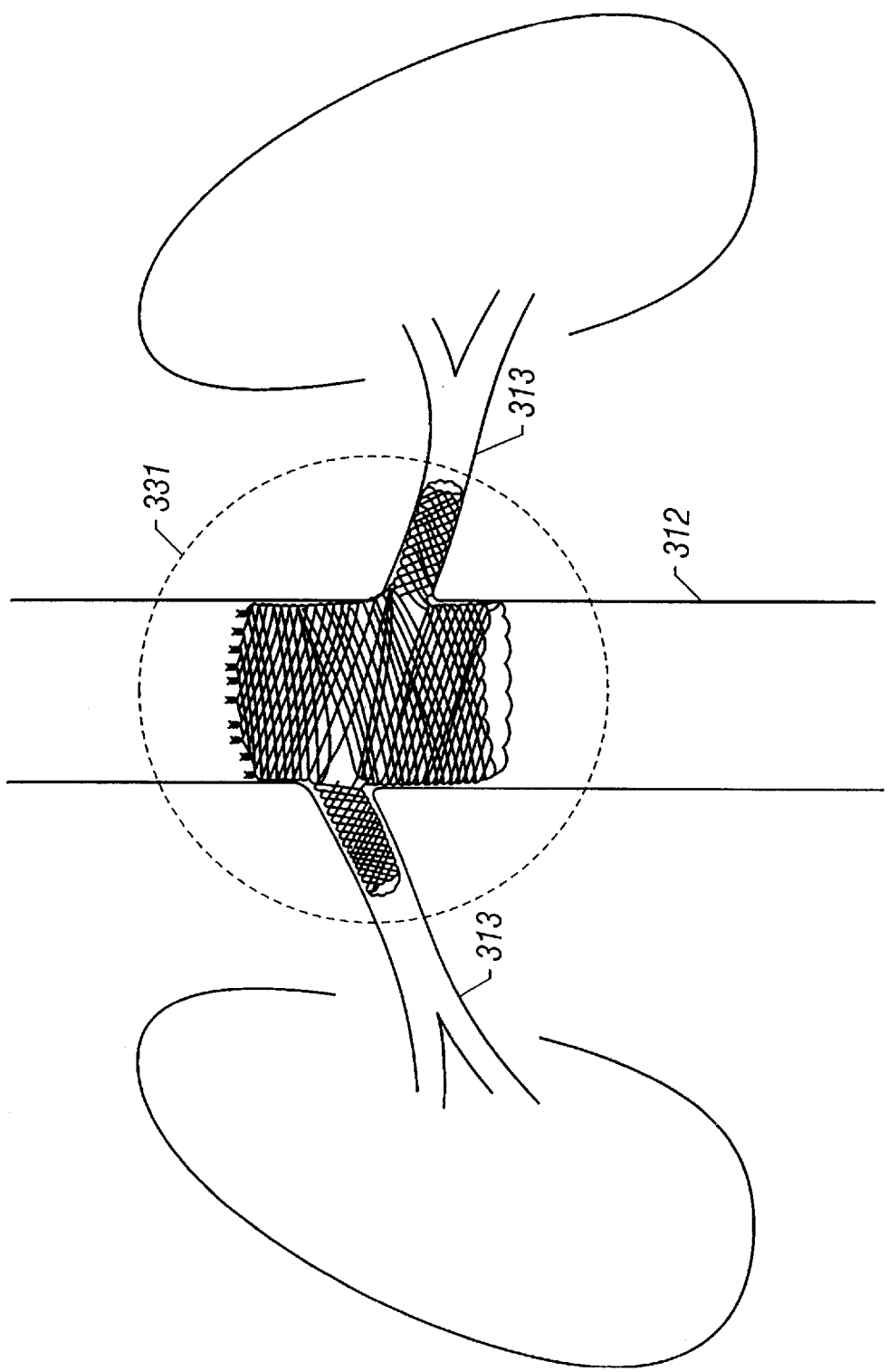
FIG. 8 is a front view of a trifurcated stent in a delivered position according to one embodiment of the present invention.

Using a stent according to the present invention, a covered trifurcated stent may be created. In this embodiment of the invention, the stent 300 has a common body 310 and two legs 320 (FIG. 7). The common body 310 (or suprarenal trunk) of the stent 300 will be placed into the lumen of the abdominal aorta, whereas the legs 320 are placed into the main renal arteries. The third leg 305 (or infrarenal trunk) will also be placed in the abdominal aorta, but it will be located below (or caudad) of the renal arteries. Although an appropriate portion of the stent 300 depicted in FIG. 7 may be covered, this covering is not shown for the sake of clarity. According to this embodiment, the lumen of the juxtarenal portion 331 of the aorta 312 together with those of the renal arteries 313 should be maintained first with the trifurcated stent-graft (FIG. 8, again, the graft material is not shown for the sake of simplicity), then another covered stent-graft (a straight tube graft or a bifurcated stent-graft) may be positioned into the distal abdominal aorta. The two stent-grafts should then be anastomized to each other, creating a completely sealed endograft. To achieve a good contact/connection between the two stent/stent-grafts with an appropriate seal, the straight tube stent or the common body of the bifurcated stent may be preferably flared.

The potential advantages of this embodiment include: (1) the shortness of the proximal aortic neck of the aneurysm will not be a limiting factor in selecting patients suitable for endovascular repair of stent-grafts; (2) the potential hazard from distal embolization and/or occlusion of the renal arteries can be eliminated; and (3) complete exclusion of the aneurysmal sac can potentially be achieved because the stent-graft will be anchored in the intact suprarenal portion of the aorta.

Figure 27A:
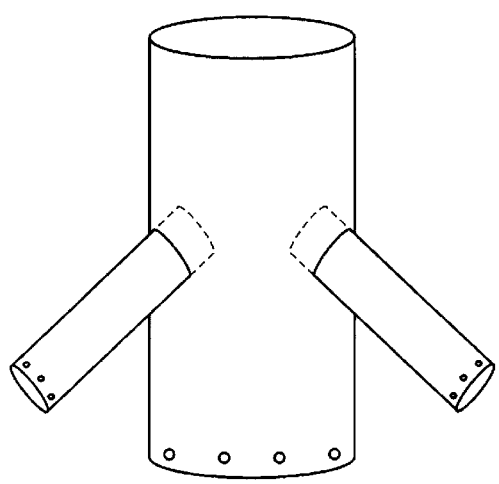
FIG. 27A is a perspective view of templates arranged for use in forming a trifurcated stent according to one embodiment of the present invention.
Figure 27B:
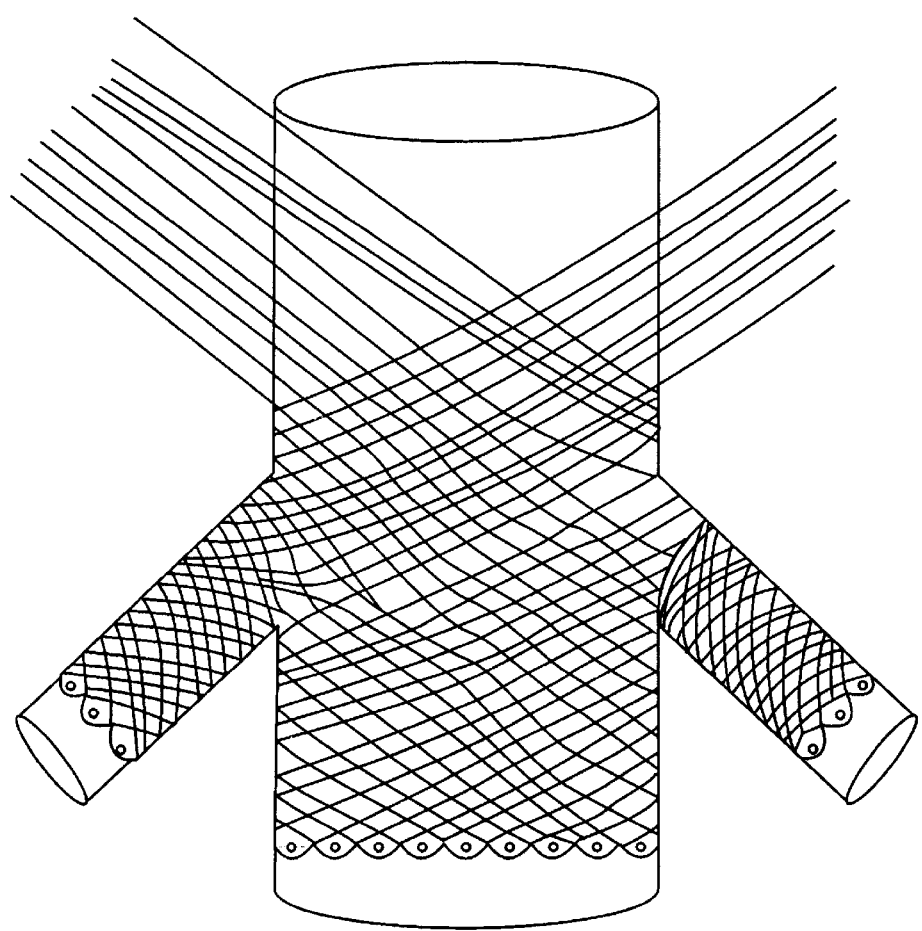
FIG. 27B is a perspective view of templates arranged for use in forming a trifurcated stent and wires woven thereon according to one embodiment of the present invention.

The weaving for this embodiment is similar to that which is used to create a bifurcated stent according to the present invention. To produce the trifurcated version, the weaving process should be started on three templates as above described. According to the inventors' studies, a minimum of 4 wires may be used to form the smaller (renal) legs 320 of the stent. The common trunk 310 of the stent, where all the wires are used for weaving the stent structure, may be formed with the largest diameter. This portion of the stent will be placed more cephalad (suprarenally, or, in other words, closer to the head) into the aorta. The weaving may be started on the two legs and the common trunk in separate stands. As in the case of the bifurcated stent, the templates for the legs may then be joined with the template of the common trunk as shown in FIG. 27A, and the plain weaving may be continued as above described and shown in FIG. 27B. The assembly may then be heated and cooled as described above, and reshaped and reheated as described above as needed.

The trifurcated stent may be delivered in the following manner. The delivery system depicted in FIG. 6 may be modified using the same materials described above to include a third tube such that both legs and both the lower and upper portions of a common trunk may be secured to tubes in the manner above described. The stent may then be so secured. Then, a right femoral artery access may be established by placing an introducer sheath in it. Two steerable guidewires may then be inserted from a cranial approach (from an axillary, brachial, or carotid artery) into the aorta. Using a foreign body retrieval device (preferably a snare), both of them may be pulled through the right femoral artery access. Each of the guidewires may be pulled through the lumen of the stent legs still outside the body. The stent may then be inserted and advanced into the abdominal aorta over a third guidewire placed into the lumen of the delivery system. From the cranial arterial access, a guidewire may be placed into each renal artery. The stent's proper orientation may be facilitated by placing markers on the dedicated portion of the stent. The guidewires should preferably be marked as right and left on their segments which are outside the body so that one can avoid twisting the stent. Once both renal wires are in place, the securing nitinol wires used to hold the stent legs to the common body as well as to the delivery system may be released one by one. In the final stage of the procedure, the securing wires holding the common body of the stent may also be released.

Thoracic Aorta Aneurysm Treatment

The thoracic aortic aneurysm (TAA) can be treated by less invasive endovascular strategies for patients considered at high risk for conventional surgery. Using the stent-grafts currently available for this purpose, the aortic neck proximal and distal to the aneurysm must have a diameter $\leq 40$ mm and a length >15 mm (Semba, 1998). Shorter proximal necks cannot be safely treated with a stent-graft because of the potential occlusion of the left subclavian artery. The positioning of the proximal anchoring stent of the stent-graft across the left subclavian artery offers a possible alternative to eliminate this problem. Deployment of another stent into the left subclavian artery to maintain its lumen is another possibility. Both solutions, however, carry some risk of distal embolization and arterial occlusion.

Figure 9:
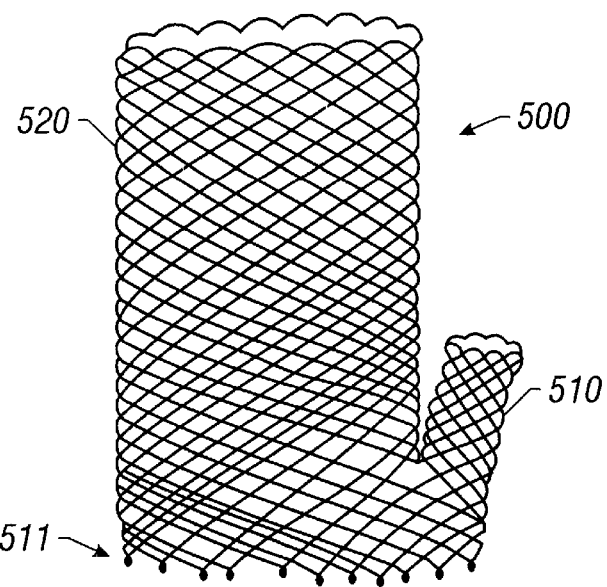
FIG. 9 is a front view of a bifurcated stent according to one embodiment of the present invention.
Figure 10:
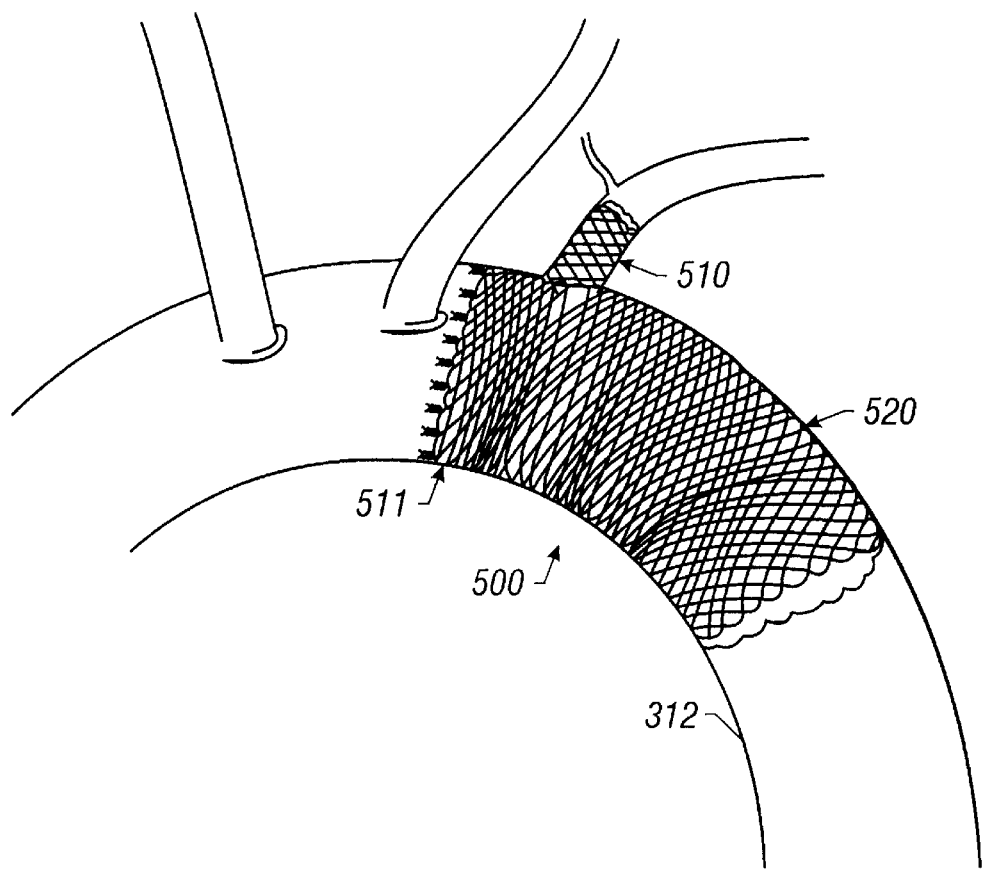
FIG. 10 is a front view of a bifurcated stent in a delivered position according to one embodiment of the present invention.

As shown in FIGS. 9 and 10, a bifurcated stent-graft 500 according to the present invention having a smaller caliber leg 510 for the left subclavian artery and a larger trunk 520 for the aortic lumen may solve the problem. This stent-graft effectively seals the lumen of the aneurysm and simultaneously maintains the patency of the subclavian artery. For the sake of simplicity, the graft materials that may be used to cover all or part of the stents of stent-grafts 500 are not shown in FIGS. 9 and 10. Stent-graft 500 depicted in FIGS. 9 and 10 will be understood to have a first leg, leg 510 for example, a second leg, trunk 520 for example which resides in aorta 312 as illustrated in FIG. 10, and a common body having a portion 511 that is proximate portions of both leg 510 and trunk 520, and which is formed from the wires forming both leg 510 and trunk 520. FIG. 10 depicts a delivered stent-graft 500.

Stent graft 500 may be formed using plain weave as described above, and may be delivered using the Aorto-Iliac Application delivery system above. The concept of maintaining the lumen patency of the larger branches of the aorta adjacent to the aneurysm with the same stent-graft used to treat the aneurysm itself may be utilized to solve the most frequent and serious problems currently associated with endografting of AAA and TAA.

Aortic Arch Reconstruction

One or more of the present bifurcated stents may be used for reconstruction of the aortic arch. If the disease affects both the aorta and one or more large vessels (such as the brachiocephalic, left carotid or left subclavian artery) the treatment utilized should be designed to maintain the aortic lumen without compromising the blood flow in the side branches. The underlying pathological condition (such as an aneurysm) may require that the treatment involve the use of a stent-graft in order to exclude the aneurysmal sac from the circulation by creating a new lumen. This treatment is depicted in one embodiment in FIG. 10, which shows treatment of the TAA with a bifurcated stent-graft (although the cover material is not shown) according to the present invention.

Figure 20:
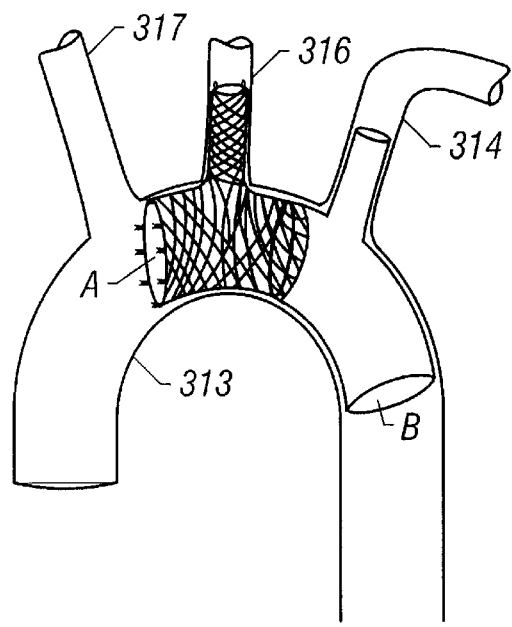
FIG. 20 depicts two bifurcated stents delivered into the aortic arch according to one embodiment of the present invention.
Figure 21:
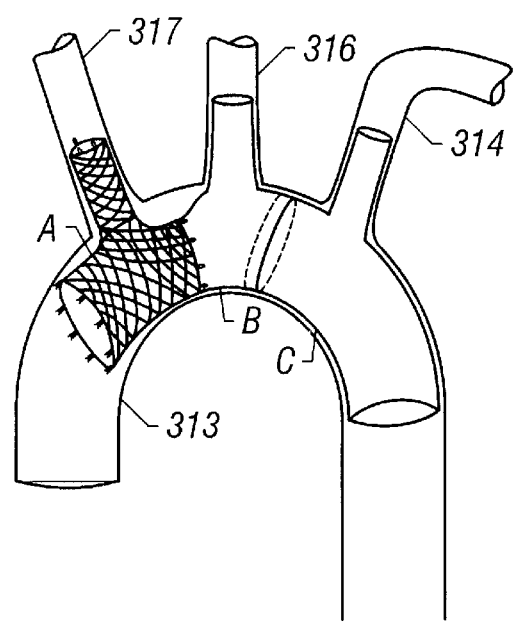
FIG. 21 depicts three bifurcated stents delivered into the aortic arch according to one embodiment of the present invention.
Figure 22:
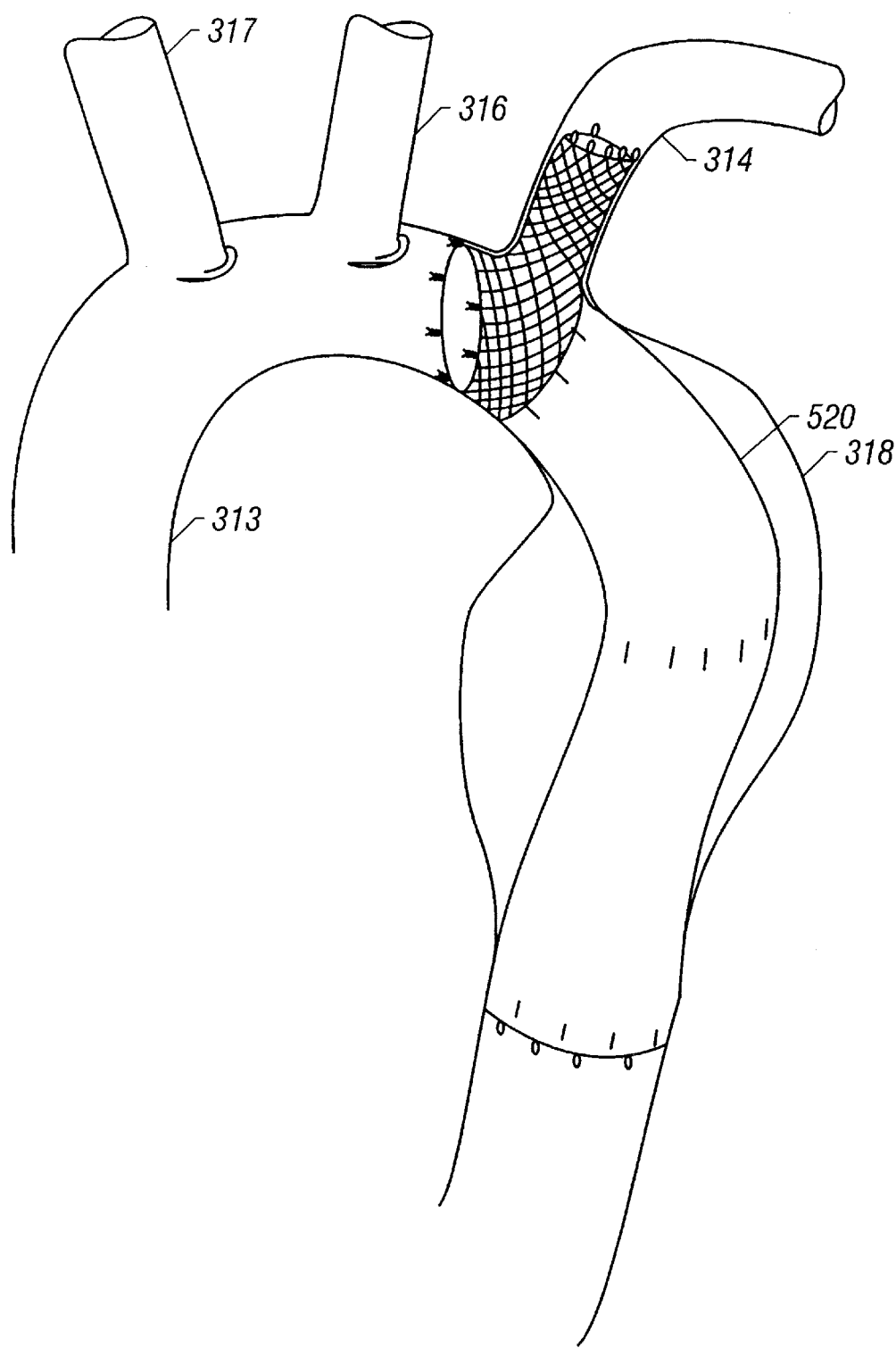
FIG. 22 depicts a partially-covered bifurcated stent delivered into the aortic arch and sealing an aneurysmal sac according to one embodiment of the present invention.

In other cases involving the stenosis of large arteries (e.g., the subclavian, and the common carotid arteries) along with that of the aorta, the aortic lumen can be reconstructed using combinations of uncovered bifurcated stents. FIGS. 20–22 depict the aortic arch 313, the left subclavian artery 314, the carotid artery 316 and the right subclavian artery 317. FIG. 20 also depicts two bifurcated stents: the first of which, bifurcated stent A, may be delivered using delivery system 200 depicted in FIG. 6 in the manner described above. After bifurcated stent A is delivered, bifurcated stent B (the second of the two) may be delivered using the same delivery system and in the same way. As depicted in FIG. 20, the two bifurcated stents may be delivered such that A overlaps B somewhat. The weave of bifurcated stent B is not depicted in FIG. 20 for the sake of simplicity of illustration.

FIG. 21 depicts three bifurcated stents, A, B, and C, delivered in the same manner as the two bifurcated stents depicted in FIG. 20, and with the same type of overlap. In some situations, a combination of a bifurcated stent-graft and a stent-graft that is formed using the weaving methods disclosed herein, but that is straight, may also be used. Thus, the doctor is free to utilize any combination of stents to achieve his or her purpose.

The extent to which the current bifurcated stents are covered may be varied according to the treatment method needed. As shown in FIG. 22, the portion of trunk 520 (which occupies the portion of aortic arch 313 downstream of left subclavian artery 314, and which is designed to seal aneurysmal sac 318) is covered, while leg 510, which occupies left subclavian artery 314, and the portion 511 of stent 500, which is positioned upstream of left subclavian artery 314 are uncovered.

This embodiment may be advantageous when the thoracic aortic aneurysm affects the segment of the aorta immediately surrounding the orifice of left subclavian artery 314, or in other words, when the cephalad neck of the aneurysm is very short. In this situation, the use of a straight stent-graft (that is, a non-bifurcated stent-graft) is controversial because the shortness of the cephalad neck of the aneurysm virtually eliminates the possibility of safely and adequately achieving fixation of the straight stent-graft without compromising blood flow in left subclavian artery 314. Using the embodiment of the present invention depicted in FIG. 22, however, uncovered leg 510 is designed to maintain the patency of left subclavian artery 314 while the covered portion of trunk 520 should effectively seal aneurysmal sac 318, thereby preventing endoleak from left subclavian artery 314. If left subclavian artery 314 suffers from aneurysmal dilation, a completely covered bifurcated stent-graft should be used. Either embodiment—partially or completely covered—may be delivered using delivery system 200 as described above.

Figure 40:
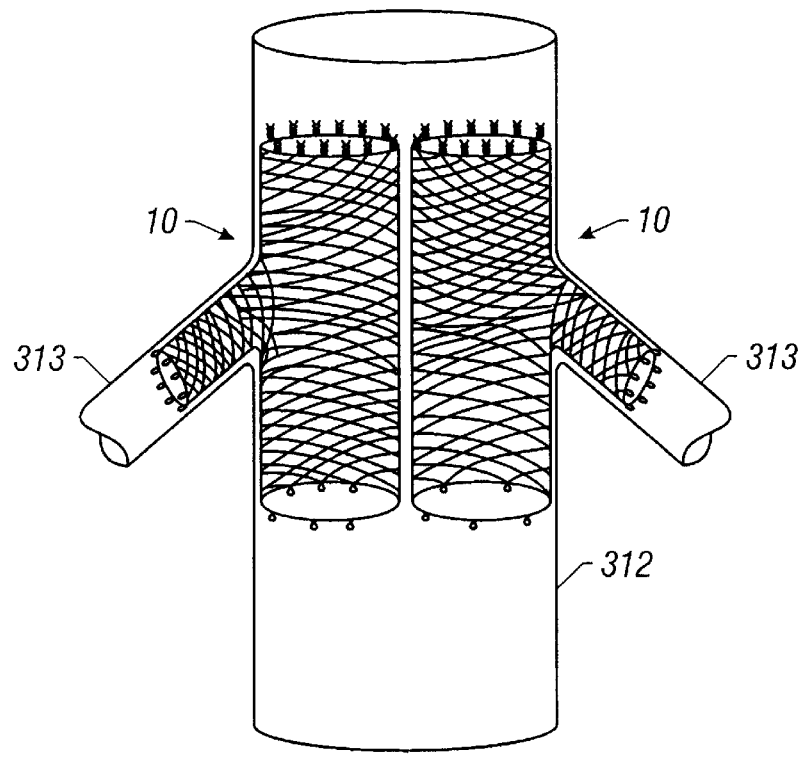
FIG. 40 is a front view of two bifurcated stents placed in side-by-side relationship with each other in the aorta according to one embodiment of the present invention.
Figure 41A:
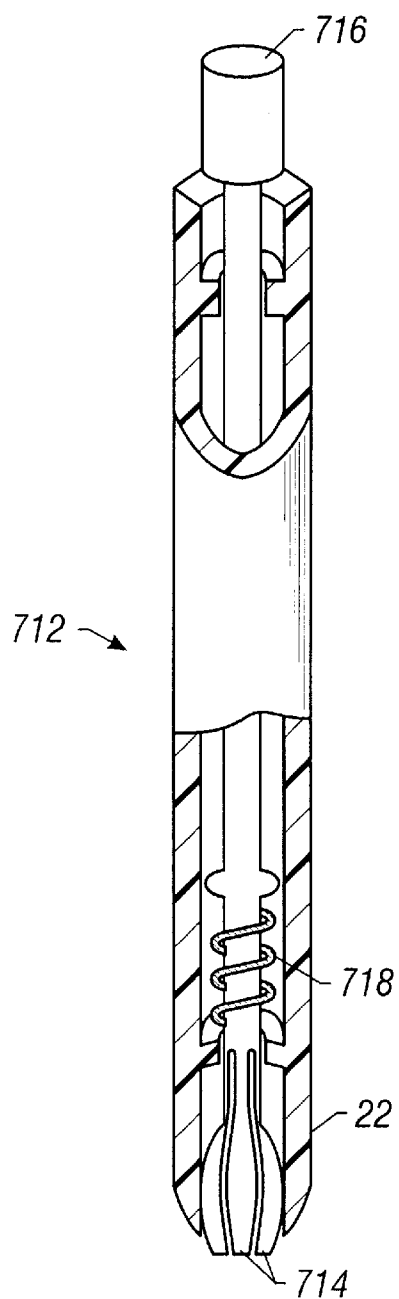
FIG. 41A is a perspective, partial cross-sectional view of a tool for twisting the wire ends of a woven stent according to one embodiment of the present invention.
Figure 41B:
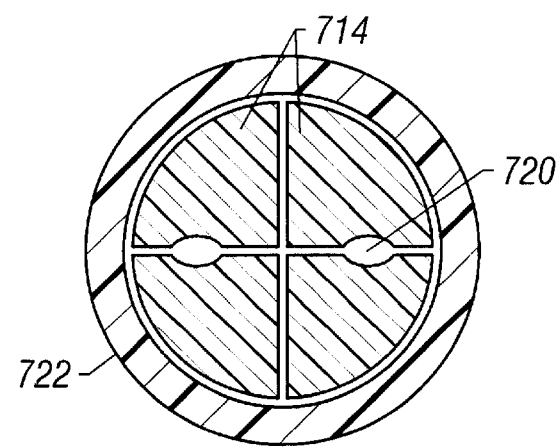
FIG. 41B is a cross-sectional view of the jaws and outer housing of the tool illustrated in FIG. 41A.

Aorta and Bilateral Renal Artery Replacement Using Two Bifurcated Stents Positioned Side-By-Side As shown in FIG. 40, two bifurcated stents 10 (stent-grafts, not shown, may also be used) are used side-by-side in aorta 312, and renal arteries 313. In this embodiment, the bifurcated stents 10 (or bifurcated stent-grafts 500, not shown) may be secured to two delivery systems 200 and delivered as described above. They may be released simultaneously so as not to allow either to expand at the expense of the absence of the other. In one embodiment, each trunk occupies about 50% of the intraluminal space available in the aorta.

The use of two uncovered bifurcated stents as just described is warranted if the abdominal aortic aneurysm has a short proximal neck (that is, one that extends only slightly upstream of the renal arteries) that makes it virtually impossible to use stents having a graft material that would block renal circulation. Depending on the length of the aneurysmal neck and/or the possibility of endoleak from the renal arteries, the renal legs of the bifurcated stent may be covered or uncovered. If the renal circulation would not be compromised by covering the renal legs, the portion of the trunk located upstream of the renal arteries may be left uncovered.

Combined Treatment of Aneurysms Consisting of Stent Placement and Transcatheter Embolization In one embodiment of the present invention, the bifurcated (and in some lesions even the trifurcated) stent may be used for aneurysm treatment without being equipped with a graft material. In this embodiment, the "naked" stent may serve as a scaffold for developing an endothelial layer on the newly formed vessel lumen, while the aneurysmal sac may be excluded from circulation by transcatheter embolization.

Figure 30:
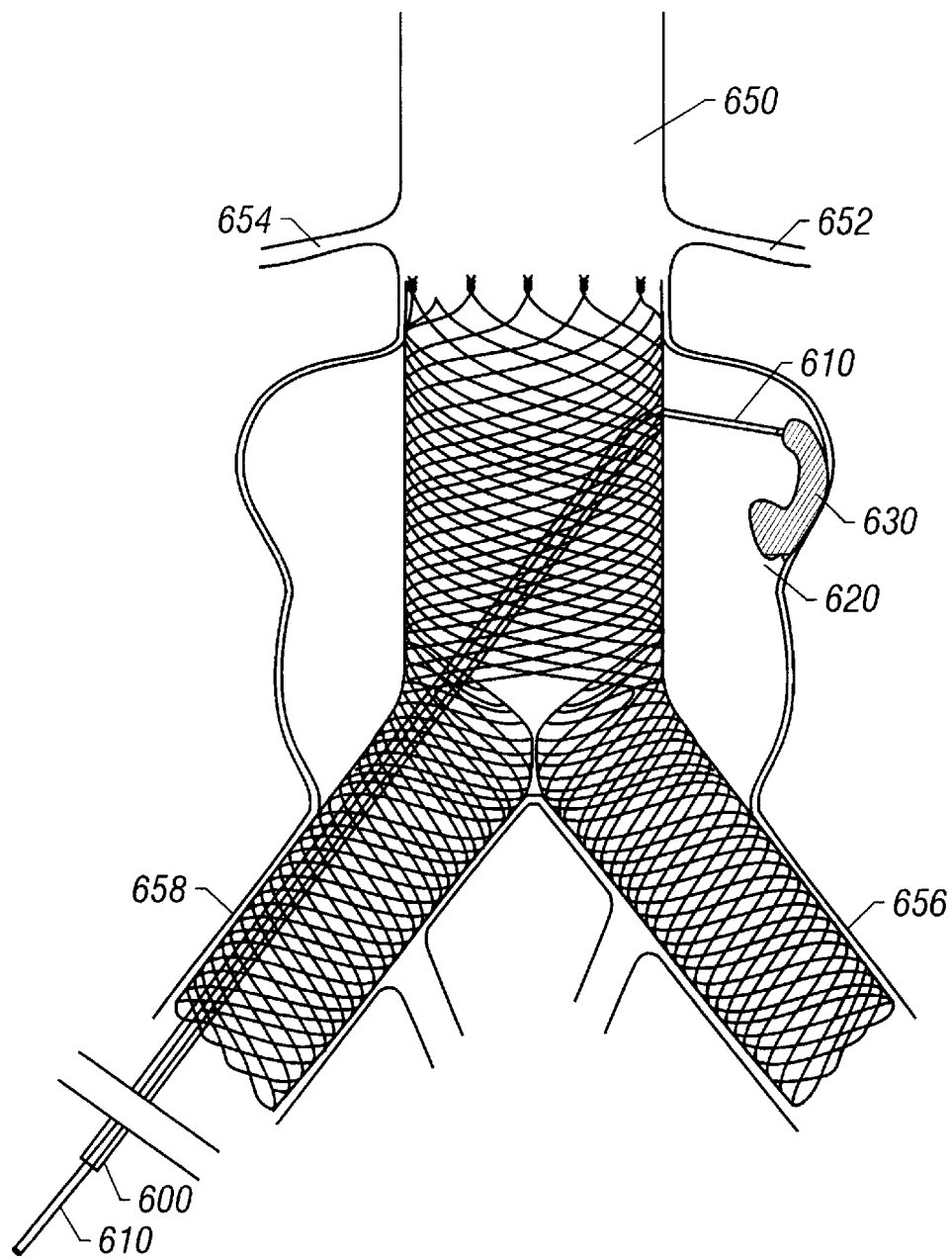
FIG. 30 is a front view of an abdominal aortic aneurysm being treated by transcatheter embolization according to one embodiment of the present invention.

Generally, the stent may be delivered into place, and an embolic agent may be inserted into the surrounding aneurysmal sac as shown in FIG. 30, which depicts the abdominal aorta 650, the left renal artery 652, the right renal artery 654, the left iliac artery 656, and the right iliac artery 658.

The stent may be delivered into place as above described. As shown in FIG. 30, once the stent is in the appropriate position, an angiographic catheter 600 (5-French to 7-French) that is chemically compatible with the embolic agent (not polyurethane when the embolic agent contains DMSO) may be inserted and advanced into the lumen of the stent. In advancing the angiographic catheter into the lumen of the stent, one may use the same guidewire which may have been used in delivering the stent. However, one may advance the angiographic catheter without the use of a guidewire. An adequately sized microcatheter 610 (2-French to 4-French) that is chemically compatible with the embolic agent may then be advanced through the angiographic catheter, on an appropriately-sized guidewire (0.014-inches to 0.025-inches). The tip of the microcatheter may then be led through the weave of the stent into the aneurysmal sac 620. If the openings in the weave of the stent are approximately 2.0 to 2.5 mm, 600 may also be advanced into the aneurysmal sac. An embolic agent 630 may then be inserted into the aneurysmal sac through the microcatheter. Embolic agent 630 may be chosen so as to be: non-toxic, non-irritant/reactive to the tissues; easily handled; suitable for continuous injection; adequately radiopaque; capable of filling the space contiguously without leaving unoccupied spaces; and non-fragmented, thereby not getting back through the stent's weave into the newly formed lumen which could result in peripheral embolization.

Although several fluid embolic materials (alcohol, polyvinyl alcohol, cyanoacrylates, Ethibloc etc.,) are available for transcatheter vessel occlusion, none of them is considered ideal or even suitable for this purpose. Recently, a nonadhesive, liquid embolic agent, ethylene vinyl alcohol copolymer (EVAL), has been used clinically for treatment of cerebral AVMs in Japan (Taki, AJNR 1990; Terada, J Neurosurg 1991). The co-polymer was used with metrizamide to make the mixture radiopaque and may serve as the embolic agent for the present invention.

Very recently, a new embolic agent (similar to EVAL), EMBOLYX E (ethylene vinyl alcohol copolymer) (MicroTherapeutics Inc., San Clemente, Calif.) was developed, which was designed for aneurysm treatment (Murayama, Neurosurgery 1998), and may be utilized as an embolic agent in one embodiment of the present invention. The embolic agent is composed of a random mixture of two subunits, ethylene (hydrophobic) and vinyl alcohol (hydrophilic). Micronized tantalum powder is added to it to obtain an appropriate radiopacity, and DMSO (di-methyl sulfoxide) is used as an organic solvent. When the polymer contacts aqueous media, such as blood, the solvent should rapidly diffuse away from the mixture causing in situ precipitation and solidification of the polymer, with formation of a spongy embolus and without adhesion to the vascular wall. Any kind of material with characteristics similar to those of EMBOLYX E may be used as an embolic agent for the present invention.

Both abdominal and thoracic abdominal aneurysms may be treated as above described. In some other locations (e.g., external iliac artery), pseudoaneurysm and/or tumor-induced corrosive hemorrhage may also be treated as above described.

The size of the delivery system that may be used to deliver a bifurcated stent without a graft cover may be sufficiently small, such that insertion of the stent into the vessel may take place following a percutaneous insertion. The delivery system would also be well-suited to negotiating through tortuous vascular anatomy. The treatment described above may be performed using interventional radiology techniques, thereby eliminating the need for surgery. The embolization may occlude the lumbar arteries from which the excluded aneurysmal sac is frequently refilled. As a result of using the treatment described above, the leak from the patent lumbar arteries may be eliminated.

The following examples are included to demonstrate illustrative embodiments of the invention. It should be appreciated by those of skill in the art that the techniques disclosed in the examples which follow represent techniques discovered by the inventors to function in the practice of the invention, and thus can be considered to constitute illustrative modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Below, the inventors present the results of an in vitro study designed to establish the characteristics (ie. expansile or radial force and flexibility) of the inventors' new bifurcated stent design and compare these characteristics to those of the Gianturco-Rösch biliary Z-stent and the WALL-STENT. In addition, the inventors also present the inventors' preliminary results with the tracheobronchial application of the new stent in the pig.

As discussed above, the self-expandable bifurcated stent according to the present invention has a Y-shape (Y-stent) comprising a common main body and two legs that are made as one coherent element.

The stents used for this study were made by hand weave. A wooden stand with a circular plate was used for weaving the stents. One of the ends of the tubular copper template was equipped with multiple holes around its circumference. The midportion of each wire was hanged on metal pins placed through these holes and secured to the template with some copper wire. A 100 gram weight was attached to each free end of the nitinol wires. The template with the attached wires was then placed through the wide central hole of the circular plate of the stand in an up-side-down position. In this arrangement, the end of the template with the holes made for wire attachment faced down. A central weight (approx. 600 g) was hanged on this end of the template, and the nitinol wires with the 100 gram weights were led over the flat surface of the circular plate.

The wire ends were evenly arranged around the circumference of the circular plate. The 100 gram weights and the central weight kept the wires under tension and in balance. The weave started with two wire ends. One of the wire ends (e.g., the left one) was crossed over the right one. In clockwise direction, the left wire end was crossed similarly over the corresponding right one. This move was continued until the circle was finished. The direction of the move was then reversed, and the wire crossings were done counter-clockwise. The tightness of the weave (i.e. the angle between the wires) was adjusted by changing the central weight. An increase in the central weight resulted in a looser weave (decreased angle between the wires) and vice versa.

After the plain weave of nitinol wires was completed on the metallic template, the stent/template unit was heated to 500° C. for 12–15 min. After cooling to room temperature, the stent wires possessed superelastic properties.

For this in vitro study, Y-stents according to the present invention were made using 12 0.005-inch nitinol wires (Shape Memory Applications, Santa Clara, Calif.). The outer diameter of the common body and the legs was 8.5 mm and 5.5 mm, respectively. The characteristics of the Y-stent were compared to a four-body Gianturco-Rösch biliary Z-stent® (Cook Inc., Bloomington, Ind.) and a WALLSTENT (Schneider, Minneapolis, Minn.). Each body of the Z-stent was constructed of 0.012-inch stainless steel wire with 6-bends at each end and a 12 mm outer diameter. The WALLSTENT was made of 24 surgical grade stainless steel alloy wires (0.006-inch) and had an unconstrained outer diameter of 9.5 mm.

In addition, straight, cylindrical nitinol stents were fabricated with a uniform outer diameter of 13 mm to evaluate the effect of varying the number of wires and weave tightness on expansile force. Stents were constructed from six, eight, and ten 0.011-inch super-elastic nitinol wires and the tightness of the weave was varied in two stents made of six wires.

The expansile force of the stents was measured using the method described by Fallone (Fallone et al., 1988). Measurements made by this method are based on the fact that the final radius to which the stent expands within a tubular structure (e.g., a blood vessel) depends on the pressure exerted by the wall of the structure on the stent. At equilibrium, the pressure exerted by the wall on the stent is equivalent to that produced by the stent on the wall. The response of the stent to external pressure can be measured by using a non-elastic collar-type device placed around the stent.

An apparatus comprising a non-elastic paper strip and a tubular spring gauge with a capacity of 500 g was fabricated to measure stent expansile force. One end of the non-elastic paper strip was fixed and the other end was attached to the spring gauge, forming a circular collar with an adjustable diameter. The stent was placed within the collar. Pulling on the spring gauge caused uniform pressure to be exerted upon the stent, thus decreasing the radius of the stent from the original value of $R_o$ to R. The change in radius was expressed as the circumferential displacement measured in mm directly on the paper strip. The force (measured in grams) needed to cause a 10 mm circumferential displacement of the stent was used to compare the expansile force of each stent design.

The unit "grams" has been used herein as a measure of force. Although the correct unit of force is the "dyne", which is equal to the mass in grams multiplied by the gravitational constant, the inventors believe that the average reader will have a better idea about the size of force when the associated mass unit (grams) is specified. For the Z-stent and WALLSTENT, the relationship between the force exerted by the collar and the circumferential displacement of the stent was measured at the mid-part of the stent. Initially, measurements were made on a single stent and then a second identical stent was placed alongside the former one and the measurements were repeated. This was done to simulate two stents being placed side-by-side to treat a lesion occurring at a bifurcation. Taking into account the fact that the multiple-body Gianturco-Rösch biliary stents are the weakest at the point where the bodies are joined by nylon monofilament suture, measurements were made at the mid-portion of the second body of these stents. The Y-stent of the present invention was measured at the mid-portion of the common body and at the bifurcation (junction of legs and common body). Measurements were obtained 10 times on each stent and the results were averaged.

To establish the flexibility of the stents, the luminal diameter at the mid-portion of the stent was measured while holding the stent at both ends and bending it 180° in the middle. A transformation ratio was then calculated using the formula:

$$"D0-D1]/D0 \qquad "1]$$

where $D0$ is the luminal diameter of the stent before bending and $D1$ is the luminal diameter after bending. This test was performed 10 times on each stent and the results were averaged.

For statistical analysis, repeated ANOVA method (flexibility) as well as Student's t-test and Mann-Whitney U-test (expansile force) were used.

Animal Studies

Fourteen of the Y-shape stents of the present invention and the corresponding delivery systems were tested in the tracheobronchial systems of 9 pigs. First, the inventors fabricated and used bifurcated stents, the common body of which had a slightly elliptical cross-section with a larger frontal diameter (18 mm vs. their 15 mm a-p diameter). The height of the common body was 10–12 mm in these stents, while the legs were 2.8–3.1 cm-long and had a diameter of 9 mm.

A bifurcated delivery system was constructed from two 7-F Teflon tubings. A piece of a 14-F thin-walled Teflon sheath was pulled over the proximal halves of these tubings to hold them together. After gaining some experiences with the delivery system, the inventors covered the 7-F tubings in a longer segment, leaving free only the distal 15–17 cm of the tubings (which length corresponded with the totally stretched length of the stents). Four pairs of holes were made close to the end of each 7-F tubing and were arranged evenly around the circumferences of the tubings. The distance between the corresponding holes of each pair was about 4–5 mm. Two other pairs of holes were also made on the same tubing approximately 14–16 cm away from the distal holes. 0.009-inch superelastic nitinol wires were used to secure the stent's ends to the delivery system. First, four securing nitinol wires were placed through the lumen of one of the 7-F tubings. These wires were placed into the lumen through the proximal holes positioned close to the distal end of these tubings. One of the legs of the bifurcated stent was pulled over the 7-F Teflon tubing and the four prepared superelastic nitinol wires were led through the stent mesh at its distal end. Actually, the angles made from the mid-portion of the stent-wires were used to secure the stent to the delivery system.

The distal ends of the securing nitinol wires were then threaded through the distal holes of each hole-pair, forming a low-profile tight nitinol wire loop between the two corresponding holes of each hole-pair. The tight wire loops held the end of the stent leg firmly to the tubing. The other leg of the stent was attached to the delivery system in the same way. The stent crown was secured to the delivery system using the same technique: altogether 4 other 0.009-inch securing nitinol wires were used (2 per tubing) to create a steady connection between the proximal part of the stent and the delivery system. The proximal hole-pairs created on the 7-F tubings were used for this purpose. Altogether 6 securing nitinol wires were placed in the lumen of each 7-F Teflon tubing.

The proximal ends of the securing nitinol wires were marked and separated from each other, forming two bunches of wires within each 7-F tubing: two of them were used for securing the stent crown, the other four to hold one of the legs of the stent. A 0.018-inch nitinol guidewire with a floppy tip (Microvena Corp.) was placed in the lumen of each tubing. The guidewires were able to move freely without interfering with the movement of the securing wires and vice versa.

The stents were deployed through an 8 mm or 8.5 mm diameter tracheal tubing under fluoroscopy. In the first stage of the delivery, the inventors canullated the main bronchi with the nitinol guide wires. Once the right position of the guidewires was achieved, the legs of the delivery system were advanced over the guide wires until the bifurcation of the stent was caught by the carina. At this point, the stent crown was released by pulling back the two securing nitinol wires in each 7-F tubings. Immediately after that, the stent's legs were released by withdrawal of the 4 securing nitinol wires on each side. The delivery system was then removed from the tracheobronchial system.

RESULTS

Part 1: In vitro Study

Expansile Force

The cumulative data from the measurements of the stents' expansile force is summarized below in Tables 1, 2 and 3 below. In each table, the designation Δ in the leftmost column of each table represents the circumferential displacement (in mm) of the stent in question. For example, a Δ of 2 mm indicates that the circumference of the stent in question was reduced by 2 mm, and the force necessary to effect that displacement was then recorded.

TABLE 1

Z-Stent, 6 Bends, Caliber: 12 mm

| Δ (mm) | Body Center | Between Bodies | Side By Side |
| --- | --- | --- | --- |
| 2 | 16 | 13 | 19 |
| 4 | 36 | 28 | 31 |
| 6 | 51 | 44 | 42 |
| 8 | 63 | 61 | 56 |
| 10 | 81 | 79 | 62 |
| 12 | 100 | 98 | 76 |
| 14 | 115 | 119 | 90 |
| 16 | 127 | 133 | 101 |
| 18 | 146 | 192 | 122 |
| 20 | 165 | | 142 |

TABLE 2

WALLSTENT 0.006" diameter wire, 24 wires

| Δ (mm) | Center | Overlap | Side by Side |
| --- | --- | --- | --- |
| 2 | 15 | 35 | 18 |
| 4 | 25 | 59 | 22 |
| 6 | 42 | 80 | 35 |
| 8 | 50 | 108 | 42 |
| 10 | 60 | 126 | 48 |
| 12 | 74 | 149 | 54 |
| 14 | 84 | 170 | 63 |
| 16 | 100 | 197 | 73 |
| 18 | 111 | 220 | 84 |
| 20 | 129 | 248 | 96 |

TABLE 3

Y-Stent, 0.005" nitinol wire, 12 wires, caliber: trunk - 8 mm, branch - 5 mm

| Δ (mm) | Trunk | Junction |
| --- | --- | --- |
| 2 | 44 | 51 |
| 4 | 91 | 109 |
| 6 | 126 | 143 |
| 8 | 158 | 155 |
| 10 | 167 | 164 |
| 12 | 175 | 191 |
| 14 | 184 | |
| 16 | 202 | |

The force (measured in grams) needed to cause a 10 mm circumferential displacement of a single four-body Z-stent was 81 g, and 62 g was required for two four-body Z-stents placed side-by-side ($p<0.0001$). For the WALLSTENT, 60 g and 48 g were needed, respectively ($p<0.0001$). The values for the common body and the bifurcation of the Y-stent were 167 g and 164 g, respectively. These results indicate that the expansile force of a nitinol Y-stent constructed according to the present invention from 12 0.005-inch nitinol wires is greater than the force exerted by a 6-bend Z-stent fabricated from 0.012-inch stainless steel wire or a WALLSTENT made of 24 stainless steel alloy wires (0.006-inch). The bifurcated stent exhibited significantly greater expansile force than the Z-stent or WALLSTENT ($p<0.0001$). The expansile forces measured at the common body and the bifurcation of the Y-shape stent were almost identical ($p<0.0092$).

Stent Flexibility

The four-body Gianturco-Rosch biliary Z-stent started to lose its lumen in the mid-portion of the stent at an angle of 40°. The lumen collapsed completely at 90–100°. When the WALLSTENT was bent, the luminal diameter increased from 9 mm to an average diameter of 12.0 mm (range: 11.5–13.0 mm) at a bend of 180°. This means the transformation ratio was 33.3% (range: 27.7% to 44.4%). However, the stent shortened at the same time the luminal diameter increased. When the common body of the Y-stent of the present invention was bent 180° in the middle, the luminal diameter decreased from 8 mm to an average of 7.3 mm (range: 7.5–7.0 mm). The transformation ratio for the Y-stent was 8.75% (6.25–12.50%). The stent did not shorten during bending. The flexibility of the Y-shape stent was superior to both the Z-stent and the WALLSTENT ($p<0.0001$).

Part 2: Animal Evaluation

The stent placement was technically successful in 9 of 14 cases. Delivery system failure resulted in premature deployment (2 cases), twisting of stent legs during deployment (2 cases), and inability to release stent legs (1 case). Five stents migrated because the unconstrained stent diameter was smaller than the tracheobronchial system. Three of them were removed one week after stent delivery because of significant discrepancy between the size of the stent and the tracheobronchial system. Persistent cough occurred in 3 pigs because the stent legs were longer than the main-stem bronchi which resulted in distal bronchi placement.

Three animals were followed up for 8 wk, one animal for 4 wk after stent placement. All these stents remained patent, there were no pulmonary lesions related to the presence of the stents. These animals tolerated the stent well.

DISCUSSION

Due to the characteristics of nitinol wire, the Y-stent of the present invention can be stretched into low profile and deployed using its superelasticity. Therefore, after inserting the stent at the lesion, the stent should readily recover from its constrained state and a balloon catheter should not required. The unique contiguous weave of the design makes it possible to achieve virtually complete coverage of a lesion occurring at a bifurcation without gap formation. Therefore, it might be possible to use a single stent according to the present invention to treat this type of lesion, whereas now it requires special techniques and the placement of multiple stents.

In the present in vitro study, the Y-stent of the present invention demonstrated greater expansile force than the Z-stent or WALLSTENT. This study showed that two Z-stents or two WALLSTENTS positioned side-by-side exhibit lower radial force than a single stent of each type (p<0.0001). Therefore, the rationale for using Z-stents or WALLSTENTS positioned side-by-side is questionable.

There are many factors that influence the characteristics of a stent made by using a simple weave pattern such as the Y-stent and the WALLSTENT. The size and the number of the wires used to form the mesh, the angle created between the wires, and the shape memory properties of the wire will determine the physical properties of the tubular prosthesis. Therefore, stents of similar luminal diameter that possess completely different expansile force may be produced by altering the size and/or the number of the wires and the tightness of the weave.

Increasing the number of wires or the tightness of the weave can further increase the stent's radial force. It is well known that the angle between the wires of a stent, which is produced by plain weave (e.g., WALLSTENT), should preferably be greater than 90° (Wallsten, 1987). The greater the angle between the wires, the greater the expansile force of the stent. These characteristics, along with the excellent shape memory of nitinol wire make it possible to produce a Y-stent with a high radial force. A Y-stent having high expansile force may help treat rigid strictures, such as those caused by scar tissue formation or malignant tumors.

Stent diameter and wire-angle are also closely related. By increasing the angle between the wires, the inner diameter of the Y-stent increases, and inversely, by decreasing the wire-angle, the stent's inner diameter decreases and the stent elongates. This characteristic may be utilized for production of a wide variety of woven nitinol stents simply by re-adjusting the wire-angle and then re-heating the nitinol mesh. As a result, the weave, radial force, diameter, length, and shape of the nitinol stent can be secondarily modified after completing the primary weaving and heating processes. In the case of the WALLSTENT, the physical properties are imparted to the stent during the weaving process, and they cannot be changed later.

In addition to exhibiting a greater expansile force, the woven nitinol straight-stent and Y-stent demonstrated good flexibility. These features may allow these stents to be deployed in a tortuous curved structure while maintaining their luminal diameter and preventing the lumen from collapse, which may occur with the Z-stent.

The WALLSTENT and Y-stent reacted differently to 180° bending at their mid-portion. The inner diameter of the WALLSTENT increased, the wire mesh tightened, and the stent shortened, whereas the inner diameter, wire mesh, and length of the Y-stent remained virtually unchanged. The different behavior of the two stents can be in part ascribed to the closed structures of the woven nitinol stent.

The closed structures of the Y-stent are also an advantageous feature for stent delivery. These closed structures, created by bending the stent wires at about their mid-portions, as well as by using multiple twists or other means to couple the free ends of the stent-wires, allow for both ends of the stent to be secured to the delivery catheter. Using a delivery system made of two coaxially placed movable tubes, the stent can be repositioned even after 100% expansion prior to complete release. In addition, since the stent has no sharp wire ends, potential tissue laceration and perforation can be avoided.

These preliminary in vitro and animal studies have shown that the Y-stent woven with continuous nitinol wires has excellent self-expandable characteristics. This new stent design may be useful for the treatment of both vascular and non-vascular lesions occurring at bifurcations of tubular anatomic structures.

The good flexibility and high expansile force of the design may promote stenting tortuous lesions as well as bridging rigid strictures resulting from scarring or malignancy. The stent of the present invention has been developed for bifurcated and trifurcated regions and may provide a new approach for solving problems in this area.

All of the methods and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the methods and/or apparatus and in the steps or in the sequence of steps of the method described herein without departing from the concept, spirit and scope of the invention. More specifically, it will be apparent that certain elements may be substituted for the elements described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bakal, "Diagnosis and Management of Perigraft Leaks," 23rd Annual Scientific Meeting of SCVIR, San Francisco, Calif., pp 38–39, Feb. 28-Mar. 5, 1998.

Fallone, Wallace, Gianturco, "Elastic characteristics of the self-expanding metallic stents," *Invest. Radiol.*, 23:370–376, 1988.

Fort, "Coronary 'Y' stenting: A technique for angioplasty of bifurcation stenosis," *Can. J. Cardiol.*, 12(7):678–682, 1996.

Freitag et al., "Theoretical and experimental basis for the development of a dynamic airway stent," *Eur. Respir. J.*, 7:2038–2045, 1994.

Gillams, Dick, Dooley, Wallsten, Din, "Self-expandable stainless steel braided endoprosthesis for biliary strictures," *Radiology*, 174:137–140, 1990.

Günther, Vorwerk, Bohndorf et al., "Venous stenoses in dialysis shunts: Treatment with self-expanding metallic stents," *Radiology*, 170:401405, 1989.

Irving, Adam, Dick, Dondelinger, Lunderquist, Roche, "Gianturco expandable metallic biliary stents, results of a European clinical trial," *Radiology*, 172:321, 1989.

Milroy, Chapple, Eldin, Wallsten, "A new stent for the treatment of urethral strictures," *Br. J. Urol.*, 63:392–396, 1989.

Morita, "Interventional radiology for the treatment of inoperable malignant biliary obstruction," *Jap. J. Diagn. Imaging*, 17(5):526–535, 1997.

Murayama, Vinuela, Ulhoa, Akiba, Duckwiler, Gobin, Vinters, Greff, "Nonadhesive liquid embolic agent for cerebral arteriovenous malformations: Preliminary histopathological studies in swine rete mirabile," *Neurosurgery*, 43:1164–1175, 1998.

Nashef, Dromer, Velly, Labrousso, Couraud, "Expanding wire stents in benign tracheobronchial disease: Indications and complications," *Ann. Thorac. Surg.*, 54:937–940, 1992.

Palmaz, "Balloon-expandable intravascular stent," *AJR*, 150:1263–1269, 1988.

Peterson et al., "Gianturco-Rosch Z stents in tracheobronchial stenoses," *JVIR*, 6:925–931, 1995.

Schampaert, "The V-stent: a novel technique for coronary bifurcation stenting," *Cathet. Cardiovasc. Diagn.*, 39(3):320–1326, 1996.

Semba, "Endovascular Grafting in the Thoracic Aorta," 23rd Annual Scientific Meeting of SCVIR, San Francisco, Calif., pp. 39–42, Feb. 28-Mar. 5, 1998.

Shurman et al., "Neointimal hyperplasia in low-profile nitinol stents, Palmaz stents, and Wallstents: a comparative experimental study," *Cardiovasc. Intervent. Radiol.*, 19:248–254, 1996.

Taki, Yonekawa, Iwata, Uno, Yamashita, Amemiya, "A new liquid material for embolization of arteriovenous malformations," *AJNR*, 11:163–168, 1990.

Terada, Nakamura, Nakai et al., "Embolization of arteriovenous malformations with peripheral aneurysms using ethylene vinyl alcohol copolymer," *J. Neurosurg.*, 75:655–660, 1991.

Wallace, Charnsangavej, Ogawa et al., "Tracheobronchial tree: Expandable metallic stents used in experimental and clinical applications," *Radiology*, 158:309–312, 1986.

Wallsten, "Prosthesis comprising an expansible or contractile tubular body," U.S. Pat. No. 4,655,771, Issued Apr. 7, 1987.

What is claimed is:

1. A device suitable for implantation into an anatomical structure, comprising:
   a first plurality of wires defining a first leg, the first leg having a first distal portion;
   a second plurality of wires defining a second leg, the second leg having a second distal portion; and
   a common body having a distal end and a proximal portion, the common body being formed from at least the first and second pluralities of wires, the proximal portion of the common body being adjacent to the distal portions of both legs, and both ends of at least one wire from one of the pluralities being located proximate the distal end of the common body.

2. The device of claim 1, wherein the wires in the first and second pluralities comprise nitinol.

3. The device of claim 1, wherein the wires in the first and second pluralities comprise FePt, FePd or FeNiCoTi.

4. The device of claim 1, wherein the wires in the first and second pluralities comprise FeNiC, FeMnSi or FeMnSiCrNi.

5. The device of claim 1, wherein the wires in the first and second pluralities each have a diameter ranging in size from about 0.006 inches to about 0.014 inches.

6. The device of claim 1, wherein the first plurality of wires includes at least 6 wires.

7. The device of claim 1, wherein both the legs and the common body have tubular shapes with substantially uniform diameters.

8. The device of claim 1, wherein at least one of the legs is hand woven.

9. The device of claim 1, wherein at least one of the legs is machine woven.

10. The device of claim 1, further comprising a graft material attached to at least the common body.

11. The device of claim 10, wherein the graft material comprises woven Dacron.

12. The device of claim 10, wherein the graft material comprises polyurethane.

13. The device of claim 10, wherein the graft material comprises PTFE.

14. A stent, comprising:
   a first plurality of flexible tubular strands woven to form a first leg having a first distal portion, the flexible tubular strands in the first plurality crossing each other to form a first plurality of angles, at least one of the angles therein being obtuse;
   a second plurality of flexible tubular strands woven to form a second leg having a second distal portion, the flexible tubular strands in the second plurality crossing each other to form a second plurality of angles, at least one of the angles therein being obtuse; and
   a common body having a distal end and a common portion, the common body being formed from at least the first and second pluralities of flexible tubular strands, the common portion of the common body being adjacent to the distal portions of the first and second legs, and both ends of at least one flexible tubular strand from each of the pluralities of flexible tubular strands being located proximate the distal end of the common body.

15. The stent of claim 14, wherein the flexible tubular strands in the first and second pluralities comprise nitinol.

16. The stent of claim 14, wherein the flexible tubular strands in at least the first plurality comprise biodegradable filaments.

17. A stent, comprising:
   a first plurality of wires defining a first leg, the first leg having a first distal portion;
   a second plurality of wires defining a second leg, the second leg having a second distal portion;
   a third plurality of wires defining a third leg, the third leg having a third distal portion; and
   a common body having a proximal portion and a distal end, the common body being formed from at least the first, second and third pluralities of wires, the proximal portion of the common body being adjacent to the distal portions of each of the three legs.

18. The stent of claim 17, wherein the wires in each of the pluralities comprise nitinol.

19. The stent of claim 17, wherein the first plurality of wires includes at least 5 wires.

20. The stent of claim 17, wherein each of the legs and the common body have tubular shapes with substantially uniform diameters.

21. The stent of claim 17, wherein at least one of the legs is hand woven.

22. The stent of claim 17, wherein at least one of the legs is machine woven.

23. The stent of claim 17, further comprising a graft material attached to at least the common body.

24. The stent of claim 23, wherein the graft material comprises woven Dacron.

25. The stent of claim 23, wherein the graft material comprises polyurethane.

26. A stent comprising:

a first leg having a first axis and a first end, wherein the first leg comprises a first wire having a first segment and a second segment, the segments being separated by a bend in the first wire located proximate the first end of the first leg, the first segment extending helically in a first direction around the first axis away from the first end of the first leg, the second segment extending helically in a second direction around the first axis away from the first end of the first leg, the first and second segments crossing each other in a first plurality of locations;

a second leg having a second axis and a second end, wherein the second leg comprises a second wire having a first segment and a second segment, the segments being separated by a bend in the second wire located proximate the second end of the second leg, the first segment of the second wire extending helically in a first direction around the second axis away from the second end of the second leg, the second segment of the second wire extending helically in a second direction around the second axis away from the second end of the second leg, the first and second segments of the second wire crossing each other in a second plurality of locations; and a common body formed from at least one end of each of the wires.

27. The device of claim 26, wherein the first segment of the first wire is positioned farther from the first axis than the second segment of the first wire at least one location among the first plurality of locations.

28. The device of claim 26, wherein the first segment of the first wire is positioned farther from the first axis than the second segment of the first wire at each location of the first plurality of locations.

29. The device of claim 26, wherein the first and second wires comprise nitinol.

30. A method of creating a device suitable for implantation into an anatomical structure, the device having a first leg, a second leg, and a common body, each leg having an end and a distal portion, the common body having a proximal portion and a distal end, the method comprising:

bending the wires in a first plurality of wires to create first bent portions in the wires, the first bent portions being arranged to define the end of the first leg, each wire in the first plurality having two ends;

bending the wires in a second plurality of wires to create second bent portions in the wires, the second bent portions being arranged to define the end of the second leg, each wire in the second plurality having two ends;

weaving the ends of the wires in the first plurality to create the first leg;

weaving the ends of the wires in the second plurality to create the second leg; and weaving the ends of the wires in both pluralities to create the common body and the device;

wherein the proximal portion of the common body is adjacent to the distal portions of both legs and the two ends of at least one of the wires in the first plurality of wires are located proximate the distal end of the common body.

31. The method of claim 30, wherein the first bent portions are bends.

32. The method of claim 30, wherein the first bent portions are loops.

33. The method of claim 30, wherein the wires in the first and second pluralities comprise nitinol.

34. The method of claim 30, wherein the wires in the first and second pluralities each have a diameter ranging in size from about 0.006 inches to about 0.014 inches.

35. The method of claim 30, wherein the weaving the ends of the wires in the first plurality is by hand.

36. The method of claim 30, wherein the weaving the ends of the wires in the first plurality is by machine.

* * * * *

UNITED STATES PATENT AND TRADEMARK OFFICE
CERTIFICATE OF CORRECTION

PATENT NO.    : 6,409,750 B1
DATED         : June 25, 2002
INVENTOR(S)   : Hyodoh et al.

It is certified that error appears in the above-identified patent and that said Letters Patent is hereby corrected as shown below:

<u>Column 43,</u>
Line 31, please insert -- at -- between "wire" and "at".

Signed and Sealed this

Twenty-ninth Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,409,750 B1
DATED : June 25, 2002
INVENTOR(S) : Hyodoh et al.

It is certified that error appears in the above-identified patent and that said Letters Patent is hereby corrected as shown below:

Title page,
Item [56], References Cited, FOREIGN PATENT DOCUMENTS, please add:
-- DE       19703482 A1   8/1998
  EP       0804909       11/1997
  WO      97/16133     5/1997
  WO      98/11847     3/1998
  WO      98/19630     5/1998
  WO      98/46168     10/1998 --.

Signed and Sealed this

Thirty-first Day of August, 2004

JON W. DUDAS
*Director of the United States Patent and Trademark Office*